United States Patent [19]
Tasset et al.

[11] Patent Number: 6,028,186
[45] Date of Patent: *Feb. 22, 2000

[54] HIGH AFFINITY NUCLEIC ACID LIGANDS OF CYTOKINES

[75] Inventors: Diane Tasset; Nikos Pagratis; Sumedha Jayasena; Larry Gold, all of Boulder, Colo.

[73] Assignee: NeXstar Pharmaceuticals, Inc., Boulder, Colo.

[*] Notice: This patent is subject to a terminal disclaimer.

[21] Appl. No.: 08/481,710

[22] Filed: Jun. 7, 1995

Related U.S. Application Data

[63] Continuation-in-part of application No. 07/714,131, Jun. 10, 1991, Pat. No. 5,475,096, and a continuation-in-part of application No. 07/931,473, Aug. 17, 1992, Pat. No. 5,270,163, and a continuation-in-part of application No. 07/964,624, Oct. 21, 1992, Pat. No. 5,496,938, and a continuation-in-part of application No. 08/117,991, Sep. 8, 1993, abandoned, said application No. 07/714,131, is a continuation-in-part of application No. 07/536,428, Jun. 11, 1990, abandoned.

[51] Int. Cl.[7] .......................... C07H 21/02; C07H 21/04; C12Q 1/68; C12P 19/34

[52] U.S. Cl. ................... 536/24.31; 536/24.3; 536/23.1; 536/22.1; 435/6; 435/91.2; 935/77; 935/78

[58] Field of Search ................................ 536/23.1, 24.31, 536/22.1, 24.3; 435/6, 91.2; 935/77, 78

[56] References Cited

U.S. PATENT DOCUMENTS

| | | | |
|---|---|---|---|
| 5,270,163 | 12/1993 | Gold et al. | 435/6 |
| 5,599,917 | 2/1997 | Coppoloa | 536/22.1 |

FOREIGN PATENT DOCUMENTS

| | | |
|---|---|---|
| 2 183 661 | 6/1987 | United Kingdom . |
| WO 89/06694 | 7/1989 | WIPO . |
| WO 92/14843 | 9/1992 | WIPO . |
| WO 95/00529 | 1/1995 | WIPO . |

OTHER PUBLICATIONS

Alfa and Jay (1988) J. Immunology 141:2474.
Anderson et al. (1982) J. Biological Chemistry 257:11301.
Hahn et al. (1991) Exp. Hematol. 19:157.
Johnson et al. (1982) J. Immunology 129:2357.
Kelder et al. (1986) Methods in Enzymology 119:582.
Kwok et al. (1993) Immunology 78:131.
Le et al. (1984) J. Immunol. Meth. 69:61.
Meager et al. (1984) J. Interferon Research 4:619.
Oda et al. (1986) Hybridoma 5:329.
Ziai et al. (1986) Cancer Research 46:6187.
Wangoo et al. (1993) Clin. Exp. Immunol. 94:43.
Ramanathan et al. (1994) J. Biological Chemistry 269:24564.
Ramanathan et al. (1994) Transplantation 57:612.
Ramanathan et al. (1993) Biochemistry 32:3549.
Topp et al. (1993) Blood 82:2837.
Renz et al. (1995) Int. Arch. Allergy Immunol. 106:46.
Ashkenazi et al. (1991) Proc. Natl Acad. Sci. USA 88:10535.
Beutler et al. (1985) Science 229:869.
Brockhaus et al. (1990) Proc. Natl. Acad. Sci. USA 87:3127.
Fiedler et al. (1992) J. Lab Clin. Med. 120:574.
Gatanaga et al. (1990) Proc. Natl. Acad. Sci. USA 87:8781.
Gearing et al. (1994) Nature 370:555.
Haak–Frendscho et al. (1994) J. Immunology pp. 1347–1353.
Hinshaw et al. (1992) J. Trauma 33:568.
Kohno et al. (1990) Proc. Natl. Acad. Sci. USA 87:8331.
Lesslauer et al. (1991) Eur. J. Immunology 21:2883.
McGeehan et al. (1994) Nature 370:558.
Mohler et al. (1993) J. Immunology 151:1548.
Sandburg (1993) BioWorld Today, vol. 4, No. 188.
Sheehan et al. (1989) 142:3884.
Silva et al. (1990) J. Infect. Diseases 162:421.
Mosmann (1994) Science 265:193.
Clerici and Shearer (1993) Immunology Today 14:107.
Liew et al. (1989) Eur. J. Immunology 19:1227.
Kuhn et al. (1993) Cell pp. 263–274.
Sher et al. (1992) Immunological Reviews No. 127 pp. 183–204.
Mosmann and Moore (1991) Immunology Today A49–A53.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Sci. Acad. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

*Primary Examiner*—Stephanie Zitomer
*Attorney, Agent, or Firm*—Swanson & Bratschun LLC

[57] ABSTRACT

Methods are described for the identification and preparation of high-affinity nucleic acid ligands to cytokines. Included in the invention are specific nucleic acid ligands to IFN-gamma, IL-4, IL-10, TNF-alpha, and RANTES.

19 Claims, No Drawings

HIGH AFFINITY NUCLEIC ACID LIGANDS OF CYTOKINES

RELATED APPLICATIONS

This application is a Continuation-in-Part of U.S. patent application Ser. No. 07/714,131, filed Jun. 10, 1991, entitled Nucleic Acid Ligands now issued as U.S. Pat. No. 5,475,096, U.S. patent application Ser. No. 07/931,473, filed Aug. 17, 1992, entitled Methods for Identifying Nucleic Acid Ligands, now issued as U.S. Pat. No. 5,270,163, U.S. patent application Ser. No. 07/964,624, filed Oct. 21, 1992, entitled Methods of Producing Nucleic Acid Ligands now issued as U.S. Pat. No. 5,496,938 and U.S. patent application Ser. No. 08/117,991, filed Sep. 8, 1993, entitled High-Affinity Nucleic Acid Ligands Containing Modified Nucleotides, now abandoned (see U.S. Pat. No. 5,660,985). U.S. patent application Ser. No. 07/714,131 filed Jun. 10, 1991, now U.S. Pat. No. 5,475,096 is a Continuation-in-Part of U.S. patent application Ser. No. 07/536,428, filed Jun. 11, 1990, entitled Systematic Evolution of Ligands by Exponential Enrichment, now abandoned.

FIELD OF THE INVENTION

Described herein are methods for identifying and preparing high-affinity nucleic acid ligands to cytokines. The method utilized herein for identifying such nucleic acid ligands is called SELEX, an acronym for Systematic Evolution of Ligands by Exponential enrichment. This invention specifically includes methods for the identification of high affinity nucleic acid ligands of the following cytokines: IFN-gamma, IL-4, IL-10, TNFα, and RANTES.

Further disclosed are RNA ligands to IFN-ganmma, IL-4, IL-10, and TNFα. Also disclosed are DNA ligands to RANTES. Specific examples are provided of oligonucleotides containing nucleotide derivatives chemically modified at the 2'-positions of pyrimidines. The oligonucleotides of the present invention are useful as pharmaceuticals or diagnostic agents.

BACKGROUND OF THE INVENTION

Cytokines are a diverse group of small proteins that mediate cell signaling/communication. They exert their biological functions through specific receptors expressed on the surface of target cells.

Cytokines can be subdivided into several groups, including the immune/hematopoietins, interferons, tumor necrosis factor (TNF)-related molecules, and the chemokines. Representative immune/hematopoietins include erythropoietin (EPO), granulocyte/macrophage colony-stimulating factor (GM-CSF), granulocyte colony-stimulating factor (G-CSF), leukemia inhibition factor (LIF), oncostatin-M (OSM), ciliary neurotrophic factor (CNTF), growth hormone (GH), prolactin (PRL), interleukin (IL)-2, IL-3, IL-4, IL-5, IL-6, IL-7, IL-9, IL-10, and IL-12. Representative interferons (IFN) include IFNα, IFNβ, and IFN-gamma. Representative TNF family members include TNFα, interferon (IFN)β, gp$^{39}$ (CD40-L), CD27-L, CD30-L, and nerve growth factor (NGF). Representative chemrokines include platelet factor (PF)4, platelet basic protein (PBP), groα, MIG, ENA-78, macrophage inflammatory protein (MIP)1α, MIP1β, monocyte chemoattractant protein (MCP)-1, I-309, HC14, C10, Regulated on Activation, Normal T-cell Expressed, and Secreted (RANTES), and IL-8.

IFN-gamma

IFN-gamma was first described 30 years ago as an antiviral agent (Wheelock, 1965). Since that time the protein has been shown to be a remarkably pleiotropic cytokine which plays important roles in modulating virtually all phases of immune and inflammatory responses. The cDNAs for murine IFN-gamma (Gray and Goeddel, 1983) and human IFN-gamma (Gray and Goeddel, 1982) have been cloned, sequenced, and characterized.

IFN-gamma is a member of a family of proteins related by their ability to protect cells from viral infection. This family has been divided into three distinct classes based on a variety of criteria, IFN-alpha (originally known as Type I IFN or Leukocyte IFN), IFN-beta (also originally known as Type I IFN or Fibroblast IFN) and IFN-gamma (originally known as Type II IFN or Immune IFN). IFN-gamma is unrelated to the Type I interferons at both the genetic and protein levels (Gray, et al., 1982). The human and murine IFN-gamma proteins display a strict species specificity in their ability to bind to and activate human and murine cells. This is due at least in part to their modest homologies at both the cDNA and amino acid levels (60% and 40% respectively).

IFN-gamma is produced by a unique set of stimuli and only by T lymphocytes and natural killer (NK) cells. The human and murine genes for IFN-gamma are 6 kb in size, and each contain four exons and three introns. These genes have been localized to human chromosome 12 (12q24.1) and murine chromosome 10. Activation of the human gene leads to the transcription of a 1.2 kb mRNA that encodes a 166 amino acid polypeptide (Derynck, et al., 1982). The human protein contains a 23 residue amino terminal hydrophobic signal sequence which gets proteolytically removed, giving rise to a mature 143 residue positively charged polypeptide with a predicted molecular mass of 17 kDa. Variable post-translational enzymatic degradation of the positively charged carboxy terminus (Rinderknecht, et al., 1984) is responsible for the charge heterogeneity of the fully mature molecule. Proteins with six different carboxy termini have been detected for both natural and recombinant forms of IFN-gamma. Two polypeptides self-associate to form a homodimer with an apparent molecular mass of 34 kDa (Scahill, et al., 1983). The homodimer is the biologically active form of the protein. Mature human IFN-gamma contains no cysteine residues, thus the homodimer is held together entirely by noncovalent forces. This quaternary structure of the native protein explains its characteristic sensitivity to extremes of heat (protein denatured at temperatures above 56° C.), and pH (activity rapidly lost at pH values less than 4.0 and greater than 9.0) (Mulkerrin and Wetzel, 1989).

The remarkable pleiotropic effects of IFN-gamma are mediated through binding to a single type of IFN-gamma receptor. The structure and function of murine and human IFN-gamma receptors have been described (Schreiber, et al., 1992). These receptor proteins are expressed on nearly all cells (except erythrocytes), and platelets (Anderson, et al., 1982). The receptor binds ligand with high affinity (Kd=10$^-$9–10$^{-10}$M) and is expressed on most cells at modest levels (200–25,000 sites/cell). Upon IFN-gamma binding to the receptor at the cell surface, the intracellular domain of the receptor is phosphorylated at serine and threonine residues (Hershey, et al., 1990).

One of the major physiologic roles of IFN-gamma is as a regulator of immune response induction, specifically its ability to regulate expression of class I and II major histocompatibility (MHC) antigens on a variety of immunologically important cell types (Trinchieri and Perussia, 1985) Functionally, IFN-gamma dependent upregulation of MHC gene expression is an important step in promoting antigen presentation during the inductive phase of immune responses and may play a role in antitumor activity of IFN-gamma (Buchmeier and Schreiber, 1985).

Another major physiologic role for IFN-gamma is its ability to activate human macrophage cytotoxicity (Schreiber and Celada, 1985). Therefore, IFN-gamma is the primary cytokine responsible for inducing nonspecific cell-mediated mechanisms of host defense toward a variety of intracellular and extracellular parasites and neoplastic cells (Bancroft, et al., 1987). This activation is a result of several distinct functions of IFN-gamma. IFN-gamma has been shown to effect the differentiation of immature myeloid precursors into mature monocytes (Adams and Hamilton, 1984). IFN-gamma promotes antigen presentation in macrophages, through the induction of MHC class II expression as described above, but also by increasing levels of several intracellular enzymes important for antigen processing (Allen and Unanue, 1987). Macrophage cell surface proteins such as ICAM-1 are upregulated by IFN-gamma, thus enhancing the functional results of the macrophage-T cell interaction during antigen presentation (Mantovani and Dejana, 1989). IFN-gamma activates the production of macrophage derived cytocidal compounds such as reactive oxygen- and reactive nitrogen-intermediates and tumor necrosis factor-a (TNF-a) (Ding, et al., 1988). IFN-gamma also reduces the susceptibility of macrophage populations to microbial infections (Bancroft, et al., 1989). Animal models have been used to study the role of IFN-gamma in the clearance of microbial pathogens. Neutralizing monoclonal antibodies to IFN-gamma were injected into mice before infecting them with sublethal doses of various microbial pathogens. These mice lost their ability to resolve the infection initiated with *Listeria monocytogenes* (Buchmeier and Schreiber, 1985), *Toxoplasma gondii* (Suzuki, et al., 1988), or *Leishmania major* (Green, et al., 1990).

Besides these nonspecific cell mediated cytocidal activities, IFN-gamma also enhances other macrophage immune response effector functions. IFN-gamma up-regulates expression of Fc receptors on monocytes/macrophages (FcgRI), thus enhancing the capacity of the macrophage for antibody dependent cell killing (Erbe, et al., 1990). IFN-gamma also promotes humoral immunity through enhancement of complement activity. It does this in two ways, i) by promoting the synthesis of a variety of complement proteins (ie., C2, C4, and Factor B) by macrophages and fibroblasts, and ii) by regulating the expression of complement receptors on the mononuclear phagocyte plasma membrane (Strunk, et al., 1985).

IFN-gamma also exerts its effects on other cells of the immune system. It regulates immunoglobulin isotype switching on B cells (Snapper and Paul, 1987). IFN-gamma plays a positive role in the generation of $CD8^+$ cytolytic T cells (CTLs) (Landolfo, et al., 1985) and enhances NK cell activity. Recently, it has been unequivocally established that $CD4^+$ T cells do not constitute a homogeneous class of cells. Indeed, a paradigm of lymphokine biology and of the function of $CD4^+$ T cells has arisen, the so-called Th1/Th2 paradigm (for a review see Paul and Seder, 1994). The $T_{H1}$ clones, through their production of IFN-gamma, are well suited to induce enhanced microbicidal and antitumor activity in macrophages as detailed above (enhanced cellular immunity), while the Th2 clones make products (IL-4, IL-5, IL-6, IL-10, IL-13) that are well adapted to act in helping B cells develop into antibody-producing cells (enhanced humoral immunity). The role played by IFN-gamma at this crucial nexus of T cell effector function is fundamental to the success or failure of the immune response.

IFN-gamma plays a major role in promoting inflammatory responses both directly, and indirectly through its ability to enhance TNF-α production. During an inflammatory response, cells leave the circulation and migrate to the point of infection. During this process they must first bind to and then extravasate through vascular endothelium. Both IFN-gamma and TNF-α can promote the expression of overlapping sets of cell adhesion molecules (ICAM-1, E-selectin, and others) that play an important role in this process (Pober, et al., 1986; Thornhill, et al., 1991). In fact, experiments have shown that these two cytokines exhibit synergistic effects in up-regulating cell adhesion molecules in vivo (Munro, et al., 1989). One can envision microbial infections in which the microorganism is already widespread at the time the immune response develops or in which the response does not quickly rid the host of the infectious agent. This results in continued T cell activation inducing both local inflammation and tissue damage with ensuing loss of normal function. Indeed, when the infectious agent is of little intrinsic pathogenicity, the disease induced by the infection may largely reflect the consequences of such a response.

Excessive production of IFN-gamma may play a role in autoimmune disorders (for review see Paul and Seder, 1994 and Steinman, 1993). The mechanism for this may involve excessive tissue damage due to aberrant or enhanced expression of class I and class II MHC molecules or the role of an excessive $T_{H1}$ cellular response. A role for IFN-gamma and the tissue-damaging effects of immune responses mediated by $T_{H1}$-like cells has been suggested in autoimmune disorders such as rheumatoid arthritis (Feldmann, 1989), juvenile diabetes (Rapoport, et al., 1993), myasthenia gravis (Gu, et al., 1995), severe inflammatory bowel disease (Kuhn, et al., 1993), and multiple sclerosis (Traugott, 1988).

IL-4

Interleukin-4 (IL-4) is a remarkably pleiotropic cytokine first identified in 1982 as a B cell growth factor (BCGF) (Howard, et al., 1982). In that same year, IL-4 was identified as an IgG1 enhancing factor (Isakson, et al., 1982). Because of the effect IL-4 has on B cells, it was first called BCGF-1, later termed BSF-1 (B-cell stimulatory factor-1), and in 1986 it was given the name IL-4. The cDNAs for murine IL-4 (Noma, et al., 1986; Lee, et al., 1986) and human IL-4 (Yokota, et al., 1986) have been cloned, sequenced, and characterized.

IL-4 can be regarded as the prototypic member of a family of immune recognition-induced lymphokines designated the "IL-4 family" (for a review see Paul, 1991). This family consists of IL-4, IL-5, IL-3, and granulocyte-macrophage colony-stimulating factor (GM-CSF). The properties shared by these proteins leads to this grouping and include, i) the linkage of the genes for the members of the family (van Leeuwen, et al., 1989), ii) the action of each member of the family as a hematopoietic growth factor in addition to any effects it may exert on lymphoid cells, iii) the receptors for these proteins are all members of the hematopoietin family of receptors (Bazan, 1990a), and iv) coexpression of these factors by a subpopulation of cloned $CD4^+$ T cells (the so-called $T_{H2}$ cells) (Mosmann, et al., 1989) and by mast cells (Plaut, et al., 1989).

The remarkable pleiotropic effects of IL-4 are mediated through binding to cell surface receptors (IL-4R). The murine IL-4R (Mosely, et al., 1989; Harada, et al., 1990), and the human IL-4R (Idzerda, et al., 1990; Galizzi, et al., 1990) have been cloned, sequenced, and characterized. IL-4R are present on a variety of hematopoietic (Park, et al., 1987) and nonhematopoietic cells (Lowenthal, et al., 1988). On both human and murine resting T and B cells, IL-4R are present in low numbers (<400) and are regulated by cytokines and other factors. The receptor binds IL-4 with high affinity (Kd=$10^{-10}$ M). Now that most of the receptors for immunoregulatory and hematopoietic cytokines have been cloned, it is apparent that the majority of these receptors fall into a large family. This hematopoietic cytokine receptor superfamily includes receptors for IL-4, IL-2 ($\beta$ and $\gamma$ chains), IL-7, IL-9, and IL-13 which modulate the lymphoid system; and receptors for erythropoietin, granulocyte-colony stimulating factor (G-CSF), GM-CSF, IL-3, and IL-5 which modulate the hematopoetic system. The superfamily also includes receptors for factors believed to normally function outside the immune and hematopoietic systems, including receptors for growth hormone (GH), prolactin, leukemia inhibitory factor (LIF), IL-6, IL-11, and ciliary neurotrophic factor (CNF) (for a review see Kishimoto, et al., 1994).

A general first step in the signaling processes of immune and hematopoietic cytokines may be ligand-induced dimerization of receptor components whose cytoplasmic regions interact to initiate a downstream signaling cascade. The IL-4 receptor has a long putative intracellular domain (553 amino acids in mouse, 569 in human) with no known consensus sequences for kinase activity or for nucleotide-binding regions. The biochemical nature of signals induced by the binding of IL-4 to its receptor have not been elucidated. It does appear that the cytosolic domain of the receptor is essential for its signaling function (Mosely, et al., 1989). Ligand induced dimerization of the IL-4 receptor appears to be a critical first step in IL-4 mediated signal transduction.

One of the major physiologic roles of IL-4 is as a B lymphocyte activation and differentiation factor (Rabin, et al., 1985; Oliver, et al., 1985). The protein was first isolated based on this activity. In this regard, IL-4 activates production of IgG1 (Vitetta, et al., 1985), but is also responsible for isotype switching in B cells from production of IgG to IgE immunoglobulins (Coffman, et al., 1986; Lebman and Coffman, 1988, Del Prete, et al., 1988). The effect of IL-4 on the in vivo regulation of IgE has been clearly demonstrated. Neutralization of IL-4 by treatment with a monoclonal anti-IL-4 antibody (Finkelman, et al., 1986) or a monoclonal antibody to the IL-4 receptor (Finkelman, et al., 1990) will block the IgE response. A recombinant soluble IL-4 receptor has been shown to inhibit IgE production by up to 85% in vivo (Sato, et al., 1993). IL-4 deficient mice produced by gene-targeting in murine embryonic stem cells have normal B and T cell development, but serum levels of IgG1 and IgE are strongly reduced (Kahn, et al., 1991). IL-4 augmented IgE production leads to an atopic state (allergy/asthma) (Finkelman, et al., 1989; Katona, et al., 1991).

The IL-4 mediated up-regulation of IgG1 may play a role in the inflammation cascade. IgG1 has recently been shown to form immune complexes which bind to the cellular receptors for the Fc domain of immunoglobulins (FcRs) leading to an inflammatory response (Sylvestre and Ravetch, 1994; Ravetch, 1994). IL-4 transgenic mice have been produced that hyperexpress IL-4 (Tepper, et al., 1990). These mice have elevated levels of serum IgG1 and IgE and they develop allergic inflammatory disease. These findings demonstrate the critical role IL-4 plays in the humoral immune response.

Another major physiologic role for IL-4 is as a T lymphocyte growth factor (Hu-Li, et al., 1987; Spits, et al., 1987). IL-4 enhances the proliferation of precursors of cytotoxic T cells (CTLs) and their differentiation into active $CD8^+$ CTLs (Widmer and Grabstein, 1987; Trenn, 1988). IL-4 appears to augment the IL-2 driven induction of lymphokine-activated killer (LAK) cells (Higuchi, et al., 1989), which have been shown to lyse a variety of tumor cell targets without major histocompatibility complex (MHC) restriction. The role played by IL-4 at this crucial nexus of T cell effector function is fundamental to the success or failure of the immune response.

IL-4 has been shown to affect nonlymphoid hematopoietic cells in a variety of ways. IL-4 has been shown to modulate monocyte/macrophage growth (McInnes and Rennick, 1988; Jansen, et al., 1989) while enhancing their differentiation and cytotoxic activity for certain tumor cells (Crawford, et al., 1987; Te Velde, et al., 1988). IL-4 also has activity as a stimulant of mast cell growth (Mosmann, et al., 1986; Brown, et al., 1987), and increases production and recruitment of eosinophils (Tepper, et al., 1989).

IL-4 alone or in conjunction with other cytokines can promote the expression of a variety of cell-surface molecules on various cell types with diverse implications for disease. Specifically, IL-4 can interact with tumor necrosis factor (TNF) to selectively enhance vascular cell adhesion molecule-1 (VCAM-1) expression contributing to T cell extravasation at sites of inflammation (Briscoe, et al., 1992). IL-4 alone or in combination with TNF or IFN-gamma has been shown to increase both MHC antigen and tumor-associated antigen expression on a variety of neoplastic cells (Hoon, et al., 1991).

As detailed above, IgG1 immune complexes bind to the cellular receptors for the Fc domain of immunoglobulins (FcRs) leading to an inflammatory response. Inhibition of IL-4 and the subsequent reduction in IL-4 mediated IgG1 expression may prove efficacious against immune complex inflammatory disease states. Indeed, inhibitory ligands to IL-4 might also prevent the IL-4 mediated overexpression of VCAM-1, thus attenuating the ability of T cells to extravasate at sites of inflammation.

Inhibition of IL-4 activity with a monoclonal antibody, a recombinant soluble IL-4 receptor, or gene knock-out, results in a reduction of serum IgE levels. An inhibitory oligonucleotide ligand to IL-4 could be clinically effective against allergy and allergic asthma.

A recent report has described a disorder in bone homeostasis in transgenic mice that inappropriately express IL-4 under the direction of the lymphocyte-specific proximal promoter for the lck gene (Lewis, et al., 1993). Bone disease in these mice resulted from markedly decreased bone formation by osteoblasts, features identical to those found in human osteoporosis. Inhibiting this IL-4 mediated reduction in osteoblast activity may prove beneficial against osteoporosis.

Graft-versus-host disease (GVHD) is a major complication of human tissue transplantation. GVHD does not exist as a single clinical manifestation but can involve immunologic abnormalities ranging from immunodeficiency to systemic autoimmunities (Ferrara, et al., 1991). These systemic autoimmunities include clinical and serological manifestations of human systemic lupus erythematosus (SLE). Several murine models of SLE have been developed (Gleichmann, et al., 1982; van Rappard-van Der Veen, et al., 1982), and the induction of systemic GVHD in mice has been described (Via, et al., 1988). Two recent studies have shown in vivo efficacy of a mouse monoclonal antibody to IL-4 in preventing GVHD and SLE in these murine model systems (Umland, et al., 1992; Ushiyama, et al., 1995). These observations suggest that an inhibitor of human IL-4 may be effective in treatment of chronic systemic autoimmunities such as SLE and GVHD.

A variety of microbicidal infections are characterized by depressed cellular but enhanced humoral immune responses, which suggests a $T_{H2}$ type of response to infection. This $T_{H2}$ phenotype is characterized by T cell secretion of IL-4, as detailed earlier. IL-4 blocks the microbicidal activity of IFN-gamma activated macrophages in fighting *Leishmania major* infection (Liew, et al., 1989; Leal, et al., 1993). Inhibition of IL-4 would enhance the $T_{H1}$ effector arm of the immune response enhancing cellular immunity and leading to the resolution of infection. Neutralization of IL-4 in vivo allows mice otherwise susceptible to *Leishmania major* infection to fight off the parasite and clear the infection (Heinzel, et al., 1989). Several informative studies have looked at the $T_{H1}/T_{H2}$ phenotypic distinction in infected mice, and suggest a $T_{H1}$ dominated response being most effective in fighting microbial infection (for a review, see Sher and Coffman, 1992).

IL-10

IL-10 is a cytokine produced by the Th2 cells, but rot Th1 cells, and inhibits synthesis of most of all cytokines produced by Th1 cells but not Th2 cells (Mosmann et al., 1991). In addition to the effect on $CD4^+$ cells with Th1 phenotype, IL-10 also inhibits $CD8^+$ T cells with "Th1-like" phenotype. IL-10 is a potent suppressor of macrophage activation. It can suppress the production of proinflammatory cytokines, including TNFα, IL-1, IL-6, IL-8 and IFN-gamma. Overall, these results suggest that IL-10 is a potent macrophage deactivator and an effective anti-inflammatory reagent. In addition, IL-10 prevents the IFN-γ-induced synthesis of nitric oxide, resulting in decreased resistance to intracellular parasites (Gazzinelli et al., 1992).

Both human and mouse (hIL-10 and mIL-10, respectively) have been cloned and expressed (Moore et al., 1990; Vieira et al., 1991). The two cDNAs exhibit high degree of nucleotide sequence homology (>80%) throughout and encode very similar open reading frames (73% amino acid homology). Both proteins are expressed as noncovalent homodimers that are acid labile (Moore et al., 1993). Whether monomers are equally bioactive is not clear yet. Based on the primary structure IL-10 has been categorized into the four a-helix bundle family of cytokines (Shanafelt et al.,1991). Possibly due to high degree of sequence homology and similar structure hIL-10 has been shown to be active on mouse cells (Moore et al., 1993) but not vice a versa. hIL-10 is an 18 kDa polypeptide with no detectable carbohydrate; however, in mIL-10 there is one N-linked glycosylation. The recombinant hIL-10 has been expressed in CHO cells, COS7 cells, mouse myeloma cells, the baculovirus expression system and *E. coli*. The rIL-10 expressed in these systems have indistinguishable biological behavior (Moore et al.,1993).

Parasitic infection often leads to polarized immune response of either Th1 or Th2 type which can mediate protection or susceptibility. The outcome of a parasitic infection depends on the nature of the parasite and the host. The best understood example is *Leishmania major* infection in mice. *L. major* is a protozoan parasite that establishes an intracellular infection in macrophages, where it is mainly localized in phagolysosomes. Activated macrophages can efficiently destroy the intracellular parasite and thus parasitic protection is achieved by macrophage activation. Nonactivated macrophages do not kill these organisms. As expected, activation of macrophages upon IFN-gamma treatment enhanced the protection, whereas IL-4 and IL-10 blocked the increased microbicidal activity induced by IFN-gamma (Liew et al., 1989). In most inbred strains (example, C57/BL6) cutaneous infection of *L. major* often leads to localized infection with spontaneous healing and confers resistance to reinfection. However, in BALB/c mice, *L. major* infection induces nonprotective immune response by producing IL-4. The antibody response mediated by IL-4 is ineffective and leads to death (Howard et al., 1980). In healing strains a strong Th1 response has been noticed with high level of IFN-γ, whereas in susceptible BALB/c mice a nonproductive Th2 response with significant levels of IL-4 was found (Heinzel et al., 1991). Further it was shown that a single injection of monoclonal anti-IFN-gamma antibody can convert a resistance into a susceptible mouse (Belosevic et al., 1989). As expected, the treatment of BALB/c mice with anti-IL-4 antibody led to the development of Th1 response and healing (Sher & Coffman, 1992). Thus, depending on the nature of the pathogen, changing the immune response to a T cell subset with a protective phenotype can lead to therapeutic intervention of the disease state. Understanding the regulation between the Th1 and Th2 phenotype mediated by cytokines will help in designing cytokine-antagonist in therapeutics. The production of IL-10 is strongly increased in mice infected with various pathogens such as *Leishmania major, Schistosoma mansoni, Trypanosoma cruzi* and *Mycobacterium Leprae* (Sher, et al, 1992; Salgame etal., 1991, Heinzel et al., 1991).

When designing immune therapy to facilitate mounting the right arm of defense mechanism toward pathogens, it is important to maintain a balance between the two arms also. Th2-type responses may be important in controlling the tissue damage mediated by Th1 cells during the response to an intracellular infectious agent. Keeping some Th1 cells functioning in a predominantly Th2 environment can help abrogate damaging effects of Th1 by secreting IL-10 and IL-4. One extreme of the spectrum of Th1/Th2 is reflected in transgenic mice lacking the IL-10 gene (Kuhn et al., 1993). The IL-10 deficient mouse is normal with respect to its development of T and B cell subsets. However these mice develop chronic enterocolitis (or inflammatory bowel disease) due to chronic inflammation via continuous overproduction of cytokines such as TNFα and IFN-gamma(Th1 response).

IL-12 can also induce the development of the Th1 subset. By using *Lysteria monocytogen*, an intracellular gram-positive bacterium, infection in antibody T cell receptor transgenic mice as a model it has been shown that IL-10 can block the production of IL-12 from macrophages (Hsieh et al.,1993) Thus an IL-10-antagonist will tip the Th1/Th2 population predominantly to Th2 type environment by 1, preventing the inhibition of the production of Th1 cytokines 2 by allowing the production of a cytokine that induces the development of Th1 subset.

With experimental evidence in hand it has been proposed that the resistance and/or progression to AIDS is dependent on a Th1/Th2 stage of an individual (Clerici & Shearer, 1993). This hypothesis is based on the findings that progression to AIDS is characterized by loss of IL-2 and IFN-gamma production (loss of Th1 response) with increase in IL-4 and IL-10 (acquired Th2 response). Many seronegatives (HIV-exposed individuals) generate a strong Th1-type response. It is important to note that after seroconversion both IL-4 and IL-10 levels go up at the expense of IL-4 and IFN-gamma. However, in full-blown AIDS patients, Th2 response seems to be mediated by high levels of IL-10 but not with IL-4, the level of which goes down to normal in these individuals. An anti-IL-10 reagent may serve as a potential therapeutic in shifting the Th2 response to Th1 in AIDS patients to offer protection.

TNFα

TNFα is an extracellular cytokine and a central mediator of the immune and inflammatory response (Beutler et al., 1989; Vassalli, 1992). It is a homo-trimer (Smith et al., 1987, Eck et al., 1988), and has a subunit size of 17 kD. It circulates at concentrations of less than 5 pg/ml in healthy individuals (Dinarello et al., 1993) and it can go as high as 1000 pg/ml in patients with sepsis syndrome (Casey et al., 1993). The human TNFα is nonglycosylated, whereas in some other species (notably the mouse) glycosylation occurs on a single N-linked site in the mature protein, but the sugar moiety is not essential for biological activity (Beutler et al., 1989). The human TNFα is acidic with a pH of 5.3 (Aggarwal et al., 1985). Each TNFα subunit consists of an anti parallel β-sandwich and it participates in a trimer formation by an edge-to-face packing of β-sheets. The structure of the TNFα trimer resembles the "jelly-roll" structural motif characteristic of viral coat proteins (Jones et al., 1989). TNFα is a relatively stable molecule and may be exposed to chaotropic agents such as urea, SDS, or guanidinium hydrochloride, and renatured with recovery of as much as 50% of the initial biological activity. The TNFα renaturability may reflect the limited number of internal disulfide bonds (one per monomer) required for maintenance of structure (Beutler et al., 1989).

Another related molecule, TNFβ, has the same bioactivity as TNFα. The interspecies sequence identity within the TNFα and TNFβ families is 71% and 61%, respectively (Beutler et al., 1989). The sequence identity between hTNF-α and hTNF-β is only 29% (Beutler et al., 1989). Despite their low similarity, both hTNFα and hTNFβ bind to the same receptors with comparable affinities.

TNFα mediates its bioactivity through binding to cell surface receptors. The TNFα receptors are found on the surface of virtually all somatic cells tested (Vassalli, 1992). Two distinct TNFα receptors have been characterized of apparent molecular weights 55 kD (p55 TNFα-R1) and 75 kD (p75 TNFα-R2) (Hohmann et al., 1989; Brockhaus et al., 1990; Loetscher et al., 1991). Both receptors bind TNFα and TNFβ with high affinities (Kd=0.3–0.6 nM) (Loetscher et al., 1990; Schall et al., 1990; Pennica et al., 1992).

TNFα has diverse activities, and thus is implicated in several diseases as follows:

Septic shock. Sepsis incidents have been increasing for the last 60 years and is the most common cause of death in intensive care units in the United States (Parrillo, 1991). The mortality of septic shock remains at approximately 50% despite the standard use of aggressive antibiotics and cardiovascular support for the past 10 years (Parrillo, 1991). The evidence implicating TNFα in sepsis is as follows. Pretreatment of mice or baboons with monoclonal antibodies to TNFα protects them from lethal doses of *E. coli* LPS (Beutler et al., 1985). Anti-TNFα antibodies protect primates against lethal endotoxin sepsis and against lethal *S. aureus*-induced shock (Fiedler et al., 1992; Hinshaw et al., 1992). Soluble-TNFα-receptor (p55)-IgG-Fc fusions (TNFα receptor immunoadhesin) were found to protect mice from endotoxic shock, even when administered 1 hr after endotoxin infusion. The same immunoadhesin was also effective against listeriosis in mice (Haak-Frendscho et al., 1994). Another immunoadhesin based on the p75 receptor was also shown to be effective in lethal endotoxemia and it was functioning simultaneously as both TNFα carrier and TNFα antagonist (Mohler et al., 1993).

Cachexia. In vivo administration of TNFα causes cachexia in mice (Oliff et al., 1987). Therefore, TNFα antagonists may protect cancer or AIDS infected patients from cachexia.

Cerebral malaria. High levels of TNFα are associated with poor prognosis in children with cerebral malaria, and antibodies to TNFα protect mice from cerebral complications of *Plasmodium berghei* infection (Grau et al., 1987).

Arthritis. Antibodies to TNFα reduce the production of the inflammatory cytokine, IL-1 in synovial cells (Brennan et al., 1989). TNFα is an inducer of collagenase, the major destructive protease in rheumatoid arthritis (Brennan et al., 1989). Anti-TNFα antibodies were found to ameliorate joint disease in murine collagen-induced arthritis (Williams et al., 1992). Transgenic mice carrying the hTNFα gene develop arthritis which can be prevented by in vivo administration of a monoclonal antibody against hTNFα (Keffer et al., 1991).

Graft Rejection and Graft versus Host Reaction (GVHR). TNFα has been implicated in the acute phase of graft-versus-host disease and in renal allograft rejection. Antagonists of TNFα may then be able to prevent these life-threatening conditions. Anti-TNFα antibodies have been found to delay graft rejection in experimental animals (Piguet, 1992). Also, injection of anti-TNFα antibodies during the acute phase of GVHR reduces mortality, and the severity of intestinal, epidermal, and alveolar lesions (Piguet, 1992). Clinical trials of the efficacy of anti-TNFα antibody in human bone marrow transplantation are underway.

AIDS. Studies of intracellular signal transduction pathways revealed that TNFα induces proteins that bind to kB-like enhancer elements and thus takes part in the control of NF-kB-inducible genes (Lenardo et al., 1989; Lowenthal et al., 1989; Osborn et al., 1989). The antiviral activity of TNFα at least in part is mediated by the interaction of NF-kB with a virus-inducible element in the β-interferon gene (Goldfeld et al., 1989; Visvanathan et al., 1989). By an analogous mechanism, TNFα appears to activate human immunodeficiency virus type I (Duh et al., 1989; Folks et al., 1989). Therefore, TNFα antagonists may prove useful in delaying the activation of the AIDS virus and may work in conjunction with other treatments in the cure of AIDS.

Parkinson's disease. Recently, elevated TNFα levels have been found in the brain and the cerebrospinal fluid of Parkinsonian patients (Mogi et al., 1994). This report speculates that elevated TNFα levels may be related to neuronal degeneration associated with the disease.

RANTES

RANTES is a small (MW 8-kD) highly basic (pI~9.5) chemokine that belongs to the CC group (Schall, 1991; Baggiolini et al., 1994). It does not appear to be glycosylated (Schall, 1991) and is a chemoattractant for monocytes (Schall et al., 1990; Wang et al., 1993; Wiedermann et al., 1993), basophils (Bischoff et al., 1993; Kuna et al., 1993), eosinophils (Rot et al., 1992), and CD4+/UCHL1+ T lymphocytes which are thought to be prestimulated or primed helper T cells involved in memory T cell function (Schall et al., 1990). RANTES is not only a chemoattractant but it also stimulates cells to release their effectors leading to tissue damage. For example, RANTES causes histamine release from basophils (Kuna et al., 1992; Kuna et al., 1993; Alam et al., 1993). It also causes the secretion of eosinophil basic peptide (Alam et al., 1993) and the production of oxygen free radicals (Rot et al., 1992) by eosinophils.

Initially, it was thought that RANTES was synthesized by activated T cells but recently other cells were found to synthesize it very fast upon stimulation. RANTES mRNA is expressed late (3 to 5 days) after activation of resting T cells, whereas in fibroblasts, renal epithelial and mesangial cells, RANTES mRNA is quickly up-regulated by TNFα stimulation (Nelson et al., 1993).

Receptors for RANTES have been identified. There is a promiscuous receptor on the surface of erythrocytes that binds all chemokines with a Kd=5 nM (Horuk et al., 1993; Neote et al., 1993). This receptor is thought to be a sink for chemokines to help in the establishment of chemotactic gradients. Signal transducing receptors have also been identified and cloned (Gao et al., 1993; Neote et al., 1993; Van-Riper et al., 1993; Wang et al., 1993). Monocytes carry a G-protein coupled receptor that binds RANTES with estimated Kd of 400 pM, but also MCAF and MIP-1a with lower affinities (estimated Kd of 6 and 1.6 nM respectively) (Wang et al., 1993). A receptor molecule has been cloned from neutrophils that can bind RANTES with a lower affinity of about 50 nM (Gao et al., 1993).

Disease State. RANTES antagonists may have therapeutic application in inflammation. Blockage of the chemoattractant and effector cell activation properties of RANTES would block local inflammation and tissue damage. The mechanism of action of the RANTES antagonist will be the inhibition of RANTES binding to cell surface receptors.

RANTES is chemoattractant for monocytes, basophils, eosinophils and memory lymphocytes. Basophils are the major source of mediators such as histamine and peptido-leukotrienes, and are an essential element of the late-phase responses to allergens in hypersensitivity diseases. These cells are also involved in other inflammatory pathologies, including certain autoimmune reactions, parasitic infections and inflammatory bowel diseases. In these conditions, basophil recruitment and activation is independent of IgE. Numerous reports have accumulated over the years that describe the effects of a group of elusive stimuli operationally called "histamine-releasing factors." A large number of these elusive stimuli may well be contributed by RANTES.

Eosinophils also are important in allergic inflamation, and together with lymphocytes, form prominent infiltrates in the bronchial mucosa of patients with asthma. They are believed to be the cause of epithelial damage and the characteristic airway hyper-reactivity. The recruitment of lymphocytes of the Th2 type, which comigrate with eosinophils into sites of late-phase reactions, is an important source of other chemoattractant cytokines and growth factors that prime eosinophils.

RANTES, with its effects on monocytes, basophils, eosinophils and lymphocytes appears to be a potent stimulator of effector-cell accumulation and activation in chronic inflammatory diseases and in particular, allergic inflammation.

The recruitment system of inflammatory cells has some redundancy built into it. However, RANTES has some unique properties. It is a more potent chemoattractant than MCP-1 and MIP-1α, while MCP-1 is more potent stimulator of histamine release from basophils (Baggiolini et al., 1994). RANTES causes the production of oxygen radicals by eosinophils while MIP-1α cannot (Rot et al., 1992). RANTES is as potent as C5a in the recruitment of eosinphils, but not as potent a trigger of the eosinophil oxidation burst (Rot et al., 1992). C5a is a very potent chemoattractant: however, it lacks the specificity of RANTES. It attracts not only basophils and eosinophils but also neutrophils. Since the eosinophils, but not the neutrophils, are important in the pathophysiology of some inflammatory conditions, such as the allergen-induced late-phase reaction and asthma, specific chemoattractants such as RANTES are expected to be involved.

Using in situ hybridization, RANTES expression has been found in interstitial mononuclear cells and proximal tubular epithelial cells in human kidney transplants undergoing rejection. Antibody staining revealed the presence of RANTES not only within the interstitial infiltrate and renal tubular epithelial cells but also in high abundance in inflamed endothelium (Wiedermann et al., 1993). Based on these results a haptotactic mechanism was postulated. Haptotaxis is defined as cell migration induced by surface-bound gradients. The haptotactic mechanism was supported by in vitro experiments and anti-RANTES antibodies have been found to prevent that in vitro haptotaxis.

Human rheumatoid synovial fibroblasts express mRNA for RANTES and IL-8 after stimulation with TNFα and IL-1β (Rathanaswami et al., 1993). There is a differential regulation of expression of IL-8 and RANTES mRNA. Cycloheximide enhanced the mRNA levels for IL-8 and RANTES after stimulation with IL-1β but reduced the levels of RANTES mRNA after stimulation with TNFα. Also, IL-4 down-regulates and IFN-gamma enhances the TNFα and IL-1β induced increase in RANTES mRNA, whereas the induction of IL-8 mRNA by TNFα or IL-1β was inhibited by IFN-gamma and augmented by IL-4. Moreover, the combination of TNFα and IL-1β synergistically increased the level of IL-8 mRNA, whereas under the same conditions, the levels of RANTES mRNA were less than those induced with TNFα alone. These studies suggest that the synovial fibroblasts may participate in the ongoing inflammatory process in rheumatoid arthritis, and RANTES might be one of the participating effectors. The observed differential regulation of IL-8 and RANTES indicates that the type of cellular infiltrate and the progress of the inflammatory disease is likely to depend on the relative levels of stimulatory and inhibitory cytokines.

RANTES has also been implicated in atherosclerosis and possibly in postangioplasty restenosis (Schall, 1991). The participation of MCP-1 in atherosclerosis has been studied to a greater extent. Recently mRNAs for RANTES, MIP-1α and MIP-1β have been detected in in situ in normal carotid plaque and heart transplant atherosclerosis. RANTES mRNA is not detected in the same cells expressing MIP-1a and MIP-1β, but it is expressed in lymphocytes and macrophages typically more proximal to the lumen. The data argue for positive feed-back mechanisms for the CC chemokines and possible differential expression of these chemokines at various stages in the progression of arterial disease.

Finally, elevated RANTES levels have been correlated with endometriosis (Khorram et al., 1993). RANTES levels were elevated in pelvic fluids from women with endometriosis, and these levels correlate with the severity of the disease.

Protein Homology between Human and Animal. The murine RANTES has been cloned (Schall et al., 1992). Sequence analysis revealed 85% amino acid identity between the human and mouse proteins. The human and murine RANTES exhibit immune crossreactivity. Boyden chamber chemotaxis experiments reveal some lack of species specificity in monocyte chemoattractant potential, as recombinant muRANTES attracts human monocytes in a dose-dependent fashion in vitro. Also, hRANTES transfection into mouse tumor cell lines produce tumors in which the secretion of hRANTES by those tumors correlates with increased murine monocyte infiltration in vivo (Schall et al., 1992).

SELEX

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands now issued as U.S. Pat. No. 5,475,096," U.S. patent application Ser. No. 07/931,473, filed Aug. 17, 1992, entitled "Nucleic Acid Ligands," now U.S. Pat. No. 5,270,163 (see also WO91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (see U.S. Pat. No. 5,707,796), describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands", now abandoned, (see U.S. Pat. No. 5,763,177) describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now abandoned (see U.S. Pat. No. 5,580,737), describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now abandoned (see U.S. Pat. No. 5,567,588), describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-I Rev" now issued as U.S. Pat. No. 5,496,938 describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now abandoned (see U.S. Pat. No. 5,660,985), that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,647,459, and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing nucleic acid ligands to cytokines and the nucleic acid ligands so identified and produced. In particular, RNA sequences are provided that are capable of binding specifically to IFN-gamma, IL-4, IL-10, and TNFα. In addition, DNA sequences are provided that are capable of binding specifically to RANTES. Specifically included in the invention are the RNA ligand sequences shown in Tables 3, 4, 7, 8, 10, and 12 (SEQ ID NOS:7–73; 79–85; 189–205; 209–255).

Further included in this invention is a method of identifying nucleic acid ligands and nucleic acid ligand sequences to a cytokine comprising the steps of (a) preparing a candidate mixture of nucleic acids, (b) contacting the candidate mixture of nucleic acids with a cytokine, (c) partitioning between members of said candidate mixture on the basis of affinity to the cytokine, and (d) amplifying the selected molecules to yield a mixture of nucleic acids enriched for nucleic acid sequences with a relatively higher affinity for binding to the cytokine.

Further included in this invention is a method of identifying nucleic acid ligands and nucleic acid ligand sequences to a cytokine selected from the group consisting of IFN-gamma, IL-4, IL-10, TNFα, and RANTES comprising the steps of (a) preparing a candidate mixture of nucleic acids, (b) contacting the candidate mixture of nucleic acids with said cytokine, (c) partitioning between members of said candidate mixture on the basis of affinity to said cytokine, and (d) amplifying the selected molecules to yield a mixture of nucleic acids enriched for nucleic acid sequences with a relatively higher affinity for binding to said cytokine.

More specifically, the present invention includes the RNA ligands to IFN-gamma, IL-4, IL-10, and TNFα identified according to the above-described method, including those ligands shown in Tables 3, 4, 7, 8, 10, and 12 (SEQ ID NOS:7–73; 79–185; 189–205; 209–255). Also included are RNA ligands to IFN-gamma, IL-4, IL-10, and TNFα that are substantially homologous to any of the given ligands and that have substantially the same ability to bind IFN-gamma, IL-4, IL-10, and TNFα and inhibit the function of IFN-gamma, IL-4, IL-10, and TNFα. Further included in this invention are nucleic acid ligands to IFN-gamma, IL-4, IL-10, and TNFα that have substantially the same structural form as the ligands presented herein and that have substantially the same ability to bind IFN-gamma, IL-4, IL-10, and TNFα and inhibit the function of IFN-gamma, IL-4, IL-10, and TNFα.

The present invention also includes modified nucleotide sequences based on the nucleic acid ligands identified herein and mixtures of the same.

DETAILED DESCRIPTION OF THE INVENTION

This application describes high-affinity nucleic acid ligands to cytokines identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991 entitled Nucleic Acid Ligands now issued as U.S. Pat. No. 5,475, 096, U.S. patent application Ser. No. 07/931,473, filed Aug. 17, 1992, entitled Methods for Identifying Nucleic Acid Ligands, now U.S. Pat. No. 5,270,163, (see also WO91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The nucleic acid ligands described herein can be complexed with a lipophilic compound (e.g., cholesterol) or attached to or encapsulated in a complex comprised of lipophilic components (e.g., a liposome). The complexed nucleic acid ligands can enhance the cellular uptake of the nucleic acid ligands by a cell for delivery of the nucleic acid ligands to an intracellular target. U.S. patent application Ser. No. 08/434,465, filed May 4, 1995, entitled "Nucleic Acid Ligand Complexes," which is incorporated in its entirety herein, describes a method for preparing a therapeutic or diagnostic complex comprised of a nucleic acid ligand and a lipophilic compound or a non-immunogenic, high molecular weight compound.

The methods described herein and the nucleic acid ligands identified by such methods are useful for both therapeutic and diagnostic purposes. Therapeutic uses include the treatment or prevention of diseases or medical conditions in human patients. Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to cytokines described herein may specifically be used for identification-of the cytokine proteins.

SELEX provides high affinity ligands of a target molecule. This represents a singular achievement that is unprecedented in the field of nucleic acids research. The present invention applies the SELEX procedure to the specific target. In the Example section below, the experimental parameters used to isolate and identify the nucleic acid ligands to cytokines are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic acid ligands after SELEX has been performed. The '624 application, entitled Nucleic Acid Ligands to HIV-RT and HIV-I Rev now issued as U.S. Pat. No. 5,496,938, is specifically incorporated herein by reference.

This invention includes the SELEX process for identification of nucleic acid ligands of cytokines. Cytokines are a diverse group of small proteins that mediate cell signaling/communication. Cytokines include immune/hematopoietins (e.g., EPO, GM-CSF, G-CSF, LIF, OSM, CNTF, GH, PRL, IL-2, IL-3, IL-4, IL-5, IL-6, IL-7, IL-9, IL-10, IL-12), interferons (e.g., IFNα, IFNβ, IFN-gamma), TNF-related molecules (e.g., TNFα, IFNβ, gp$^{39}$ (CD40-L), CD27-L, CD30-L, NGF), and chemokines (e.g, PF4, PBP, groα, MIG, ENA-78, MIP1α, MIP1β, MCP-1, I-309, HC14, C10, RANTES, IL-8, MIP-1). In one embodiment, cytokines are derived from T-lymphocytes.

In the present invention, SELEX experiments were performed in order to identify RNA with specific high affinity for the cytokines IFN-gamma, IL-4, IL-10, hTNFα, and RANTES from degenerate libraries containing 30 or 40 random positions (40N for IFN-gamma, IL-4, IL-10 and RANTES; 30N for hTNFα) (Tables 1, 5, 9, 11, and 16). This invention includes the specific RNA ligands to IFN-gamma, IL-4, IL-10, and TNFα shown in Tables 3, 4, 7, 8, 10, and 12 (SEQ ID NOS:7–73; 79–185; 189–205; 209–255), identified by the methods described in Examples 1, 3, 5, 7, and 12. This invention further includes RNA ligands to IFN-gamma, IL-4, IL-10, and TNFα which inhibit the function of IFN-gamma, IL-4, IL-10, and TNFα. This invention further includes DNA ligands to RANTES which inhibit the function of RANTES. The scope of the ligands covered by this invention extends to all nucleic acid ligands of IFN-gamma, IL-4, IL-10, TNFα, and RANTES modified and unmodified, identified according to the SELEX procedure. More specifically, this invention includes nucleic acid sequences that are substantially homologous to the ligands shown in Tables 3, 4, 7, 8, 10, and 12 (SEQ ID NOS:7–73; 79–185; 189–205; 209–255). By substantially homologous it is meant a degree of primary sequence homology in excess of 70%, most preferably in excess of 80%. A review of the sequence homologies of the ligands of IFN-gamma, IL-4, IL-10, and TNFα shown in Tables 3, 4, 7, 8, 10, and 12 (SEQ ID NOS.:7–73; 79–185; 189–205; 209–255) shows that sequences with little or no primary homology may have substantially the same ability to bind IFN-gamma, IL-4, IL-10, and TNFα. For these reasons, this invention also includes nucleic acid ligands that have substantially the same structure and ability to bind IFN-gamma, IL-4, IL-10, and TNFα as the nucleic acid ligands shown in Tables 3, 4, 7, 8, 10, and 12 (SEQ ID NOS.:7–73; 79–185; 189–205; 209–255). Substantially the same ability to bind IFN-gamma, IL-4, IL-10, and TNFα means that the affinity is within one or two orders of magnitude of the affinity of the ligands described herein. It is well within the skill of those of ordinary skill in the art to determine whether a given sequence—substantially homologous to those specifically described herein—has substantially the same ability to bind IFN-gamma, IL-4, IL-10, and TNFα.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 9, 1993, entitled High Affinity Nucleic Acid Ligands Containing Modified Nucleotides, now abandoned (see U.S. Pat. No. 5,660,985), which is specifically incorporated herein by reference. Other modifications are known to one of ordinary skill in the art. Such modifications may be made post-SELEX (modification of previously identified unmodified ligands) or by incorporation into the SELEX process.

As described above, because of their ability to selectively bind IFN-gamma, IL-4, IL-10, hTNFα, and RANTES, the nucleic acid ligands to IFN-gamma, IL-4, IL-10, TNFα, and RANTES described herein are useful as pharmaceuticals. This invention, therefore, also includes a method of inhibiting cytokine function by administration of a nucleic acid ligand capable of binding to a cytokine.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention.

EXAMPLE 1

Experimental Prodedures for 2'-NH$_2$ AND 2'-F-Modified Ligands to IFN-gamma

This example provides general procedures followed and incorporated in Example 2 for the evolution of nucleic acid ligands to IFN-gamma.

A. Oligonucleotides

2'F modified CTP and UTP were prepared according to the method of Pieken et al., 1991. 2'NH$_2$ modified CTP and UTP were prepared according to the method of McGee et al., U.S. patent application Ser. No. 08/264,029, filed Jun. 22, 1994, which is incorporated herein by reference (see also McGee et al. 1995). DNA oligonucleotides were synthesized by Operon Technologies (Alameda Calif.).

B. SELEX

The SELEX procedure has been described in detail in U.S. Pat. No. 5,270,163 (see also Tuerk and Gold, 1990; Gold, et al., 1993). Three SELEX procedures were performed to evolve high affinity ligands to IFN-gamma. Each SELEX procedure utilized RNA pools containing pyrimidines modified at the 2' position as follows, 1) 2'F-CTP and 2'F-UTP referred to as 2'F, 2) 2'F-CTP and 2'NH$_2$-UTP referred to as 2'F/NH$_2$, and 3) 2'NH$_2$-CTP and 2'NH$_2$-UTP referred to as 2'NH$_2$. For each SELEX, the DNA template 40N7 was designed to contain 40 random nucleotides, flanked by 5' and 3' regions of fixed sequence (Table 1; SEQ ID NO:1). The fixed regions include DNA primer annealing sites for PCR and cDNA synthesis as well as the consensus T7 promoter region to allow in vitro transcription.

Single-stranded DNA primers and templates were synthesized and amplified into double-stranded transcribable templates by PCR. Preparation of the initial pool of RNA molecules involved PCR amplification of 1000 pmoles of single-stranded template (Table 1; SEQ ID NO: 1) and 2500 pmoles of both the 5'(5P7; SEQ ID NO:2)- and 3'(3P7; SEQ ID NO:3)-primers. These were incubated in a reaction mixture containing 50 mM KCl, 10 mM Tris-Cl (pH 8.3), 3 mM MgCl$_2$, 0.5 mM of each dATP, dCTP, dGTP, and dTTP. Taq DNA Polymerase (Perkin-Elmer, Foster City Calif.) at 0.1 U/µl was added and the reaction incubated at 97° C. for 3 min to denature the template and primers. Following the initial denaturing step, the reaction was cycled 10 times at 93° C. for 30 sec, 53° C. for 30 sec, and 72° C. for 1 min to denature, anneal, and extend, respectively, the primers and template. To get an accurate concentration of double-stranded PCR product for the initial round of SELEX, the PCR product was purified using QIAquick-spin PCR purification columns (QIAGEN Inc., Chatsworth Calif.) as specified by the manufacturer.

For in vitro transcription using modified nucleotides 200 pmoles (final concentration of 1 µM) of double-stranded DNA template was incubated in a reaction mixture containing 40 mM Tris-Cl (pH 8.0), 12 mM MgCl$_2$, 5 mM DTT, 1 mM spermidine, 0.002% Triton X-100, 4% PEG 8000, 0.5 µM α-$^{32}$P-ATP, 5 U/µl T7 RNA Polymerase (Davanloo, et al., 1984), and concentrations of other nucleotides as follows, 1) for the 2'F SELEX: 1 mM ATP and GTP, 3 mM 2'F-CTP and 2'F-UTP, 2) for the 2'F/NH$_2$ SELEX: 1 mM ATP, GTP, and 2'NH$_2$-UTP and 3 mM 2'F-CTP, and 3) for the 2'NH$_2$ SELEX: 1 mM ATP, GTP, 2'NH$_2$-CTP, and 2'NH$_2$-UTP. These incubations were performed in a 37° C. incubator for between 6 hrs and overnight. Typically the RNA was purified by gel purification and elution. To expedite the process, for rounds 11, 12, and 14–17 the RNA was purified using Bio-Spin 6 chromatography columns (Bio-Rad Laboratories, Hercules Calif.) according to manufacturer's specifications. To reduce background, the RNA was pre-filtered prior to all rounds of SELEX except rounds 1, 2, 4, 6, 14, and 16. The pre-filtration step involved bringing the RNA up to 200 µl in phosphate buffered saline (PBS), modified to contain 1 mM Mg$^{2+}$ ions, (138 mM NaCl, 2.7 mM KCl, 8.1 mM Na$_2$HPO$_4$, 1.1 mM KH$_2$PO$_4$, 1 mM MgCl$_2$, pH 7.4), (mPBS), and passing this RNA solution through three filter discs (0.45 µm, nitrocellulose/cellulose acetate, Millipore Corporation, Bedford, Mass.) pre-wetted with mPBS.

For initial binding, 1000 pmoles of RNA were incubated with human IFN-gamma protein in binding buffer, (mPBS plus 0.01% human serum albumin (HSA)), for 5–10 min at 37° C. to allow binding to occur. Human recombinant IFN-gamma used in this SELEX procedure was purchased from two different sources. The first three rounds of both the 2'F and 2'F/NH$_2$ SELEX were performed with protein obtained from Upstate Biotechnology, Lake Placid, N.Y. The subsequent rounds of these two SELEX procedures as well as the entire 2'NH$_2$ SELEX were performed with protein obtained from Genzyme Inc., Cambridge Mass. For each round of SELEX the concentration of RNA and protein was carefully chosen to provide optimum stringency. Increased stringency was obtained during rounds 8–13 of SELEX by adding NaCl to the binding buffer to bring the final chloride ion concentration up to 250 mM. Preliminary experiments had shown that IFN-gamma had a tendency to aggregate at high protein concentrations. To prevent the evolution of RNA species having an affinity for this aggregated IFN-gamma, beginning with round 4 of SELEX and for all subsequent rounds of the SELEX procedure, the binding mix was centrifuged at 16,000×g for 3 min in an eppendorf centrifuge before nitrocellulose filter partitioning. IFN-gamma/RNA complexes were separated from unbound RNA by nitrocellulose filter partitioning described below.

For nitrocellulose partitioning, the 2'F and 2'F/NH$_2$ SELEX procedures used 0.2 µm pore size pure nitrocellulose filters (Scleicher & Schuell, Keene, N.H.) for the first two rounds of SELEX. All subsequent rounds of these two SELEX procedures and the entire 2'NH$_2$ SELEX were performed with 0.45 µm pore size nitrocellulose/cellulose acetate mixed matrix filters (Millipore Corporation, Bedford Mass.). Filter discs were placed into a vacuum manifold and wetted with 5 ml of mPBS buffer. The IFN-gamma/RNA binding mix was aspirated through the filter discs which were immediately washed with 5 ml of mPBS buffer. To further increase stringency and reduce background for rounds 8–13, and 15, this washing step was modified to include washing of the filter discs with 15 ml 0.5M urea followed by 20 ml mPBS buffer. Bound RNA was isolated from filters by extraction in a solution of 400 µl phenol (equilibrated in Tris-Cl, pH 8.0)/300 µl 7M urea (freshly prepared). The filters were bathed in the phenol/urea solution at room temperature for 30 min and at 95° C. for 2 min. The RNA was phenol/chloroform extracted and ethanol precipitated with 20 mg tRNA.

The RNA was reverse transcribed into cDNA by addition of 50 pmoles DNA primer, 0.4 mM each of dNTPs, and 1 U/µl AMV reverse transcriptase (AMV RT) (Life Sciences, Inc., St. Petersburg, Fla.) in buffer containing 50 mM Tris-Cl (pH 8.3), 60 mM NaCl, 6 mM Mg(OAc)$_2$, 10 mM DTT. The reaction was incubated at 37° C. for 30 min then 48° C. for 30 min then 70° C. for 10 min, to ensure the melting of secondary structure present in the isolated RNA.

To begin a new round of SELEX, the cDNA was PCR amplified by addition of 250 pmoles of both the 5'(5P7; SEQ ID NO:2) and 3'(3P7; SEQ ID NO:3) primer in reaction conditions identical to those detailed above. The number of cycles of PCR required to amplify the cDNA was carefully calculated for each round of SELEX so that 250 pmoles double-stranded DNA template would be used to initiate the next round of SELEX.

C. Equilibrium Dissociation Constants (Kds)

The determination of equilibrium dissociation constants (Kds) for RNA pools was made subsequent to rounds 5, 8, 12, and 17 to monitor the progress of each SELEX. The Kds of RNA pools for mouse IFN-gamma (Genzyme Inc., Cambridge Mass.) were also determined after rounds 8 and 17. Kds were determined for individual ligands after cloning and sequencing of RNA pools and truncations (described below). Nitrocellulose filter binding was used to determine Kds as follows: filter discs were placed into a vacuum manifold and wetted with 5 ml of mPBS buffer. $^{32}$P-labeled-RNA was incubated with serial dilutions of IFN-gamma in binding buffer for 5–10 min at 37° C. to allow binding to occur. Binding mixes were centrifuged as described above to remove aggregates, aspirated through the filter discs, and then immediately washed with 5 ml mPBS buffer. The filter discs were dried and counted in a liquid scintillation counter (Beckmann Instruments, Palo Alto Calif.). Equilibrium dissociation constants were determined by least square fitting of the data points using the Kaleidagraph™ graphics program (Synergy Software, Reading Pa.). Many ligands and evolved RNA pools yield biphasic binding curves. Biphasic binding can be described as the binding of two affinity species that are not in equilibrium. Biphasic binding constants were calculated according to standard procedures. Kds were determined by least square fitting of the data points using the Kaleidagraph™ graphics program.

D. Cloning and Sequencing

After the 17th round of SELEX, RNA molecules were reverse transcribed to cDNA and made double-stranded by PCR amplification with primers containing recognition sites for the restriction endonucleases Hind III (Table 1; 5' primer 5P7H; SEQ ID NO:4) and Bam HI (Table 1; 3' primer 3P7B; SEQ ID NO:5). Using these restriction sites the DNA sequences were inserted directionally into the pUC19 vector. These recombinant plasmids were transformed into *Epicurian coli* JM109 competent cells (Stratagene, La Jolla Calif.). Plasmid DNA was prepared with the PERFECT-prep™ plasmid DNA kit (5 prime→3 prime, Boulder Colo.). Plasmid clones were sequenced using a PCR sequencing protocol (Adams, et al., 1991) using PCR sequencing primer pUC19F30 (SEQ ID NO:6).

E. Ligand Truncation

Boundary experiments were carried out to determine the minimal sequence necessary-for high affinity binding of the RNA ligands to IFN-gamma using end-labeled RNA. Prior to end-labeling, RNA transcribed with T7 RNA polymerase was gel purified by UV shadowing. The 5'-end of 20 pmoles of each RNA was dephosphorylated in a reaction mixture containing 20 mM Tris-Cl (pH 8.0), 10 mM $MgCl_2$ and 0.1 U/μl shrimp alkaline phosphatase (SAP), (U.S. Biochemical, Cleveland, Ohio) by incubating for 30 min at 37° C. Alkaline phosphatase activity was destroyed by incubating for 30 min at 70° C. RNA was subsequently 5'-end labeled in a reaction mixture containing 50 mM Tris-Cl (pH 7.5), 10 mM $MgCl_2$, 5 mM DTT, 0.1 mM EDTA, 0.1 mM spermidine, 0.75 μM γ-$^{32}$P-ATP and 1 U/μl T4 polynucleotide kinase (New England Biolabs, Beverly Mass.) by incubating for 30 min at 37° C.

3'-end-labeling of 20 pmoles of each RNA was performed in a reaction mixture containing 50 mM Tris-Cl (pH 7.8), 10 mM $MgCl_2$, 10 mM β-mercaptoethanol, 1 mM ATP, 0.9 μM (5'-$^{32}$P)pCp and 1 U/μl T4 RNA ligase (New England Biolabs, Beverly Mass.) by incubating for 18 hrs at 4° C. 5'- and 3'-end-labeled RNAs were gel band purified on a 12%, 8M urea, polyacrylamide gel. After partial alkaline hydrolysis of the end-labeled RNA by addition of $Na_2CO_3$ to a final concentration of 50 mM and incubation in a boiling water bath for 3 min, radiolabeled RNA ligands were incubated with IFN-gamma at three different protein concentrations, 1) 5-fold below the approximate Kd, 2) at the approximate Kd, and 3) 5-fold above the approximate Kd. Protein-bound RNA was separated by nitrocellulose partitioning. RNA truncates were analyzed on a high-resolution denaturing 12% polyacrylamide gel. To orient the sequences, a ladder of radioactively labeled ligands terminating with G-residues was generated by RNase T1 digestion of end-labeled RNA. The T1 digest was carried out in a reaction mixture containing 7M urea, 20 mM sodium citrate (pH 5.0), 1 mM EDTA and 5 units RNase T1 (Boehringer Mannheim, Indianapolis, Ind.),by incubating for 5 min at 50° C. Complementary single-stranded DNA oligonucleotides containing the sequence of the T7 promoter (5'-TAATACGACTCACTATAG-3'; fragment of SEQ ID NO:2) and the sequence of the truncated ligand were annealed to form a double-stranded template for transcription of each truncated ligand.

F. Receptor Binding Competitions

Human lung carcinoma cells (A549; ATCC) were plated in 24-well plates at a density of $5 \times 10^5$ cells/well in RPMI 1640 plus 10% fetal bovine serum (FBS) and incubated overnight or until confluent. The cells were washed 3 times with PBS. Growth media was replaced with 200 μl RPMI 1640 plus 0.2% human serum albumin/0.02% sodium azide/ 20 mM Hepes, pH 7.4 together with increasing amounts (20 pg/ml-100 ng/ml) of $^{125}$I-IFN-gamma (New England Nuclear) with or without an excess (200 fold) of unlabeled IFN-gamma. Incubations were carried out at 4° C. with shaking for 2 hrs. The cells were washed 2 times with cold PBS to remove free IFN and detached with 0.5% SDS. Cell-associated $^{125}$I-IFN-gamma was determined by measuring the radioactivity of the detached cells in a gamma counter. The data was corrected for nonspecific binding and the affinity of $^{125}$I-IFN-gamma was determined by Scatchard analysis of the binding data. Scatchard analysis suggests that there are high-affinity binding sites (Kd=20 pM) and low-affinity binding sites (Kd=0.5 nM). For competition with oligonucleotide, the cells were incubated for 2 hr at 4° C. as above with 30 pM $^{125}$I-IFN-gamma and increasing concentrations (1.01–500 nM) of competitor oligonucleotide. Cell-associated $^{125}$I-IFN-gamma was determined as above.

EXAMPLE 2

2'-$NH_2$ and 2'-F-Modified RNA Ligands to IFN-gamma

A. SELEX

Three libraries of RNAs modified at the 2' position of pyrimidines, 1) 2'F incorporating 2'F-CTP and 2'F-UTP, 2) 2'F/$NH_2$ incorporating 2'F-CTP and 2'$NH_2$-UTP and 3) 2'$N_2$ incorporating 2'$NH_2$-CTP and 2'$NH_2$-UTP were used in simultaneous SELEX protocols to generate a diverse set of high-affinity modified RNA ligands to human IFN-gamma. Each of these libraries contained between $10^{13}$–$10^{14}$ molecules with a variable region of 40 nucleotides The template and primers used for the SELEX and the conditions of the SELEX, as described in Example 1, are summarized in Tables 1 and 2, respectively.

B. RNA Sequences and Dissociation Constants

The random modified RNA pools bound human IFN-gamma with approximate Kds of greater than 0.7 μM. After 17 rounds of SELEX, the approximate Kds of the evolving pools had improved to, 1) 70 nM for the 2'F SELEX, 2) 115 nM for the 2'F/$NH_2$ SELEX, and 3) 20 nM for the 2'$NH_2$ SELEX. For mouse IFN-gamma, the approximate Kds of the RNA pools after 17 rounds of SELEX were 1) 410 nM for the 2'F SELEX, 2) 175 nM for the 2'F/$NH_2$ SELEX, and 3) 85 nM for the 2'$NH_2$ SELEX. These Kds did not shift further in subsequent rounds.

In order to determine to what extent the evolving pool was still random, PCR product from the final round of SELEX was sequenced as detailed above and found to be non-random. RNA from the 17th round was reverse transcribed, amplified and cloned. The sequences of 32 of the 2'F, 40 of the 2'NH$_2$, and 11 of the 2'F/NH$_2$ individual clones were determined (Table 3; SEQ ID NOS:7–65). The sequences were analyzed for conserved sequences and aligned by this criterion (Table 3). The 2'F sequences fell in to 2 groups with 9 orphan sequences. Group 1 2'F RNAs were the most abundant, representing 18 of 32 sequences, while group 2 2'F RNAs represented 5 of 32 sequences. The 2'NH$_2$ sequences fell into 2 groups with 25 of 40 2'NH$_2$ RNAs in group 1 and 15 of 40 2'NH$_2$ RNAs in group 2. The 2'F/NH$_2$ sequences were of a single group.

The Kds of individual RNAs within each group were determined by nitrocellulose filter binding as described above. The Kds were determined using either a monophasic or biphasic least squares fit of the data.

Minimal sequence requirements for high-affinity binding of the best clones were determined by 5' and 3' boundary experiments as described. The truncated RNAs were transcribed from double-stranded templates containing the T7 promoter and the truncated sequence. For those successful transcriptions, the Kd of the truncated ligand was determined. The sequence of the truncated ligands and their Kds, both for full-length and for the truncate (if determined) are shown in Table 4 (SEQ ID NOS:66–73).

C. Receptor Competition

Both full-length 2'NH$_2$ (2'NH$_2$ random, 2'NH$_{2-17}$, 2'NH$_{2-30}$) and 2'F (2'F random, 2'F-1, and 2'F-28) oligonucleotides were tested for their ability to inhibit receptor binding. This competition was targeted primarily to the high-affinity binding component using a concentration of $^{125}$I-IFN-gamma of 30 pM. At this concentration, neither the 2'NH$_2$ nor the 2'F random oligos showed inhibition, while varying degrees of inhibition were seen with the 4 clones tested. The 2'NH$_2$ ligand #30 (SEQ ID NO:72) was the best inhibitor and showed 50% inhibition at 10 nM.

EXAMPLE 3

Experimental Procedures for 2'-NH$_2$ and 2'-F-Modified Ligands to IL-4

This Example provides general procedures followed and incorporated in Example 4 for the evolution of nucleic acid ligands to IL-4.

A. Oligonucleotides

2'F modified CTP and UTP were prepared according to the method of Pieken et al., 1991. 2'NH$_2$ modified CTP and UTP were prepared according to the method of McGee et al., U.S. patent application Ser. No. 08/264,029, filed Jun. 22, 1994, now abandoned (See U.S. patent application Ser. No. 08/732,283) which is incorporated herein by reference (see also McGee et al. 1995). DNA oligonucleotides were synthesized by Operon Technologies (Alameda Calif.).

B. SELEX

The SELEX procedure has been described in detail in U.S. Pat. No. 5,270,163 (see also Tuerk and Gold, 1990; Gold, et al., 1993). Three SELEX procedures were performed to evolve high affinity ligands to IL-4. Each SELEX procedure utilized RNA pools containing pyrimidines modified at the 2' position as follows, 1) 2'F-CTP and 2'F-UTP referred to as 2'F, 2) 2'F-CTP and 2'NH$_2$-UTP referred to as 2'F/NH$_2$, and 3) 2'NH$_2$-CTP and 2'NH$_2$-UTP referred to as 2'NH$_2$. For each SELEX, the DNA template 40N8 was designed to contain 40 random nucleotides, flanked by 5' and 3' regions of fixed sequence (Table 5; SEQ ID NO:74). The fixed regions include DNA primer annealing sites for PCR and cDNA synthesis as well as the consensus T7 promoter region to allow in vitro transcription.

Single-stranded DNA primers and templates were synthesized and amplified into double-stranded transcribable templates by PCR. Preparation of the initial pool of RNA molecules involved PCR amplification of 1000 pmoles of single-stranded template and 2500 pmoles of both the 5' (5P8; SEQ ID NO:75) and 3' (3P8; SEQ ID NO:76) primers. These were incubated in a reaction mixture containing 50 mM KCl, 10 mM Tris-Cl (pH 8.3), 3 MM MgCl$_2$, 0.5 mm of each dATP, dCTP, dGTP, and dTTP. Tag DNA Polymerase (Perkin-Elmer, Foster City Calif.) at 0.1 U/µl was added and the reaction incubated at 97° C. for 3 min to denature the template and primers. Following the initial denaturing step, the reaction was cycled 7 times at 93° C. for 30 sec, 53° C. for 30 sec, and 72° C. for 1 min to denature, anneal, and extend, respectively, the primers and template. To get an accurate concentration of double-stranded PCR product for the initial round of SELEX, the PCR product was purified using QIAquick-spin PCR purification columns (QIAGEN Inc., Chatsworth Calif.) as specified by the manufacturer.

For in vitro transcription using modified nucleotides 200 pmoles (final concentration of 1 µM) of double-stranded DNA template was incubated in a reaction mixture containing 40 mM Tris-Cl (pH 8.0), 12 mM MgCl$_2$, 5 mM DTT, 1 mM spermidine, 0.002% Triton X-100, 4% PEG 8000, 0.5 µM α-$^{32}$P 2'OH ATP, 5 U/µl T7 RNA Polymerase (Davanloo, et al., 1984), and concentrations of other nucleotides as follows, 1) for the 2'F SELEX: 1 mM ATP and GTP, 3 mM 2'F-CTP and 2'F-UTP, 2) for the 2'F/NH$_2$ SELEX: 1 mM ATP, GTP, and 2'NH$_2$-UTP and 3 mM 2'F-CTP, and 3) for the 2'NH$_2$ SELEX: 1 mM ATP, GTP, 2'NH$_2$-CTP, and 2'NH$_2$-UTP. These incubations were performed in a 37° C. incubator for between 6 hrs and overnight. Typically the RNA was purified by gel purification and elution. To expedite the process for rounds 11, 12, and 14–17 the RNA was purified using Bio-Spin 6 chromatography columns (Bio-Rad Laboratories, Hercules Calif.) according to manufacturer's specifications. To reduce background, the RNA was pre-filtered prior to all rounds of SELEX except rounds 1, 2, 4, 6, 14, and 16. The pre-filtration step involved bringing the RNA up to 200 µl in phosphate buffered saline (PBS), modified to contain 1 mM Mg$^{2+}$ ions, (138 mM NaCl, 2.7 mM KCl, 8.1 mM Na$_2$HPO$_4$, 1.1 mM KH$_2$PO$_4$, 1 mM MgCl$_2$, pH 7.4), (mPBS), and passing this RNA solution through three filter discs (0.45 µm, nitrocellulose/cellulose acetate, Millipore Corporation, Bedford Mass.) pre-wetted with mPBS.

For initial binding, 1000 pmoles of RNA were incubated with human IL-4 protein in binding buffer, (mPBS plus 0.01% human serum albumin (HSA)), for 5–10 min at 37° C. to allow binding to occur. Human recombinant IL-4 used in this SELEX procedure was purchased from R & D Systems, Minneapolis Minn. For each round of SELEX the concentration of RNA and protein was carefully chosen to provide optimum stringency. Preliminary experiments had shown that IL-4 had a tendency to aggregate at high protein concentrations. To prevent the evolution of RNA species having an affinity for this aggregated IL-4, beginning with round 4 of SELEX and for all subsequent rounds of the SELEX procedure, the binding mix was centrifuged at 16,000×g for 3 min in an eppendorf centrifuge before nitrocellulose filter partitioning. IL-4/RNA complexes were separated from unbound RNA by nitrocellulose filter partitioning described below.

For nitrocellulose partitioning, the 2'F and 2'F/NH$_2$ SELEX procedures used 0.2 μm pore size pure nitrocellulose filters (Scleicher & Schuell, Keene N.H.) for the first two rounds of SELEX. All subsequent rounds of these two SELEX procedures and the entire 2'NH$_2$ SELEX were performed with 0.45 μm pore size nitrocellulose/cellulose acetate mixed matrix filters (Millipore Corporation, Bedford Mass.). Filter discs were placed into a vacuum manifold and wetted with 5 ml of mPBS buffer. The IL-4/RNA binding mix was aspirated through the filter discs which were immediately washed with 5 ml of mPBS buffer. To further increase stringency and reduce background for rounds 8–13, and 15, this washing step was modified to include washing of the filter discs with 15 ml 0.5 M urea followed by 20 ml mPBS buffer. Bound RNA was isolated from filters by extraction in a solution of 400 μl phenol (equilibrated in Tris-Cl, pH 8.0)/ 300 μl 7 M urea (freshly prepared). The filters were bathed in the phenol/urea solution at room temperature for 30 min and at 95° C. for 2 min. The RNA was phenol/chloroform extracted and ethanol precipitated with 20 μg tRNA.

The RNA was reverse transcribed into cDNA by addition of 50 pmoles DNA primer, 0.4 mM each of dNTPs, and 1 U/μl AMV reverse transcriptase (AMV RT) (Life Sciences, Inc., St. Petersburg Fla.) in buffer containing 50 mM Tris-Cl (pH 8.3), 60 mM NaCl, 6 mM Mg(OAc)$_2$, 10 mM DTT. The reaction was incubated at 37° C. for 30 min then 48° C. for 30 min then 70° C. for 10 min, to ensure the melting of secondary structure present in the isolated RNA.

To begin a new round of SELEX, the cDNA was PCR amplified by addition of 250 pmoles of both the 5' (5P8; SEQ ID NO:75) and 3' (3P8; SEQ ID NO:76) primer in reaction conditions identical to those detailed above. The number of cycles of PCR required to amplify the cDNA was carefully calculated for each round of SELEX so that 250 pmoles double-stranded DNA template would be used to initiate the next round of SELEX.

C. Equilibrium Dissociation Constants (Kds)

The determination of equilibrium dissociation constants (Kds) for RNA pools was made subsequent to rounds 5, 8, 12, and 17 to monitor the progress of each SELEX. The Kds of RNA pools for mouse IL-4 (R & D Systems, Minneapolis Minn.) were also determined after round 8. Kds were determined for individual ligands after cloning and sequencing of RNA pools and truncations (described below). Nitrocellulose filter binding was used to determine Kds as follows: filter discs were placed into a vacuum manifold and wetted with 5 ml of mPBS buffer. $^{32}$P-labeled-RNA was incubated with serial dilutions of IL-4 in binding buffer for 5–10 min at 37° C. to allow binding to occur. Binding mixes were centrifuged as described above to remove aggregates, aspirated through the filter discs, and then immediately washed with 5 ml mPBS buffer. The filter discs were dried and counted in a liquid scintillation counter (Beckmann Instruments, Palo Alto Calif.). Equilibrium dissociation constants were determined by least square fitting of the data points using the Kaleidagraph™ graphics program (Synergy Software, Reading Penn.). Many ligands and evolved RNA pools yield biphasic binding curves. Biphasic binding can be described as the binding of two affinity species that are not in equilibrium. Biphasic binding constants were calculated according to standard procedures. Kds were determined by least square fitting of the data points using the Kaleidagraph™ graphics program.

D. Cloning and Sequencing

After the 17th round of SELEX, RNA molecules were reverse transcribed to cDNA and made double-stranded by PCR amplification with primers containing recognition sites for the restriction endonucleases Hind III (Table 5; 5' primer 5P8H; SEQ ID NO:77) and Bam HI (Table 5; 3' primer 3P8B; SEQ ID NO:78). Using these restriction sites the DNA sequences were inserted directionally into the pUC19 vector. These recombinant plasmids were transformed into *Epicurian coli* JM109 competent cells (Stratagene, La Jolla Calif.). Plasmid DNA was prepared with the PERFECTprep™ plasmid DNA kit (5 prime→3 prime, Boulder Colo.). Plasmid clones were sequenced using a PCR sequencing protocol (Adams, et al., 1991 using PCR sequencing primer pUC19F30 (SEQ ID NO:6)).

E. Ligand Truncation

Boundary experiments were carried out to determine the minimal sequence necessary for high affinity binding of the RNA ligands to IL-4 using end-labeled RNA. Prior to end-labeling, RNA transcribed with T7 RNA polymerase was gel purified by UV shadowing. The 5'-end of 20 pmoles of each RNA was dephosphorylated in a reaction mixture containing 20 mM Tris-Cl (pH 8.0), 10 mM MgCl$_2$ and 0.1 U/μl shrimp alkaline phosphatase (SAP), (United States Biochemical, Cleveland Ohio) by incubating for 30 min at 37° C. Alkaline phosphatase activity was destroyed by incubating for 30 min at 70° C. was subsequently 5'-end labeled in a reaction mixture containing 50 mM Tris-Cl (pH 7.5), 10 mM MgCl$_2$, 5 mM DTT, 0.1 mM EDTA, 0.1 mM spermidine, 0.75 μM γ-$^{32}$P-ATP and 1 U/μl T4 polynucleotide kinase (New England Biolabs, Beverly Mass.) by incubating for 30 min at 37° C.

3'-end-labeling of 20 pmoles of each RNA was performed in a reaction mixture containing 50 mM Tris-Cl (pH 7.8), 10 mM MgCl$_2$, 10 mM β-mercaptoethanol, 1 mM ATP, 0.9 μM (5'-$^{32}$P)pCp and 1 U/μl T4 RNA ligase (New England Biolabs, Beverly Mass.) by incubating for 18 hrs at 4° C. 5'- and 3'-end-labeled RNAs were gel band purified on a 12%, 8M urea, polyacrylamide gel. After partial alkaline hydrolysis of the end-labeled RNA by addition of Na$_2$CO$_3$ to a final concentration of 50 mM and incubation in a boiling water bath for 3 min, radiolabeled RNA ligands were incubated with IL-4 at three different protein concentrations, 1) 5-fold below the approximate Kd, 2) at the approximate Kd, and 3) 5-fold above the approximate Kd. Protein-bound RNA was separated by nitrocellulose partitioning. RNA truncates were analyzed on a high-resolution denaturing 12% polyacrylamide gel. To orient the sequences, a ladder of radioactively labeled ligands terminating with G-residues was generated by RNase T1 digestion of end-labeled RNA. The T1 digest was carried out in a reaction mixture containing 7M urea, 20 mM sodium citrate (pH 5.0), 1 mM EDTA and 5 units RNase T1 (Boehringer Mannheim, Indianapolis Ind.) by incubating for 5 min at 50° C. Complementary single-stranded DNA oligonucleotides containing the sequence of the T7 promoter (5'-TAATACGACTCACTATAG-31'; fragment of SEQ ID NO:75) and the sequence of the truncated ligand were annealed to form a double-stranded template for transcription of each truncated ligand.

F. Receptor Competition

Human T-cell lymphoma cells (H-9; ATCC) were cultured in suspension in RPMI 1640+10% FCS. Cells were washed two times with PBS and resuspended (5.0×10$^5$ cells) in 200 μl media containing RPMI 1640+0.02% human serum albumin/0.2% Na azide/20 mM HEPES, pH 7.4 for 2 hr at 4° C. in 1.5 ml polypropylene tubes (Eppendorf, W. Germany) with various amounts of $^{125}$I-rIL-4 in the presence or absence of a 200-fold excess of unlabeled cytokine. Following incubation, the tubes were spun (150×g, 5 min, 4° C.) and the supernatant was aspirated. The cell pellet was resuspended in 200 μl RPMI-HSA. 100 μl aliquots were centrifuged through a cushion of an equal volume of phthalate oils (dibutyl/dioctyl, 1:1 v/v). The tube was rapidly frozen in dry ice/ethanol and the tip containing the cell pellet was cut off and placed in a vial for gamma counting. The data was corrected for nonspecific binding and the affinity of $^{125}$I-IL-4 was determined by Scatchard analysis. For competition with oligonucleotide, or neutralizing antibody (R & D Systems), the cells were incubated for 2 hr at 4° C. as above with 0.7 nM $^{125}$I-IL-4 and increasing concentrations (0.01–500 nM) of competitor oligonucleotide. Cell-associated $^{125}$I-IL-4 was determined as above.

EXAMPLE 4

2'-NH$_2$ and 2'-F-modified RNA Ligands to IL-4

A. SELEX

Three libraries of RNAs modified at the 2' position of pyrimidines, 1) 2'F incorporating 2'F-CTP and 2'F-UTP, 2) 2'F/NH$_2$ incorporating 2'F-CTP and 2'NH$_2$-UTP and 3) 2'NH$_2$ incorporating 2'NH$_2$-CTP and 2'NH$_2$-UTP were used in simultaneous SELEX protocols to generate a diverse set of high-affinity modified RNA ligands to human IL-4. Each of these libraries contained between $10^{13}$–$10^{14}$ molecules with a variable region of 40 nucleotides. The template and primers used for the SELEX and the conditions of the SELEX, as described in Example 3 are summarized in Tables 5 and 6, respectively.

B. RNA Sequences and Dissociation Constants

The random modified RNA pools bound human IL-4 with approximate Kds of greater than 20 μM. After 17 rounds of SELEX, the approximate Kds of the evolving pools had improved to, 1) 30 nM for the 2'F SELEX, and 2) 55 nM for the 2'F/NH$_2$ SELEX. Binding curves performed on 2'NH$_2$ RNA from an earlier round had shown an approximate Kd of 100 nM, however, difficulties with background reduction in this SELEX led to an apparent Kd after round 17 of 1 μM. It was felt that despite this "masking" due to background, the high affinity unique sequence 2'NH$_2$ RNAs were still in the pool after round 17. These Kds did not shift further in subsequent rounds. The RNA pools after 8 rounds of SELEX did not bind mouse IL-4, while there was a significant improvement in binding after 8 rounds for the human protein (data not shown).

In order to determine to what extent the evolving pool was still random, PCR product from the final round of SELEX was sequenced as detailed above and found to be non-random. RNA from the 17th round was reverse transcribed, amplified, and cloned. The sequences of 41 of the 2'F, 57 of the 2'NH$_2$, and 30 of the 2'F/NH$_2$ individual clones were determined (Table 7; SEQ ID NOS:79–177). The sequences were analyzed for conserved sequences and aligned by this criterion (Table 7). The 2'F sequences fell into a single group representing 29 of 41 sequences. The remaining 12 clones were categorized as orphans due to their lack of sequence homology with the primary group or to each other. The 2'NH$_2$ sequences fell into 2 distinct groups of sequences. Group 1 which represented 21 of 57 sequences were shown to bind to IL-4. The other group, representing 35 of 57 sequences were shown to bind to nitrocellulose filters. The presence of such a large number of nitrocellulose filter binding RNAs was not a surprise as these sequences were cloned from a pool with high background binding. These nitrocellulose binding RNAs are identified by the presence of a direct repeat of the sequence GGAGG. A single orphan 2'NH$_2$ sequence was also found. The 2'F/NH$_2$ sequences were more heterogeneous with sequences falling into 3 groups. RNAs in group 1 and 2 bound to IL-4, while the 3rd group bound to nitrocellulose filters. The clones in the nitrocellulose filter binding group also contained a single or repeat of the sequence GGAGG. It should be noted that this sequence is also found in the 3'-fixed region (underlined in Table 7).

The Kds of individual RNAs within each group were determined by nitrocellulose filter binding as described in Example 3 above. The Kds were determined using a monophasic least squares fit of the data.

Minimal sequence requirements for high-affinity binding of the best clones were determined by 5' and 3' boundary experiments as described in Example 3. The truncated RNAs were transcribed from double-stranded templates containing the T7 promoter and the truncated sequence. For those successful transcriptions, the Kd of the truncated ligand was determined. The sequence of the truncated ligands and their Kds, both for full-length and for the truncate (if determined) are shown in Table 8 (SEQ ID NOS:178–185).

C. Receptor Competition

Full-length 2'NH$_2$ (2'NH$_2$ random, 2'NH$_2$-29), 2'F (2'F random, 2'F-9) and 2'F/NH$_2$ (2'F/NH$_2$ random, 2'F/NH$_2$-9 and 2'F/NH$_2$-28) oligonucleotides were tested for their ability to inhibit receptor binding. Neither the 2'NH$_2$, 2'F, or 2'F/NH$_2$ random oligos showed inhibition, while varying degrees of inhibition was seen with the clones tested. At an IL-4 concentration of 0.7 nM the 2'F/NH$_2$ ligand-9 was the best competitor for receptor binding and showed 50% inhibition at approximately 40 nM. The competition by this oligonucleotide was similar to that seen by a neutralizing antibody to IL-4.

EXAMPLE 5

Experimental Procedures for 2'-F Modified Ligands to IL-10

This Example provides general procedures followed and incorporated in Example 6 for the evolution of nucleic acid ligands to IL-10.

A. Materials

DNA sequences were synthesized by using cyanoethyl phosphoramidite under standard solid phase chemistry. 2'-F CTP and 2'-F UTP were purchased from United States Biochemicals. Human IL-10 was bought from either Bachem or R&D Systems. Neutralizing anti-human IL-10 monoclonal antibody, murine IL-10 and ELISA detection kit for human IL-10 were purchased from R & D Systems.

B. SELEX

Five nmoles of synthetic DNA template, that was purified on an 8% polyacrylamide gel under denaturing conditions were amplified by four cycles of polymerase chain reaction (PCR). The PCR products were transcribed in vitro by T7 RNA polymerase (1000 U) in 1 mL reaction consisting of 2 mM each of ATP and GTP, 3 mM each of 2'-F CTP and 2'-F UTP, 40 mM Tris-HCl (pH 8.0), 12 mM MgCl$_2$, 1 mM Spermidine, 5 mM DTT, 0.002% Triton X-100 and 4% polyethylene glycol (w/v) for 10–12 hr. The full-length transcription products (SEQ ID NO:186) were purified on 8% denaturing polyacrylamide gels, suspended in TBS buffer [100 mM Tris-HCl, (pH 7.5) 150 mM NaCl] (binding buffer), heated to 70 ° C., chilled on ice, then incubated with IL-10 at 37 ° C. for 10 min. The RNA-protein mixture was filtered through a pre-wet nitrocellulose filter then washed with 5 mL of the binding buffer. Bound RNAs were eluted from the filter and recovered by ethanol precipitation. The RNA was reverse transcribed by avian myeloblastosis virus reverse transcriptase (Life Sciences) at 48° C. for 45 min with 5'-GCCTGTTGTGAGCCTCCTGTCGAA-3' primer (Table 9; SEQ ID NO:188). The cDNA was amplified by PCR (with 5' and 3' primers (SEQ ID NOS: 187–188)) and the resulting DNA template was transcribed to obtain RNA for the next round of selection. During the course of SELEX, the concentration of IL-10 was decreased gradually from 5 μM to 500 nM to progressively increase selective pressure. The selection process was repeated until the affinity of the enriched RNA pool for IL-10 was substantially increased. At that point, cDNA was amplified by PCR with primers that introduced BamH1 and Hind III restriction sites at 5' and 3' ends, respectively. PCR products were digested with BamHI and Hind III and cloned into pUC 18 that was digested with the same enzymes. Individual clones were screened and sequenced by standard techniques.

C. Determination of Equilibriuim Dissociation Constants ($K_d$)

Internally-labeled RNA transcripts were prepared by including [γ-$^{32}$P]ATP in T7 RNA polymerase transcription reactions. Full-length transcripts were purified on 8% denaturing polyacrylamide gels to ensure size homogeneity. Gel-purified RNA was diluted to a concentration of ~5 nM in TEM buffer, heated to 80 °C. then chilled on ice to facilitate secondary structure formation. RNA concentrations were kept lower than 100 pM in binding reactions. Briefly, equal amounts of RNA were incubated with varying amounts of IL-10 in 50 μL of TEM buffer for 10 min at 37 °C. RNA-protein mixtures were passed through pre-wet nitrocellulose filters (0.2μ) and the filters were immediately washed with 5 mL of binding buffer. Radioactivity retained on filters was determined by liquid scintillation counting. The quantities of RNA bound to filters in the absence of protein was determined and used for background correction. The percentage of input RNA retained on each filter was plotted against the corresponding log protein concentration. The nonlinear least square method to obtain the dissociation constant ($K_d$).

D. Sandwich ELISA

Sandwich ELISA was carried out by using commercially available ELISA kit for quantitative determination of hIL-10 (from R&D systems) according to manufacturer's instructions. Varying amounts of RNA 43, random pool RNA and anti-hIL-10 monoclonal antibody (from R&D Systems) were incubated with 125 pg/mL hIL-10 at room temperature for 10 min before added to microtiter wells.

EXAMPLE 6

2'-F-Modified RNA Ligands to IL-10

Under nitrocellulose filter binding conditions the random sequence pool that was used to initiate the SELEX experiment did not show detectable binding to IL-10 as high as 5 μM concentration. However, after twelve rounds of affinity selection the enriched pool exhibited improved affinity, and further selection beyond the 12th round had no effect on increasing the affinity for IL-10. Table 10 (SEQ ID NOS:189–205) shows the sequences identified from the 12th round pool. Sequences are grouped into three classes based on the sequence similarity. The 5' part in the variable 40 nucleotide region of most sequences in class I has sequence complementarity to the 3' part, suggesting that such sequences can fold into a stemloop structure.

Individual clones were initially screened for their ability to bind IL-10 at 250 nM concentration. The results show that 20–40% of input individual RNAs was bound to IL-10 at 250 nM. Based on preliminary screening, sequence 43 (SEQ ID NO:189) was chosen as a representative ligand to carry out in section B below.

The Kd of sequence 43 for binding to IL-10 is 213 nM. The ligand 43, on the other hand does not bind to other cytokines such as interferon g and IL-4, indicating the specificity of SELEX-derived RNA sequence. Human IL-10 (hIL-10) and mouse IL-10 (mIL-10) have high degree of sequence homology at the cDNA and amino acid level (73% amino acid homology) and hIL-10 has been shown to active on mouse cells. However, ligand 43 does not bind to mIL-10 with high affinity.

B. RNA in IL-10 ELISA

An anti-IL10 monoclonal antibody that neutralizes the receptor binding is commercially available. The R&D systems' Quantikine Immunoassay kit is based on 96 well microtiter plates coated with the neutralizing antibody to capture hIL-10. The ELISA was used to investigate whether RNA binds at or near the neutralizing antibody binding site on IL-10. RNA 43, similar to the random pool RNA (used as a control) did not show any inhibition of IL-10 binding to anti-IL-10 antibody on the plate (data not shown). These data suggest that the evolved RNA ligand does not bind to the site at or near that recognized by the neutralizing antibody. The soluble anti-IL10 that was used in the assay as a control behaved as expected, competing for binding with the same antibody on the solid phase.

EXAMPLE 7

Experimental Procedures for Ligands to hTNFα

This Example provides general procedures followed and incorporated in Examples 8–11 for the evolution of nucleic acid ligands to hTNFα.

A. Materials

Recombinant human TNFα (hTNFα) was purchased from Genzyme (Cambridge, Mass.) or R&D Systems (Minneapolis, Minn.), recombinant murine TNFα (mTNFα), recombinant human TNFβ (hTNFβ), and soluble human TNF receptor 2 (sTNF-R2) were purchased from R&D Systems. Acetylated, and nuclease free bovine serum albumin (BSA), ligase and restriction enzymes were from new England Biolabs (Beverly, Mass.). AMV reverse transcriptased were from Life Sciences (St. Petersburg, Fla.). RNasin ribonuclease inhibitor, and Taq DNA polymerase was from Promega (Madison, Wis.). Ultrapure nucleotide triphosphates were from Pharmacia (Piscataway, N.J.). $^{125}$I-TNFα, α-$^{32}$P-ATP, and γ-$^{32}$P-ATP were from DuPont NEN Research Products (Boston, Mass.). U937 cells were from ATCC (catalog number CRL1593). Oligonucleotides were obtained from Operon, Inc. (Alameda, Calif.). Nitrocellulose/cellulose acetate mixed matrix (HA), 0.45 μm filters were from Millipore (Bedford, Mass.). Chemicals were at least reagent grade and purchased from commercial sources.

B) SELEX

The SELEX procedure has been described in the SELEX Patent Application (see also Tuerk and Gold, 1990; Gold, et al., 1993). The starting RNA contained 30 random nucleotides, flanked by 5' and 3' constant regions for primer annealing sites for cDNA synthesis and PCR amplification (Table 11; SEQ ID NO:206). The single stranded DNA molecules were converted to double stranded by PCR amplification. PCR conditions were 50 mM KCl, 10 mM Tris-HCl, pH9, 0.1% Triton X-100, 3 mM MgCl$_2$, 0.5 mM of each dATP, dCTP, dGTP, and dTTP, 0.1 units/μl Tag DNA polymerase and 1 nM each of the 5' and 3' primers. Transcription reactions were done with about 5 μM DNA template, 5 units/μl T7 RNA polymerase, 40 mM Tris-HCl (pH8), 12 mM MgCl$_2$, 5 mM DTT, 1 mM spermidine, 0.002% Triton X-100, 4% PEG 8000, 2–4 mM each 2'OH NTP, and 0.25 μM α-$^{32}$P-ATP (800 Ci/mmole). For 2'F modified transcripts, 2'F-CTP and 2'F-UTP were used instead of 2'OH-CTP and 2'OH-UTP. Two different SELEX experiments were done. In the first SELEX experiment, SELEX-A, the protein was immobilized onto nitrocellulose filters and the RNA ligands were partitioned by capture to the immobilized protein. Briefly, hTNFα was spotted on a nitrocellulose filter (Millipore, HA 0.45 μm) and following 5 min air drying over filter paper, the nitrocellulose filter was incubated in a 24-well microtiter plate with 1–2×10$^{-6}$ M radiolabeled RNA for 30 min at room temperature in 500 μl binding buffer (BB=10 mM Tris-HCl, pH 7.5, 150 mM NaCl, 1 mM EDTA, 0.02% acetylated BSA, 0.02% ficol, and 0.02% PVP). The filter was then washed three times for 10 minutes each in 1.5 ml BB without BSA. Binding and washing was done under rigorous agitation. The RNA bound to the immobilized protein was recovered by phenol/urea extraction and was then reverse transcribed into cDNA by AMV reverse transcriptase at 48° C. for 60 min in 50 mM Tris-HCl pH8.3, 60 mM NaCl, 6 mM Mg(OAc)$_2$, 10 mM DTT, 50 pmol DNA primer-1 (Table 11), 0.4 mM each of dATP, dCTP, dGTP, and dTTP, and 1 unit/μl AMV RT. The cDNA was then PCR amplified and used to initiate the next SELEX cycle as described above. In the second SELEX experiment, SELEX-B, the binding buffer was Dulbecco's Phosphate-Buffered Saline (DPBS) with calcium and magnesium (Life Technologies, Gaithersburg, Md., Cat. No 21300-025) and the protein-RNA complexes were partitioned by filtering through nitrocellulose/cellulose acetated mixed matrix, 0.45 μm pore size filter disks (Millipore, Co., Bedford, Mass.). Nitrocellulose filter bound RNA was recovered by phenol/urea extraction. The partitioned RNA was then reverse transcribed and PCR amplified as above and used to initiate the next SELEX cycle.

C. Determination of Equilibrium Dissociation Constants

To partition the protein-RNA complexes, the binding reactions were filtered through nitrocellulose/cellulose acetated mixed matrix, 0.45 μm pore size filter disks (Millipore, Co., Bedford, Mass.). For filtration, the filters were placed onto a vacuum manifold and wetted by aspirating 5 ml of DPBS. The binding reactions were aspirated through the filters and following a 5 ml wash, the filters were counted in a scintillation counter (Beckmann). Nitrocellulose partitioning was used for SELEX and for determining the equilibrium dissociation constants of RNA ligands to TNFα. RNA ligands to TNFα bind monophasically.

To obtain the equilibrium dissociation constants of RNA ligands to TNFα the binding reaction:

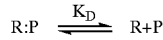

R=RNA
P=Protein
K$_D$=dissociation constant
is converted into an equation for the fraction of RNA bound at equilibrium:

$$q=(f/2R_T)(P_T+R_T+K_D-((P_T+R_T+K_D)^2-4P_TR_T)^{1/2})$$

q=fraction of RNA bound
P$_T$=total protein concentration
R$_T$=total RNA concentration
f=retention efficiency of RNA-protein complexes
The average retention efficiency for RNA-TNFα complexes on nitrocellulose filters is 0.1–0.2.

The K$_D$s were determined by least square fitting of the data points using the software Kaleidagraph (Synergy Software, Reading, Pa.).

D. Cloning and Sequencing

RT-PCR amplified cDNA from the last round of SELEX was cloned between BamHI and HindIII restriction sites of pUC18 plasmid (Vieira et al., 1982, Gene 19: 259–268) in MC1061 E. coli (Casadaban et al., 1980, J Mol Biol 138: 179–207). Sequencing was done using PCR products as templates with a commercially available kit (Promega, Madison Wis.).

E. Receptor Binding Competition Assay

A receptor binding competition assay was used to determine the bioactivity of the RNA ligands. $^{125}$I labelled hTNFα at 0.1 nM was incubated in 50 μl of binding medium (PBS with 0.5 mM Mg$^{++}$, 0.2% BSA, 0.02% sodium azide, 1U/μl RNasin) for 15 min at 4° C. with serially diluted competitors at 10$^{-4}$ to 10$^{-11}$M, and 1×10$^4$/μl U937 cells. Duplicate aliquots were subsequently removed, centrifuged through 2:1 dibutyl-phthalate:dinonyl-phthalate mixture to separate free and bound $^{125}$I labelled hTNFα, and the radioactivity in the pellet was measured on a gamma counter. Nonspecific binding was determined by inclusion of a 200-fold molar excess of unlabeled TNF.

The inhibition constants (Ki) of the RNA ligands were determined by a nonlinear regression analysis of the data using standard techniques. To obtain Ki values the concentration of TNF receptor was assumed to be 3.4×10$^{-11}$M and the K$_D$ of the TNFα-TNFR interaction of 0.1 nM.

F. Boundary Determination

For 3' boundary determination, the 6A RNA ligand was 5' end labeled with γ-$^{32}$P-ATP using T4 polynucleotide kinase. 5' boundaries were established using 3' end labeled ligand with α-$^{32}$P-pCp and T4 RNA ligase. After partial alkaline hydrolysis, the radiolabeled RNA ligand was incubated with hTNFα at 5, 25, and 125 nM, and the protein bound RNA was isolated by nitrocellulose partitioning. The RNA truncates were analyzed on a high resolution denaturing polyacrylamide gel. An alkaline hydrolysis ladder and a ladder of radioactively labeled ligands terminated with G-residues, generated by partial RNase T1 digestion, were used as markers.

EXAMPLE 8

RNA Lignads to hTFNα

A. Pre-SELEX Characterization

Nitrocellulose filter binding could not detect any interaction of hTNFα with random RNA even at high protein concentrations. The binding curves were completely flat even up to 10 μM hTNFα and RNA up to 1μM and the estimated dissociation constant (K$_D$) is greater than 10$^{-3}$M. No buffer conditions were found that improved the interaction of hTNFα and random RNA.

To determine whether hTNFα was binding any RNA at all we used a more sensitive technique similar to northwestern probing (Bowen et al., 1980). This technique was used in various studies of protein nucleic acid interaction and aided in the cloning of various DNA binding proteins (Singh et al., 1988). This experiment showed clearly that some random RNA can bind to hTNFα. RNA binding occurred only when the filter was previously spotted with hTNFα and then dried, but not if the filter was spotted with hTNFα and then placed wet in the incubation chamber. The RNA was binding only on the filters carrying hTNFcc but not on filters carrying BSA possibly because, either not enough BSA was immobilized on the filter or the BSA present in the incubation mix was competing for available BSA-specific RNA ligands.

B. SELEX

Two independent SELEX experiments (A and B) were initiated with pools of randomized RNA containing about $10^{14}$ unique molecules. The starting RNA and the PCR primer sequences are shown in Table 11 (SEQ ID NOS:206–208).

In the A-SELEX, the protein was immobilized on a nitrocellulose filter by drying. The protein containing filter was incubated in BB (see Example 7) with labeled RNA, then washed, autoradiographed and the bound RNA was recovered by phenol-urea extraction. For the first round of A-SELEX about 1,000 pmoles of hTNFα monomer was used and the RNA concentration was at $2\times10^{-6}$M. For the subsequent 14 rounds, two different filters containing about 500 and 100 pmoles of hTNFα monomer were incubated in the same chamber containing amplified RNA from the previous round at about $2\times10^{-6}$M. Only the RNA from the high protein filter was carried to the next round. A steady increase in the signal to noise ratio was observed and at round 15 the signal retained on the 500- and 100-pmole protein filters was 170- and 35-fold above background respectively. For comparison, in the first round the signal was only about 3-fold above background. RNA from round 15 had a higher affinity for hTNFα with an estimated Kd of $5\times10^{-5}$ M, representing a possible 100 fold improvement over the random RNA. To increase the stringency of the selection, we carried 8 more rounds using filters with about 10 and 1 pmole of hTNFα. For all these subsequent rounds, except for round 20, the RNA from the 1 pmole hTNFα filters was carried to the next round. Because of high background, at round 20 we used the RNA from the 10 pmoles hTNFα filter of round 19. The signal to noise ratio for these subsequent rounds became worse at each round but nevertheless the affinity of the evolved RNA continued to improve with estimated final Kd of $7\times10^{-7}$M, which represents two additional orders of magnitude improvement. In the final round, we could detect signal with 10-fold shorter exposure time was detected, and with 100-fold less hTNFα on the filter.

In parallel with the stringent phase of A-SELEX, RNA from round 15 of the A-SELEX was evolved using B-SELEX conditions (see below) for 6 more rounds. We designated this as C-SELEX. The affinity of the evolved population at the end of C-SELEX was similar to the round 23 population of A-SELEX with approximate Kd=$4\times10^{-7}$ M.

The evolved RNA from round 23 had not only improved affinity for hTNFα but it was also specific (Table 13). Binding could be detected only with hTNFα.

In the B-SELEX experiment, binding reactions were set in 25–50 μl and after 10 min incubation at 37° C. it was filtered through a 0.45 μm HA nitrocellulose filter. For the first round of the B-SELEX, the RNA and protein were at about $4\times10^{-5}$M each. Under these conditions only 0.1% of the input RNA was retained on the filter. This was not surprising since the hTNFα-random-RNA interaction is very weak with a Kd too high to measure and probably in the $10^{-3}$M range. Subsequent rounds were set similar to the first round. By round 8, the background binding of the RNA to the nitrocellulose filters was very high.

B. RNA Sequences and Affinities

RT-PCR amplified cDNA from round 23 of A-SELEX and round 6 of C-SELEX were cloned and sequenced as described in Example 7. 37 clones were sequenced from A-SELEX and 36 cloned from C-SELEX. From the total of 73 sequences, 48 were unique (Table 12). A unique sequence is defined as one that differs from all others by three or more nucleotides. Of the 47 unique clones, 18 clones could bind to hTNFα with Kd better than 1 μM (Table 12). The best ligand, 25A (SEQ ID NO:233), binds with affinity dissociation constant of about 40 nM. If it is assumed that the random RNA binds with a dissociation constant of greater than $10^{-3}$M, then the affinity of 25A is at least four to five orders of magnitude better than the starting pool.

Using sequence alignment and conserved predicted secondary structure, 17 out of 18 clones that bind hTFNα could be assigned into two classes.

The members of the class II can be folded in stem-loop structures with internal bulges and asymmetric loops. Linear sequence alignment did not reveal any significant conserved sequences.

C. Specificity of RNA Ligands to TNF

We tested the specificity of the evolved pool of round 23 of A-SELEX against human TNFα, human TNFβ and murine TNFα. The evolved pool is highly specific for human TFRα and specificity ratios are shown in Table 13.

EXAMPLE 9

Inhibition of hTNFα Binding to Cell Surface Receptors

To test the ability of the TNFα ligands to competitively inhibit the binding of hTNFα to its cell surface receptor, the U937 cells were used to screen several hTNFα ligands. The observed Kis are listed in Table 14. The data show that several ligands can competitively inhibit binding of hTNFα to its cell surface receptors while random RNA cannot. Ligand 25A has the highest potency with a Ki of 21 nM. This Ki value is only 6 fold worse than the Ki observed with the sTNF-R2 under the same experimental conditions.

EXAMPLE 10

Effect of 2'F Pyrimidine Modification on the Binding and Inhibitory Activities of the hTNFα Ligands Transcripts containing 2'F modified pyrimidines are resistant to RNase degradation. To obtain ligands with improved stability we tested the effect of 2'F pyrimidine modification on the binding and inhibitory activity of several hTNFα ligands. The results summarized in Table 15 show that some of the ligands retained binding activity when are modified with 2'F pyrimidines but in general the modified ligands bind worse than the unmodified counterparts. Class II ligands are in general more tolerant of the 2'F pyrimidine modification. Most of the ligands that retained binding after the 2'F pyrimidine modification lose their inhibitory activity. Only the 2'F pyrimidine modification of the most abundant ligand, 6A, did not affect its binding and inhibitory activities.

EXAMPLE 11

Experimental Procedures for DNA Ligands to RANTES

This example provides general procedures followed and incorporated in Example 12 for the evolution of nucleic acid ligands to RANTES.

A) Materials

Recombinant human RANTES was purchased from Genzyme (Cambridge, Mass.). Taq DNA polymerase was Perkin Elmer (Norwalk, Conn.). T4 polynucleotide kinase was purchased from New England Biolabs (Beverly, Mass.). Ultrapure nucleotide triphosphates were purchased form Pharmacia (Piscataway, N.J.). Affinity purified streptavidin (Cat. No 21122) was from Pierce (Rockford, Ill.). Oligonucleotides were obtained from Operon, Inc. (Alameda, Calif.). Nitrocellulose/cellulose acetate mixed matrix (HA), 0.45 μm filters were purchased form Millipore (Bedford, Mass.). Chemicals were at least reagent grade and purchased from commercial sources.

B) SELEX

The SELEX procedure has been described in detail in the SELEX Patent Applications. The DNA template contained 40 random nucleotides, flanked by 5' and 3' constant regions for primer annealing sites for PCR (Table 16; (SEQ ID NOS:256–258). Primer 3G7 (SEQ ID NO:258) has 4 biotin residues in its 5' end to aid in the purification of single stranded DNA (ssDNA). For the first round, 105 pmoles of synthetic 40N7 ssDNA were 5' end labelled using T4 polynucleotide kinase in a 25 μl reaction containing 70 mM Tris-HCl pH 7.6, 10 mM MgCl$_2$, 5 mM DTT, 39.5 pmoles of γ-$^{32}$P-ATP (3000 Ci/mmol), and 16 units kinase, for 1 h at 37° C. The kinased DNA was then purified on an 8% polyacrylamide, 7M urea, denaturing gel and then mixed with gel purified unlabeled 40N7 to achieve about 5,000 cpm/pmol specific activity. To prepare binding reactions, the DNA molecules were incubated with recombinant RANTES in Hanks' Balanced Salt Solution (HBSS) without calcium and magnesium (Life Technologies, Gaithersburg, Md., Cat. No 14175) containing 0.01% human serum albumin. Two SELEX experiments were performed, one with normal salt concentration and the other with 300 mM NaCl. The high salt concentration was achieved by adding additional NaCl to the HBSS. Following incubation at room temperature for 30 minutes the protein-DNA complexes were partitioned from unbound DNA by filtering through HA nitrocellulose 0.45 μm. Nitrocellulose filter bound DNA was recovered by phenol/urea extraction. The partitioned DNA was PCR amplified in 50 mM KCl, 10 mM Tris-HCl, pH9, 0.1% Triton X-100, 3 mM MgCl$_2$, 1 mM of each dATP, dCTP, dGTP, and dTTP, with 0.1 units/μl Taq DNA polymerase. The 3G7 and 5G7 primers were present at 2 μM. The 5G7 primer was 5'-end labeled before use described above. To purify ssDNA, the PCR product was ethanol precipitated and then reacted with affinity purified streptavidin at a molar ratio 1:10 DNA to streptavidin in 10 mM Tris-HCl pH 7.5, 50 mM NaCl, 1 mM EDTA, 0.05% sodium azide. Following 30 incubation at room temperature, equal volume of 100% formamide tracking dye was added and the strands were denatured by incubating at 85° C. for 1.5 min. The denatured strands were then electophoresed in an 8% polyacrylamide, 7M urea gel and the nonshifted band was excised and purified from the crushed gel. The purified ssDNA was then used for the next SELEX cycle.

EXAMPLE 12

DNA Ligands to RANTES a) SELEX

To generate DNA ligands for RANTES, two SELEX experiments were performed, one with 150 mM and the other with 300 mM NaCl. The high salt was used in order to avoid precipitation of the RANTES-DNA complexes that occurs at the lower salt concentration. The SELEX at 300 mM salt was prematurely terminated because of high background. The SELEX conditions and results for each round of the 150 mM salt SELEX are summarized in Table 17. The starting pool contained 1.8×10$^{15}$ (2,940 pmoles) of DNA for the 150 mM salt SELEX. The starting K$_D$ values of the random DNA were 3×10$^{-6}$M. After 19 rounds of SELEX the evolved pools bound with a K$_D$ of 20 nM. This represents about 150 fold improvement.

TABLE 1

| 40N7 TEMPLATES AND PRIMERS: | SEQ ID NO. |
|---|---|
| 40N7 ssDNA Template: | |
| 5' GGGAGGACGAUGCGG [-40N-] CAGACGACUCGCCCGA 3' | 1 |
| SELEX PCR Primers: | |
| 5P7: | |
| 5' TAATACGACTCACTATAGGGAGGACGATGCGG 3' | 2 |
| 3P7: | |
| 5' TCGGGCGAGTCGTCTG 3' | 3 |
| Cloning PCR Primers: | |
| 5P7H: | |
|      Hind III | |
| 5' CCGAAGCTTAATACGACTCACTATAGGGAGGACGATGCGG 3' | 4 |
| 3P7B: | |
|      Bam HI | |
| 5' GCCGGATCCTCGGGCGAGTCGTCTG 3' | 5 |
| PCR Sequencing Primer: | |
| pUC19F30: | |
| 5' AGTCACGACGTTGTAAAACGACGGCCAGTG 3' | 6 |

TABLE 3

| | SEQ ID NO. |
|---|---|
| a) IFN-gamma 2'F Sequences | |
| 5'-GGGAGGACGAUGCGG(40N)CAGACGACUCGCCCGA-3' | 1 |
| 40N | |
| GROUP 1 (18 clones) | |
| #1, 2, 5, 11, 12, 15, 18, 21, 26, 32, 35 ACACCGUUAAUCUGAGGCCCUGUCCUAUUCCUUCACGCCU | 7 |
| #3   ACACCGUUAGUCUGAGGCCUUGUCCUAUUCCUUCACGCCU | 8 |
| #10  ACACCUUUAAUCUGAGGCCCUGUCCUAUUCCUUCACGCCU | 9 |
| #22  ACACCUUGAAUCUGAGGCCCUGUCCUAUUCCUUCACGCCU | 10 |
| #29  ACACCGUUAAUCUGAGGCCCUGUCCUAUUCCUCCACGCCU | 11 |
| #31  ACACCGUAGAUCUGAGGCCCUGUCCUAUUCCUCCACGCCU | 12 |
| #19  ACACCGUUAAUCUGAGGCCCUGUCC AUUCCUUCACGCCU | 13 |
| #13  ACACCGUUAAACUGAGGCCCUGUCCUAUUCCUUCACGCCU | 14 |
| GROUP 2 (5 clones) | |
| #27  AACACCCCCGGUCUGACGCUUGUUCCGAAUUCCUCCACCGU | 15 |
| #8   GAACACCCCCGGUCUGACGCUUGUUCCGAAUUCCUCCACCGU | 16 |
| #33  AACACC CCGGUCUGACGCUUGUUCCGAAUUCCUCCACCGU | 17 |
| #34  AACACCCCCGGUUUGACGCUUGUUCCGAAAUCCUCCACCGU | 18 |
| #36  AACACCCCCGGUCUGACGCUUGUUCCG AAUCCUCCACCGU | 19 |
| ORPHANS (9 clones) | |
| #4   GGUUCCUGUUCUACUUUCUAAUUAUCCGCACCUCCUCCU | 20 |
| #6   UGGAGUUUUAAUCUUACUUCCUACUCUUGCUCCACUGGGU | 21 |
| #7   GAUUCAUUUUGAUCUUUCUUUCUCUUAUCCCGCUGUGCCU | 22 |
| #23  AUUCCUUUUUCCUUUCUCUUUUCUGACCGACUGAUCCGCCU | 23 |
| #25  UAAUCUACACUUAUAUUUUUUUUCUUUUUCUUUCCACCCAUCGU | 24 |
| #28  AGGGUUGGGAGGGGUCCUUCUUUUCGUCUGCGUGGACCGU | 25 |
| #16  CAUCCCUAGAGCAGCCAGCCGGAAAGAAGUCACGCCUGCU | 26 |
| #17  UAGUGACCGUCAGGUAGGUGGGUUAGGCCAUUACGUACGU | 27 |
| #30  GUGCCAACAAUGGAGGUCGGGUUAGGUAAGCCAACGGGU | 28 |
| b) IFN-gamma 2'NH₂ Sequences | |
| 5'-GGGAGGACGAUGCGG(40N)CAGACGACUCGCCCGA-3' | 1 |
| 40N | |
| GROUP 1 (25 clones) | |
| #7              UAGUAGCGCGAUAUAGCG CUGGUAGGGUUGCCGGUGGAU | 29 |
| #B4,B5,B6       UAGUAGCGCGAUAUAGCG CUGGUAGGGUAGCCGGUG AU | 30 |
| #8              UUGUAGCGCGAUAUAGCG CUGGUAGGGUUGCCGGUGGAU | 31 |
| #B23            UGGUAGCGCGAUAUAGCG CUGGUAGGGUAGCCGGUG AU | 32 |
| #17,24,B3,B10   UGGUAGCGCGAUAUAGCG CUGGUAGGGUUGCCGGUG AU | 33 |
| #33             UUGUAGCGCGAUAUAGCG CUGGUAGGGUUGCCGGUG AU | 34 |

TABLE 3-continued

| | | SEQ ID NO. |
|---|---|---|
| #31 | UGGUAGCGCGAUAUAGCG CUGGUAGGGUUGCCGGUGGGU | 35 |
| #B7 | UUGUAGCGCGAUAUAGCG CUGGCAGGGUUGCCGGUGGGU | 36 |
| #11 | UGGCAGCGCGAGAUAGCG CUGGUAGGGUUGCCGGUGGAU | 37 |
| #B13 | UGGUAGCGCGACAUAGCG CUGGUAGGGUUGCCGGUG AU | 38 |
| #6,14 | AAGUGGUGAUCCCAUCUAGGGGUCGGUUGGGUCGACGGUG | 39 |
| #23 | UGUGUGGGGUGCCAUAUAACC CCGGUUGGGUUGACGGUGU | 40 |
| #13,15,18,22,B8 | UAGUGCUCACAGAGC GGUUGGGUAGCCGGUGGAUGCGGU | 41 |
| #25 | UGUGGUGCAAUCUAAGCACCGGUUGGGUAGUUCGGUGGCU | 42 |
| #12 | AGGCUCAAAAGGC C GGUUGGGUUAGGUAACUGUGUGCGGU | 43 |
| GROUP 2 (15 clones) | | |
| #16 | UAUGGUGGGUUUACGCGAGAGUAAGGGUCGCGUGGU | 44 |
| #29 | ACGUAUGGUGGGUUCGUAGUAUUGGGCUCGUAGCGUGGGU | 45 |
| #30 | CAGGUAAUUACAUGAAGGUGGGUUAGGUACUUUCAGGGU | 46 |
| #B9,B22 | UAGGUAAUUACAUGAAGGUGGGUUAGGUACUUUCAGGGU | 47 |
| #B12 | CAGUAAAUUCGGUAGGUGGGUUAGGUAGGAUCGUGAGGGU | 48 |
| #35 | UAUGGUGGGUUGCACGUAUUAAGGGACGUACAUCUGUGCU | 49 |
| #B14 | UAUAGGUAACUAUCAGGUGGGUAGUCGGUGGAAACGGGCUGUUGGU | 50 |
| #32 | UACAGGUGGGUCGUGGAUAAUUGGGCACGCUCUAUCUCCU | 51 |
| #B16 | CACUAGGUGGGUCGUGGUUGUUGGGCACGUAACUUCGCGU | 52 |
| #B24 | UACUAGGUGGGUCGUGGUUGUUGGGCACGUAACUUCGCGU | 53 |
| #34 | ACGUGGCCUUAGAUAGGCAGGUGGGUUAGGCAUAUUCAGU | 54 |
| #10 | UUCGCGGCCUAAUUAAAGGCAGGAGGGUUAGGCAUUGCU | 55 |
| #B2 | UGACUACGCCUGUAGUAGGUCGGGUUAGG CAUUGGGCGU | 56 |
| #B11 | UGCGCAAUUGCGCAGGUCGGGUUAGGUAUCUGGGUAGCU | 57 |
| c) IFN-gamma 2'F/NH$_2$ Sequences | | |
| 5'-GGGAGGACGAUGCGG(40N)CAGACGACUCGCCCGA-3' | | 1 |
| 40N | | |
| GROUP 1 (11 clones) | | |
| #3 | UUCAGAGGGUAGGUAAGUGGGAGGAAAAAUGCCGUAUCGCCU | 58 |
| #4 | AGGUAAGAGGGAGGGACCUUCCAGUGAAUGUGCGCGUGGU | 59 |
| #14 | AGGCCUGUGGUGAGGAUUGUGGGUGGUUGGCCACGCGCGU | 60 |
| #32 | UCCAAAGAGGGUGGUUGUGGGUGGCACUAAGGUACCGCGU | 61 |
| #2 | UAUUCGUAAGGCCAGAGCUGCGGGUGGGACCUCCGGCCU | 62 |
| #3,A8,13 | CCAUAGUGGGUGGGUUUGGAGUGGAAUAGUGCCGAGCGU | 63 |
| #15,23,33 | UGCACAUGAGGGUGGUGUGGGAGGAAACGUGACGCAUGGU | 64 |
| #1 | UUCCGUCCGUGGGAUAGGUUUGUGGGAUGUACCGGCUGGU | 65 |

TABLE 4

| Truncated IFN-gamma Ligands | SEQ ID NO. |
|---|---|
| 2'F | |
| #1 (Kd = 6.8/320 nM full-length; Kd = 4.4/716 nM truncate)<br>5'-gggaggacgaugcggACACCGUUAAUCUGAGGCCCUGUCCUAUUCCUUCACGCCUcaga-3' | 66 |
| #6 (Kd = 3.2/314 nM full-length)<br>5'-GUUUUAAUCUUACUUCCUACUCUUGCUCCACUGGGUcagacgacuc-3' (orphan) | 67 |
| #16 (Kd = 9.3/232 nM full-length)<br>5'-gggaggacgaugcggCAUCCCUAGAGCAGCCAGCCGGAAAGAAGUCACGCCUGCUca-3' (orphan) | 68 |
| #27 (Kd = 8.8/384 nM full-length)<br>5'-gggaggacgaugcggAACACCCCCGGUCUGACGCUUGUUCCGAAUUCCUCCACCGUcagacgac-3' | 69 |
| #28 (Kd = 35 nM full-length; Kd = 53 nM truncate)<br>5'-gggaggacgaugcggAGGGUUGGGAGGGGUCCUUCUU-3' (orphan) | 70 |
| 2'NH$_2$ | |
| #17 (Kd = 1.8/750 nM full-length; Kd = 12.4 nM truncate)<br>5'-gggaggacgaugcggUGGUAGCGCGAUAUAGCGCUGGUAGGGUUGCCGGUG-3' | 71 |
| #30 (Kd = 2.7/103 nM full-length; Kd = 11 nM truncate)<br>5'-gggaggacgaugcggCAGGUAAUUACAUGAAGGUGGGUUAGGUA-3' | 72 |
| 2'F/NH$_2$ | |
| #3 (Kd = 106 nM full-length; Kd = 119 nM truncate)<br>5'-(g)ggacgaugcggUUCAGAGGGUAGGUAAGUGGGAGGAAAAAUGCCGUAUCG-3' | 73 |

TABLE 5

| | SEQ ID NO. |
|---|---|
| 0N8 TEMPLATES AND PRIMERS | |
| 40N8 ssDNA Template<br>5' GGGAGACAAGAATAAACGCTCAA[-40N-]TTCGACAGGAGGCTCACAACAGGC 3' | 74 |
| SELEX PCR Primers: | |
| 5P8:<br>5' TAATACGACTCACTATAGGGAGACAAGAATAAACGCTCAA 3' | 75 |
| 3P8:<br>5' GCCTGTTGTGAGCCTCCTGTCGAA 3' | 76 |
| Cloning PCR Primers: | |
| 5P8H:<br>    Hind III<br>5' CCG<u>AAGCTT</u>TAATACGACTCACTATAGGGAGACAAGAATAAACGCTCAA 3' | 77 |
| 3P8B:<br>    Bam HI<br>5' GCC<u>GGATCC</u>GCCTGTTGTGAGCCTCCTGTCGAA 3' | 78 |
| PCR Sequencing Primer: | |
| pUC19F30:<br>5' AGTCACGACGTTGTAAAACGACGGCCAGTG 3' | 6 |

TABLE 7

| | SEQ ID NO. |
|---|---|
| a) IL-4 2'F Sequences | |
| 5'-GGGAGACAAGAAUAAACGCUCAA(40N)UUCGACAGGAGGCUCACAACAGGC-3' | 74 |

40N

GROUP 1 (29 clones)

| | | | |
|---|---|---|---|
| #2 | CUAUGGGGAGCCACAUU | AACGGCAAUAAAUCAUUACGAC | 79 |
| #3 | CUAUGGGGAGCCACAUUU | AACGGCUAUAAAAAACAUUACGAC | 80 |
| #6 | CUCGGGAGCCAGAGUAAC | AACGGCAUUAUAUAAUUUACU | 81 |
| #7,8,11,16 | UCCCACCGGGUGCCACGGUUUA | AACGGCUUAAUAUGAAU | 82 |
| #12 | GUCUGACUAUUGGGGCGCCACAAUAUC | AACGGCUGUAC | 83 |
| #17 | UCCCACCGGGUGCCACGGUUUA | AACGGCUUAAUAUUUACU | 84 |
| #19 | GUCUUCCAUGGGGAGCCACAUU | AACGGCGCAAUACUGAAC | 85 |
| #22,27,34,40 | CUCGGGAGCCAGAGUAAC | AACGGCACUAUAUAAUUUUACU | 86 |
| #26 | CUAUGGGGAGCCACAUUU | AACGGCAAUAAAUCAUUACGAC | 87 |
| #28 | AGUGGGGAGCCACACUAA | AACGGCAUAUUGACAUCGUCCC | 88 |
| #31 | UCUCCUCAUGGGGCGCCACAUGGUUUUAACGGCAUAUCACU | | 89 |
| #32 | CUAUGGGGAGCCACAUUU | AACGGCUAUAAAUCAUUACGAC | 90 |
| #35 | ACUGGGGAGCCACAGAUUU | AACGGCGCAUAUGAGUUGAGC | 91 |
| #39 | CUCUCACUGGGGAGCCACAGUUUUA | AACGGCAAGGGAGA | 92 |
| #41 | CAUCAGAUGGGGUGCCACAUCAUCA | AACGGCUAUAUA | 93 |
| #44 | ACUGGGGAGCCACAGAUUU | AACGGCACAUAUGAUUGAGC | 94 |
| #42 | AACGGCUGUAACAAACAAGGUGGGGGGCCACACCAG | AGCGGC | 95 |
| #9,15,1,33,46 | ACGGCUGUAACAAACAAGGUGGGGGGCCACACAGAGCGGGUUCGAC | | 96 |
| #25 | ACGGCUGUGACAAACAAGGUGGGGGGCCACACAGAGCGGG | | 97 |

ORPHANS (12 clones)

| | | |
|---|---|---|
| #4 | AUAGCAGAGCCCAUGGCGGGAGGGAGGAUUGUGGUGGAA | 98 |
| #13 | CAUCGACGGACCAGAGGUAGUGGGGGGGAUGGGAUGCCCG | 99 |
| #14 | ACCUAACAUCUUACCAUAUUCAAUUUACAUUACACACUAU | 100 |
| #18 | GCUGCCCAAGGAAUUUAACUUGGACCGCGAUCUGGAGUC | 101 |
| #21 | AGGAGCGCCAUGAAGCAAAGGGAGGAUUGUGGUGGAAGGC | 102 |
| #23 | CCGUAUUAACACUUAUUUUACAAUUUUUUCAUA | 103 |
| #24 | GGUACGACCAAGGAAUGUGGGUGGAAGAGGGUGCCGUACC | 104 |
| #30 | GACGAACGACCACGGGAUGGGUGGGCAAAUAGGGAUGCCG | 105 |
| #38 | GCUAACCCGUACAAAUUUUCUUUUUCAUUUUCAUCACUA | 106 |
| #43 | CUCGGGAGCCAGAGUAACAACGGCACUAUAUAAUUUUACC | 107 |
| #47 | CGACCCGACCAAGGGUAGGCAUGUGGGGGGGUGCCGGG | 108 |
| #48 | UCCGAACAUGGGGUGCCACAAAAACGGCUAUUAUCACUAU | 109 |

TABLE 7-continued

| | SEQ ID NO. |
|---|---|
| b) IL-4 2'NH₂ Sequences | |
| 5'-GGGAGACAAGAAUAAACGCUCAA(40N)UUCGACAGGAGGCUCACAACAGGC-3' | 74 |

40N

GROUP 1 (21 clones)

| | | | |
|---|---|---|---|
| #12 | GGACUGG UGAGCCACG | UAUA CGGUCUUAGGGGCUUGGGCG | 110 |
| #27 | CCUUGUGG GGAGCCACG | UAUA CGGCCAUAGCAUACCGCAA | 111 |
| #29 | GAGCUGG UGAGCCACG | UAUA CGGCCUUAGGGGCUUGGGCG | 112 |
| #B31 | GAGCUGG UGAGCCACG | UAUA CGGUCUUAGGGGCUUGGGCG | 113 |
| #17 | GUAUUGG GGAGCCACAU | UACAACGGCACAGGCAACCAGGG | 114 |
| #31 | GUGCUGG UGAGCCACGC | AUA CGGUCUUAGGGGCUUGAGCG | 115 |
| #B14,B19 | UAAAUGG AGAGCCACAC | UA A CGGCGUAUGAAAACACUCA | 116 |
| #B16,B17 | UCACAAGCACCCUUGG GGAGCCACA | UUAA CGGCCUAGGC | 117 |
| #B26 | AUGG AGAGCCACA | UUAA CGGCAGCAUAUCACAGUAGGAA | 118 |
| #B8 | UGUGG GGAGCCACAG | UUAA CGGCUUCAACUGAUUAGAA | 119 |
| #B24 | AGAUUUAAAGUAUUUGG GGAGCCACA | UCAA CGGCAUUGUG | 120 |
| #B29 | UGACUGAACGAUGGUAUUUGG AGAGCCACA | UCAA CGGCAAU | 121 |
| #22 | CAGAUGGUAUCUAGUGG AGAGCCACA | UCAA CGGCGCAGA | 122 |
| #B5 | CGAUAGUAUACACAUGAUGAUGG GGAGCCACG | UGUA CGGC | 123 |
| #B18,B20 | CGAUGG AGCGCCACAUCGCUAUAACGGCAUUUAACAAAAU | | 124 |
| #B33,B34 | GCGGUCUGAUUGAGCCACCG | UGGA GGGUACGUGGAGGGA | 125 |
| #6* ACAAUUUCACACAGAAACAGCUAUGACCAUGAUUACGCCA | | | 126 |
| | AGCUUUGG GGAGCCACA | UAUAACGGCAUGAUCAAAUAUAG | 127 |

ORPHAN (1 clone)

| | | |
|---|---|---|
| #32 AUACAAUGUGGUUGAAGCUACCUCCCACUCGUAGUGGGCC | | 128 |

NITROCELLULOSE FILTER BINDERS (35 clones)

| | | |
|---|---|---|
| #1,B4 | CCGUAGCCUCCAGCGGAACGCGGAGGGUACGUGGAGGGG | 129 |
| #2,3,24,25,26,36,B9,B15,B22 CCGUAGCCUCCAGCGGAAUGCGGAGGGCACGUGGAGGGG | | 130 |
| #5 | GAGCCUCCGUGAAUGACGUGGAGGCACGC GGAGGGGAA | 131 |
| #8 | UCGAUACUACUCCUGGAGAAAAGGAGGACCGU GGAGGA | 132 |
| #10 | UCGAUACUACUCCUGGAGAAAAGGAGGAUCGU GGAGGA | 133 |
| #11,B6 | GCGGUCUGAUUGAGCCUCCGUGGAGGGUACGUGGAGGGA | 134 |
| #18 | AGGGUGGAUUGU GGAGGAAUGAGUUGUCUAUGGACUCCA | 135 |
| #19 | UCGAUACUACUCCUGGAGAAAAGGAGGAUCGU GGAGGAA | 136 |
| #28 | CCGAUACUACUCCUGGAGAAAAGGAGGAUCGU GGAGGAA | 137 |
| #30 | GGGAGGAUAGU GGAGGAAGAGCGUGUAAUAAUGUUACGA | 138 |
| #34 | UCGUAGCCUCCAGCGGAAUGCGGAGGGCACGUGGAGGGG | 139 |
| #35 | UCGAUACUACUCCUGGAGAAAAGGAGGAUCGU GGAGGAA | 140 |
| #B3 | CCGCAGCCUCCAGCAAUGCGGAGGGCACGUGGAGGGG | 141 |

TABLE 7-continued

|     |     | SEQ ID NO. |
| --- | --- | --- |
| #B7 | GAGCCUCCGAGAAUGACGUGGAGGGUACGUGGAGGGGUA | 142 |
| #B11 | CCGUAGCCUCCAGCGGAACGCGGAGGGCACGUGGAGGGG | 143 |
| #B12 | UGCCGAGAGGAGGGCUGA GGAGGACGCGGCAUUAAGUGA | 144 |
| #B13 | UCGAUACUACUCCUGGAGAAAAGGAGGAUCGU GGAGGAU | 145 |
| #B23 | GAGCCUCCGAGAAUGACGUGGAGGGCACGUGGAGGGGAA | 146 |
| #B25 | UGCUGAGAGGAGGGCUGA GGAGGACACGGCAGUAUGAGA | 147 |
| #B27 | ACGUAGCCUCCAGCGGAAUGCGGAGGGCACGUGGAGGGG | 148 |
| #B28 | GCGGUCUGAUCGAGCCUCCGUGGAGGGUACGUGGAGGGA | 149 |
| #B30 | GCGGUCUGAUUGAGCCUCCGUGGAGGGCACGUGGAGGGA | 150 |
| #B32 | UGCCGAGAGGAGGGCUGA GGAGGACACGGCAGUAUGUAA | 151 |
| #B36 | CCGUAGCCUCCAGCGGAAUGUGGAGGGCACGUGGAGGGG | 152 |
| #9  | AAGGUGGGUCGU GGAGGAAUGAGCUCGCUCCCAGCUAA | 153 | c) IL-4 2'F/NH$_2$ Sequences

5'-GGGAGACAAGAAUAAACGCUCAA(40N)UUCGACAGGAGGCUCACAACAGGC-3'    74

40N

GROUP 1 (7 clones)

| #9 | AGAGUGCAGGUCUGGGGCGCCACA | AUUACA ACGG CAAUAA | 154 |
| --- | --- | --- | --- |
| #19 | GUCUUCCAUGGGGAGCCACAUUA ACGGCGCAAUACUGAAC | | 155 |
| #13 | CUCGGGAGCCAG AGUAACAACGGCACUAUAUAAUUUUAC | | 156 |
| #25 | AGAGCCGUUUUGGGGACCCAC AGUA ACGGGUUUAUGGUA | | 157 |
| #8,10 | GUCGGAGCGAUGGAGAGCCACG AUAU ACGGUCUGUGCGC | | 158 |
| #41 | AGUAACGUGGGGAGCCACACGU AAU ACGGCACUAA | | 159 |

GROUP 2 (11 clones)

| #16 | GGUACGA CCAAG GAAUGUGGGUGGAAG AGGGCGCCGUACC | 160 |
| --- | --- | --- |
| #28 | GAUCCUGCGACGCCA GGGGUGGAU AGGGGGAAGGGAGCGG | 161 |
| #2  | GACGAACGA CCAAG GGACGGGUGGGCAAAU AGGGAUGCCG | 162 |
| #11,22,29,30,44,45 | GGUACGA CCAAG GAAUGUGGGUGGAAG AGGGUGCCGUACC | 163 |
| #43 | CAACGCUGA CCA UGGGAGGAAUGUGGGAGGGCGCCAGCG | 164 |
| #14 | CAGCCA AGGGUUGGAUAGGGGGUAGGGAGCCGUAGCAGCG | 165 |

ORPHAN (1 clone)

| #18 | CCGCCUGCGAUAGUUAGACCGUUGAGCUGAGAGCAACACU | 166 |

NITROCELLULOSE FILTER BINDERS (11 clones)

| #1 | AAGGUGGGUUGA<u>GGAGG</u>AAAGUAGCGUGAGUCAGUACCA | 167 |
| --- | --- | --- |
| #4 | AGGGAGGAUUGU<u>GGAGG</u>AAGGGAGUGGAAGUGUCCCAGCC | 168 |
| #5 | GGAUGACCAAGCGUCGAACGAG<u>GGAGG</u>AUUGUGGU<u>GGAGG</u> | 169 |
| #12 | GGGUGGAUUGU<u>GGAGG</u>AAGUAGCGCAGGGUUCCGUAAGCC | 170 |
| #21 | AGGAGCGCCAUGAAGCAAAG<u>GGAGG</u>AUUGUGGUGGAAGGC | 171 |

TABLE 7-continued

| | | SEQ ID NO. |
|---|---|---|
| #24 | ACUGGAGCCAUACAGACGAGAGGAUGGGUGUGUGGAGGA | 172 |
| #31 | AGGGAGGAUUGUGGAGGAAGGGAGUGGAAGUGUCUCAGCC | 173 |
| #32 | UCGGGUGAGGACUGGUAGAAAAAGGAGGGUUGUGGAGGAG | 174 |
| #34 | ACCUGAUAACCGCGGAGGGAGGAUAGAGGAGGAAGUGCGG | 175 |
| #35 | AGGCAGCCCCUCGACGAGAAAGGUGGGUAGUGGAGGAAC | 176 |
| #42 | CUUACGACACCAAAGGGAGGAUUGUGGUGGAAUGGGGUCG | 177 |

TABLE 8

| | SEQ ID NO. |
|---|---|

Truncated IL-4 Ligands

2'F
9   (Kd = 14.7 nM full-length; Kd = 18 nM truncate)
5'-(ggg)aaACGGCUGUAACAAACAAGGUGGGGGGCCACACA-3'            178

12 (Kd = 30 nM full-length)
5'-gggagacaagaauaaacgcucaaGUCUGACUAUUGGGGCGCCACAAUAUCAACGGC-3'    179

18 (Kd = 43 nM full-length)
5'-aagaauaaacgcucaaGCUGCCCAAGGAAUUUAACUUGGACCGCGAUCU- 3' (orphan)   180

21 (Kd = 11 nM full-length)
5'-AAGCAAAGGGAGGAUUGUGGUGGAAGGCUUC-3' (orphan)              181

2'NH$_2$
29 (Kd = 8.3 nM full-length; Kd = 10 nM truncate)
5'-(ggg)acgcucaaGAGCUGGUGAGCCACGUAUACGGCCUUAGGGGCUUGGGCG-3'    182

2'F/NH$_2$
9 (Kd = 3.3 nM full-length)
5'-gggagacaagaauaaacgcucaaAGAGUGCAGGUCUGGGGCGCCACAAUUAGAACGGCA-3'    183

18 (Kd = 30 nM full-length)
5'-gcucaaCCGCCUGCGAUAGUUAGACCG-3' (orphan)              184

28 (Kd = 8.7 nM full-length)
5'-CCUGCGACGCCAGGGGUGGAUAGGGGGAAGGGAGCGGuucgacagga-3'    185

TABLE 9

| | SEQ ID NO. |
|---|---|

Initial random sequence RNA pool:

5'-GGGAGACAAGAAUAAACGCUCAA-(N)$_{40}$-UUCGACAGGAGGCUCACAACAGGC-3'   186

5'-Primer:

5'-TAATACGACTCACTATAGGGAGACAAGAATAAACGCTCAA-3'            187

3'-Primer:

5'-GCCTGTTGTGAGCCTCCTGTCGAA-3'                            188

TABLE 10

| | | SEQ ID NO. |
|---|---|---|
| 43 (10) | ACAUCGUAUAA---CUCUA-AGGGCCUGGAUAUACGAUGAA | 189 |
| 64 | ACAUCGUAUAA---CUCUA-AGCGCCUGGAUAUACGAUGAA | 190 |
| 64a | ACAUCGUAUAA---CUCUA-AGAGCCUGGAUAUACGAUGAA | 191 |
| 64b | ACAUCGUAUAA---CUCUA-AGUGCCUGGAUAUACGAUGAA | 192 |
| 55 (5) | ACAUCGUAUAAU--CUCUA-AGAGCCUGGAUAUACGAUGAA | 193 |
| 68 | ACAUCGUAUAAUCUCUCUA-AGAGCCUGGA-AUACGAUGAA | 194 |
| 6 | AUCCCA-AU----CUCUA-AGAGCCUGGA-U---AAGAAUGCGCAUUGGGC | 195 |
| 54 | AUCCCA-AU----CUCUA-AGAGCCUGGA-U---GACAAU-CGCAUUGGGC | 196 |
| 57 | AUCCCA-AU----CUCUA-AGAGCCUGGA-U---GAGAAUGCGCAUUGGGC | 197 |
| 10 | CUGAGAU---CUCUA-AGAGCCUGGACU-CAG-CUCCGACUGACC | 198 |
| 34 | CUGAGAU---CUCUA-AGAGCCUGGACU-CAG-CUCCGAUUGAUCC | 199 |
| 41 | CUGAGAU---CUCUA-AGAGCCUGGACU-CAG-CUCCGAUUGAACC | 200 |
| 15 (2) | UCUCUA-UGAGCCUGGA-U-CGACGAACUCUCUACGGGCUGUG | 201 |
| 56 (2) | UCUCUA-AGAGCCUGGA-U-GUCGAGGGGCCAUUUCGCACGC | 202 |
| 2 | AUCUCUACUGAGCCUGGA-U-UCGCCAGAAGUUUUAUCACAGU | 203 |
| 59 | CGUAAAAGUUAUCGAAU--CUCUG-UGAGCCUGGA-U-CGAUUAC | 204 |
| 3 | CUGAGAU---CUCUA-AGAGCCUGGACUCAGCUACGAUUGAGCGUUUAUUCUUG | 205 |

TABLE 11

| | SEQ ID NO. |
|---|---|
| STARTING RNA: | |
| 5'-GGGAGCUCAGAAUAAACGCUCAA (N$_{30}$) UUCGACAUGAGGCCCGGAUCCGGC | 206 |
| PCR PRIMER 1: | |
| BamHI<br>5'-GCCGGATCCGGGCCTCATGTCGAA | 207 |
| PCR PRIMER 2: | |
| HindIII<br>5'-CCGAAGCTTAATACGACTCACTATAGGGAGCTCAGAATAAACGCTCAA<br>          T7 promoter | 208 |

TABLE 12

Sequences of the hTNFa ligands[a]

| Clone | 5' constant | random | 3' constant | $K_n$, nM[d] | Class | SEQ ID NO |
|---|---|---|---|---|---|---|
| 1A[b] (2)[c] | gggagcucagaauaaacgcucaa | ACGGCUGACAACGGCUGGACUUGCGUAUUG | uucgacaugaggcccggauccggc | | | 209 |
| 2A (3) | gggagcucagaauaaacgcucaa | GCGCUUGACCAUUUCGUAGGGUCGCCCUUG | uucgacaugaggcccggauccggc | | | 210 |
| 3A (2) | gggagcucagaauaaacgcucaa | GAUCGACGCAUCGAGUCGCCUCAUCGCUCC | uucgacaugaggcccggauccggc | 135 | I | 211 |
| 4A | gggagcucagaauaaacgcucaa | CGCACUCGGACGGAAUCUCCGUAGGACACG | uucgacaugaggcccggauccggc | 320 | II | 212 |
| 5A | gggagcucagaauaaacgcucaa | UGUCAUGCAUGUGUGUCGCCUCAUCACGCA | uucgacaugaggcccggauccggc | | | 213 |
| 6A (7) | gggagcucagaauaaacgcucaa | CCACUGGCUAGGAACUCGAGUACUGGGUGG | uucgacaugaggcccggauccggc | 120 | II | 214 |
| 7A (2) | gggagcucagaauaaacgcucaa | UUCGAAGCCACGUUUCAUGUCCGUCGCUGC | uucgacaugaggcccggauccggc | | | 215 |
| 8A | gggagcucagaauaaacgcucaa | CAGUGGAGGCUGUCCAAACCCACCCACCCC | uucgacaugaggcccggauccggc | 785 | I | 216 |
| 9A (4) | gggagcucagaauaaacgcucaa | GUGGAGGGUACGUGGAGGGGAGAGCGAUA | uucgacaugaggcccggauccggc | | | 217 |
| 10A | gggagcucagaauaaacgcucaa | UCUCAUGCUCGCGUGCGUCGCCUCAACCA | uucgacaugaggcccggauccggc | | | 218 |

TABLE 12-continued

Sequences of the hTNFa ligands[a]

| Clone | 5' constant | random | 3' constant | $K_n$, nM[d] | Class | SEQ ID NO |
|---|---|---|---|---|---|---|
| 11A | gggagcucagaauaaacgcucaa | UCCCUCAGUGUCAAGUGCGUCGCCUCAGCA | uucgacaugaggcccggauccggc | | | 219 |
| 12A | gggagcucagaauaaacgcucaa | CUUCUUGGCCCCGUCUCAAUGUCCGUACUUC | uucgacaugaggcccggauccggc | | | 220 |
| 13A (2) | gggagcucagaauaaacgcucaa | CGUGAUUUGGCCACGGGAAAGAGCCAUACC | uucgacaugaggcccggauccggc | | | 221 |
| 14A (4) | gggagcucagaauaaacgcucaa | CGUUGAACGCUUGGUUUCAUGUCCCUCGCC | uucgacaugaggcccggauccggc | | | 222 |
| 15A | gggagcucagaauaaacgcucaa | CGUCGAUCGCGUGCUGUAGCCUCAGGCACC | uucgacaugaggcccggauccggc | | | 223 |
| 16A | gggagcucagaauaaacgcucaa | GGUGGAAGGCCUUUGAAGCCCGUACAUCUCC | uucgacaugaggcccggauccggc | | | 224 |
| 17A | gggagcucagaauaaacgcucaa | GGUCGAACUAGCGCUGGAGCGUGCGUUGGU | uucgacaugaggcccggauccggc | | | 225 |
| 18A (2) | gggagcucagaauaaacgcucaa | GUCGCUCGAUCGUUUCAUGCCCGUCCGACC | uucgacaugaggcccggauccggc | | | 226 |
| 19A | gggagcucagaauaaacgcucaa | GUCGAUGCGCAGUCCGCCUCAGCUGCACUG | uucgacaugaggcccggauccggc | | | 227 |
| 20A (3) | gggagcucagaauaaacgcucaa | GGUGUGCCCAAGGCCCUUGAGAGAGGCGUG | uucgacaugaggcccggauccggc | | | 228 |
| 21A | gggagcucagaauaaacgcucaa | CGUCUAGGAACUGCGUCGCCUCAACAGCGC | uucgacaugaggcccggauccggc | | | 229 |
| 22A | gggagcucagaauaaacgcucaa | GUCGGAUGGUUUUGCGCGUUUCCCG | uucgacaugaggcccggauccggc | | | 230 |
| 23A | gggagcucagaauaaacgcucaa | CCUCAUCCUCGCACGCCAUCGCCUGAACCG | uucgacaugaggcccggauccggc | 52 | I | 231 |
| 24A | gggagcucagaauaaacgcucaa | GGUGUGCCAAAGGCCCUUGAGAGAGGCGUA | uucgacaugaggcccggauccggc | | | 232 |
| 25A (2) | gggagcucagaauaaacgcucaa | GGCCGCAUGCCCCUCCUAACAGCAUGCAAC | uucgacaugaggcccggauccggc | 40 | I | 233 |
| 26A | gggagcucagaauaaacgcucaa | CCCUCGUGCGUGCGCUUGGAGCGUGGCGCA | uucgacaugaggcccggauccggc | | | 234 |
| 27A | gggagcucagaauaaacgcucaa | GUCGCUCGAUCGUUUCAUGUCCGUUCGACC | uucgacaugaggcccggauccggc | | | 235 |
| 28A | gggagcucagaauaaacgcucaa | GUCCACACUUUGCCGAGCGUCCUAGUG | uucgacaugaggcccggauccggc | | | 236 |
| 1C | gggagcucagaauaaacgcucaa | CGGGUGAAUCACGGCUGGUGCGUUGCCCC | uucgacaugaggcccggauccggc | | | 237 |
| 2C (2) | gggagcucagaauaaacgcucaa | CGUCGACGCACUGUGCCGCCUCACACACGC | uucgacaugaggcccggauccggc | | | 238 |
| 3C (2) | gggagcucagaauaaacgcucaa | GCGAACGUCAUGCCGCCUCAUCAUGCCACG | uucgacaugaggcccggauccggc | | | 239 |
| 4C | gggagcucagaauaaacgcucaa | CUAGGCCCACCGUCCCUUCUAACAACGUC | uucgacaugaggcccggauccggc | 92 | I | 240 |
| 5C | gggagcucagaauaaacgcucaa | CAGUCACGAACGUGCGCCGGAAGAACGCUC | uucgacaugaggcccggauccggc | | | 241 |
| 6C | gggagcucagaauaaacgcucaa | UGUCGCACGUGUCCCGGCCCGCCCUACCCC | uucgacaugaggcccggauccggc | | | 242 |
| 7C (2) | gggagcucagaauaaacgcucaa | CAGGUGGCACCGCCCUUCCAACACGGUGCG | uucgacaugaggcccggauccggc | 297 | I | 243 |
| 8C (2) | gggagcucagaauaaacgcucaa | GUCCACACUUUGCCGAGCGUCCUAGUG | uucgacaugaggcccggauccggc | 430 | II | 244 |
| 9C | gggagcucagaauaaacgcucaa | AUGGUGGAGGCCAUCUCAAACCCACGACAC | uucgacaugaggcccggauccggc | 120 | I | 245 |
| 10C | gggagcucagaauaaacgcucaa | CGCCGAGACCCACCUCAUAACACCGCUACC | uucgacaugaggcccggauccggc | 500 | I | 246 |
| 11C | gggagcucagaauaaacgcucaa | UGAGGCGCGCCACAGGAUGGCCCUCAACCC | uucgacaugaggcccggauccggc | 140 | I | 247 |
| 12C | gggagcucagaauaaacgcucaa | GUCCGCAUGAUGCUUCGAACAGCAUACAAC | uucgacaugaggcccggauccggc | 690 | I | 248 |
| 13C | gggagcucagaauaaacgcucaa | GGUGUGCCCCUACGUGCGGCCCUUCGUUUA | uucgacaugaggcccggauccggc | | | 249 |
| 14C | gggagcucagaauaaacgcucaa | CGGCUUGCAGGUCGCCGAAAUGACCGCACA | uucgacaugaggcccggauccggc | 60 | II | 250 |
| 15C | gggagcucagaauaaacgcucaa | CUAGUUCAACCGUCCCUUCUAACAACCGUC | uucgacaugaggcccggauccggc | 124 | I | 251 |
| 16C | gggagcucagaauaaacgcucaa | CCUGGUGGUCGUGCGGCUGUCGCCUCAAGG | uucgacaugaggcccggauccggc | 200 | I | 252 |
| 17C | gggagcucagaauaaacgcucaa | GAUCGAAGUUGCUGUCCGCCUCAGCGACUC | uucgacaugaggcccggauccggc | | | 253 |
| 18C | gggagcucagaauaaacgcucaa | UGUCGAGUGCGAUGGAGGAGUAGGGAUGCA | uucgacaugaggcccggauccggc | 460 | O | 254 |
| 19C | gggagcucagaauaaacgcucaa | UGUCGAUCGUGUCAAGGUCCGUCCUACUUC | uucgacaugaggcccggauccggc | 83 | I | 255 |

[a]Only unique sequences are shown. A unique sequence is defined as one that differs from all others by three or more nucleotides.
[b]Clone numbers followed by "A" were obtained from the round 23A or the round 6C pool. Clone numbers followed by "C" were obtained only from the round 6C pool.
[c]The number in parentheses indicates the occurrence of the clone in the sequenced pool.
[d]No value is shown for ligands that have Kd greater than 1 M.

TABLE 13

Binding specificity of the evolved pool of ligands from round 23A

| Target | KD, nM | Ratio: Kd Target/Kd hNFa |
|---|---|---|
| hTNFa | 700 | 1 |
| hTNFβ | >1,000,000 | >1,400 |
| mTNFa | >1,000,000 | >1,400 |

TABLE 14

Ki values of hTNFa competitors on the U937 cell competition assay

| Competitior | Ki, nM | R[a] |
|---|---|---|
| sTNF-R2 | 3.3 | 0.99323 |
| random RNA | >1,000,000 | |
| 6 A | 9,100 | 0.93776 |
| 25 A | 21 | 0.98105 |
| 4C | 1,200 | 0.93496 |

TABLE 14-continued

Ki values of hTNFa competitors on the U937 cell competition assay

| Competitior | Ki, nM | R[a] |
|---|---|---|
| 14C | 930 | 0.88453 |
| 18C | 2,500 | 0.97483 |

[a]Fit correlation coefficient

TABLE 15

Effect of 2'F-pyrimidine modification in the affinities and inhibitory activities of the hTNFa ligands

| Clone | 2'OH $K_D$, nM | 2'F $K_D$, nM | 2'OH[a] $K_i$, nM | 2'F $K_i$, nM | Class |
|---|---|---|---|---|---|
| 3 A (2) | 135 | 623 | | | I |
| 4C | 92 | NB[b] | 1,200 | | I |
| 7C (2) | 297 | 442 | | | I |
| 8A | 785 | ND[c] | | | I |
| 9C | 120 | 400 | | | I |
| 10C | 500 | NB | | | I |

TABLE 15-continued

Effect of 2'F-pyrimidine modification in the affinities and inhibitory activities of the hTNFa ligands

| Clone | 2'OH $K_D$, nM | 2'F $K_D$, nM | 2'OH[a] $K_i$, nM | 2'F $K_i$, nM | Class |
|---|---|---|---|---|---|
| 11C | 140 | NB | | | I |
| 12C | 690 | NB | | | I |
| 15C | 124 | NB | | | I |
| 16C | 200 | 123 | ~313 | 9,191 | I |
| 19C | 83 | NB | | | I |
| 23A | 52 | 400 | ~241 | 14,671 | I |
| 25A (2) | 40 | 445 | 21 | | I |
| 4 A | 320 | 178 | | | II |
| 6A (7) | 120 | 74 | 9,100 | 8,156 | II |
| 8C (2) | 430 | 503 | | | II |
| 14C | 60 | 133 | 930 | 11,540 | II |
| 18C | 460 | NB | 2,500 | | O |

[a] $K_i$ values were obtained based on 5–8 point curves except for 16C and 23A 2⁺OH where only 3 points were used.
[b] No binding.
[c] Not determined.

TABLE 16

| | SEQ ID NO. |
|---|---|
| Starting DNA: | |
| 40N7: 5'GGGAGGACGATGCGG[-40N-]CAGACGACTCGCCCGA 3' | 256 |
| SELEX PCR Primers: | |
| 5G7: 5'GGGAGGACGATGCGG 3' | 257 |
| 3G7: 5'XXXXTCGGGCGAGTCGTCTG 3' | 258 |

X = biotin

TABLE 17

Conditions and progress of the SELEX against RANTES

| Round | [DNA], M | [RANTES], M | net % bound | Signal/noise | PF[a] | PS[b] | B-Wash[c] (ml) | U-Wash[d] (ml) | SPKD[e] | M KD[f], nM |
|---|---|---|---|---|---|---|---|---|---|---|
| 150 mM NaCl | | | | | | | | | | |
| 1 | 3.00E−05 | 3.0E−06 | 0.5 | 35.0 | + | | 25 | 25 | 1.24E−03 | 3000 |
| 2 | 3.30E−06 | 3.3E−07 | 0.1 | 7.8 | + | | 25 | 25 | 1.01E−03 | |
| 3 | 3.00E−06 | 3.0E−07 | 0.1 | 1.4 | + | | 25 | 25 | 1.85E−03 | |
| 4 | 1.00E−06 | 1.0E−07 | 0.2 | 1.5 | + | | 25 | 25 | | |
| 5 | 3.00E−07 | 3.0E−08 | 0.2 | 1.5 | + | | 25 | 50 | 2.20E−40 | |
| 6 | 1.00E−07 | 1.0E−08 | 0.2 | 1.9 | + | | 50 | 100 | 4.09E−05 | |
| 7 | 1.00E−07 | 1.0E−08 | 0.4 | 1.5 | + | | 50 | 100 | 7.89E−06 | |
| 8 | 3.00E−08 | 3.0E−09 | 0.3 | 1.9 | + | + | 50 | 100 | 1.91E−06 | 890 |
| 9 | 3.50E−08 | 3.0E−09 | 0.5 | 1.9 | + | + | 50 | 100 | 1.89E−06 | |
| 10 | 3.00E−08 | 3.0E−09 | 0.3 | 1.4 | + | + | 50 | 100 | 9.85E−07 | |
| 11 | 2.70E−08 | 3.0E−09 | 1.4 | 6.1 | + | + | 50 | 100 | 1.90E−07 | |
| 12 | 1.20E−08 | 3.0E−09 | 0.1 | 1.2 | + | + | 50 | 100 | 2.44E−06 | |
| 13 | 3.00E−08 | 1.0E−08 | 0.6 | 2.0 | + | + | 50 | 100 | 1.60E−06 | 159 |
| 14 | 2.50E−08 | 1.0E−08 | 0.2 | 2.0 | + | + | 10 | | 4.96E−06 | |
| 15 | 2.50E−08 | 1.0E−08 | 0.7 | 3.0 | + | + | 5 | | 1.39E−06 | |
| 16 | 2.50E−08 | 1.0E−08 | 0.5 | 3.5 | + | + | 5 | | 1.96E−06 | |
| 17 | 9.00E−09 | 3.0E−09 | 0.2 | 1.5 | + | + | 5 | | 1.48E−06 | |
| 18 | 6.00E−09 | 3.0E−09 | 0.2 | 1.4 | + | + | 5 | | 1.49E−06 | 49 |
| 19 | 9.00E−09 | 3.0E−09 | 0.2 | 1.3 | + | + | 5 | | 1.48E−06 | 18 |

[a] Prefiltered DNA through nitrocellulose to counter select for nitocellulose binding molecules
[b] Preadsorption of the DNA under binding conditions
[c] Volume of buffer used to wash the captured complexes
[d] Volume of 0.5 M urea wash following the buffer wash
[e] Calculated single pdint KD from the binding data at each round
[f] $K_D$ values obtained from binding curves References Adams, D. O., Hamilton, T. A. 1984. *Annu Rev. Immunol.* 2: 283–318.

Adams, S. M., Blakesley, R. 1991. *Focus* 13 (2): 56–58.

Aggarwal, B. B., W. J. Kohr, P. E. Hass, B. Moffat, S. A. Spencer, et al. 1985. *J. Biol. Chem.* 260: 2345–2354.

Alam, R., S. Stafford, P. Forsythe, R. Harrison, D. Faubic, et al. 1993. *J. Immunol.* 150: 3442–3447.
Allen, P. M., Unanue, E. R. 1987. *Adv. Exp. Med. Biol.* 225: 147–154.
Anderson, P., et al., 1982. *J. Biol. Chem.* 257: 11301–11304.
Bancroft, G. J., et al., 1987. *J. Immunol.* 139: 1104–1107.
Bancroft, G. J., et al., 1989. *J. Immunol.* 143: 127–130.
Bazan, J. F. 1990a. *Immunol. Today* 11: 350–354.
Belosevic, M. et al., 1989. *J. Immunol.* 143, 266–274.
Beutler, B. and A. Cerami 1989. *Ann. Rev. Immunol.* 7: 625–655.
Beutler, B., I. W. Milsark and A. C. Cerami 1985. *Science* 229: 869–871.
Bischoff, S. C., M. Krieger, T. Brunner, A. Rot, V. V. Tscharner, et al. 1993. *Eur. J. Immunol.* 23: 761–767.
Bowen, B., J. Steinberg, U. K. Laemmli and H. Weintraub 1980. *Nucl. Acids Res.* 8: 1–20.
Brennan, F. M., D. Chantry, A. Jackson, R. Maini and M. Feldmann, 1989. *Lancet* 2: 244–247.
Briscoe, D. M., et al., 1992. *J. Immunol.* 147: 2954–2960.
Brockhaus, M., H. J. Schoenfeld, E. J. Schlaege, W. Hunziker, W. Lesslauer, et al., 1990. *Proc. Natl. Acad. Sci. USA* 87: 3127–3131.
Brown, M. A., et al., 1987. *Cell* 50: 809–818.
Buchmeier, N. A., Schreiber, R. D., 1985. *Proc. Natl. Acad. Sci. USA* 82: 7404–7408.
Casadaban, M. and S. Cohen, 1980. *J. Mol. Biol.* 138: 179–207.
Casey, L. C., R. A. Balk and R. C. Bone, 1993. *Ann. Intern Med.* 119: 771–777.
Clerici, M. & Shearer, G. M., 1993. *Immunol. Today* 14, 107–111.
Coffman, R. L., et al., 1986., *J. Immunol.* 136: 4538–XXXX.
Crawford, R. M., et al., 1987. *J. Inuunol.* 139: 135–141.
Davanloo, P., et al., 1984. *Proc. Natl. Acad. Sci. USA* 81: 2035–2039.
Del Prete, G., et al., 1988. *J. Immunol.* 140: 4193–XXXX.
Derynck, R., et al., 1982. *Nucl. Acids Res.* 10: 3605–3615.
Dinarello, C. A. and J. G. Cannon, 1993. *Ann. Intern. Med.* 119: 853–854.
Ding, A. H., et al., 1988. *J. Immunol.* 141: 2407–2412.
Duh, E. J., W. J. Maury, T. M. Folks, A. S. Fauci and A. B. Rabson, 1989. *Proc. Natl. Acad. Sci. USA* 86: 5974–5978.
Eck, M. J., B. Beutler, G. Kuo, J. P. Merryweather and S. R. Sprang, 1988. *J. Biol. Chem.* 263: 12816–12819.
Erbe, et al., 1990. *Mol. Immunol.* 27: 57–67.
Feldmann, M., 1989. *Immunology Supplement* 2: 66–71.
Ferrara, J. L. M., et al., 1991. *N. Engl. J. Med.* 324: 667–674.
Fiedler, V. B., I. Loof, E. Sander, V. Voehringer, C. Galanos, et al., 1992. *J. Lab. Clin. Med.* 120: 574–588.
Finkelman, F. D., et al., 1986. *Proc. Natl. Acad. Sci. USA* 83: 9765–XXXX.
Finkelman, F. D., et al., 1990. *Annu Rev. Immunol.* 8: 303–XXX.
Finkelman, F. D., Katona, I. M., Urban Jr., J. F., Paul, W. E., 1989. In Ciba Foundation Symposium. IgE, Mast Cells and the Allergic Response. Wiley. Chichester, pp.3–22.
Folks, T. M., K. A. Clouse, J. Justment, A. Rabson, E. Duh, et al., 1989. *Proc. Natl. Acad. Sci. USA* 86: 2365–2368.
Galizzi, J. P., et al., 1990. *Int. Immunol.* 2: 669–XXX.
Gao, J. L., D. B. kuhns, H. L. Tiffany, D. McDermott, X. Li, et al., 1993. *J. Exp. Med.* 177: 1421–1427.
Gazzinelli, R. T. et al., 1992. *J. Immunol.* 148, 1792–1796.
Gleichmann, E., et al., 1982. *Eur. J. Immunol.* 12: 152–XXX.
Gold, L., Tuerk, C., Allen, P., Binkley, J., Brown, D., Green, L., MacDougal, S., Schneider, D., Tasset, D., and Eddy, S., 1993. In *The RNA World*, Ch. 19, 497–509.

Goldfeld, A. E. and T. Maniatis, 1989. *Proc. Natl. Acad. Sci. USA* 86: 1490–1494.
Grau, G. E., L. F. Fajardo, P. F. Piguet, B. Allet, P. H. Lambert, et al., 1987. *Science* 237: 1210–1212.
Green, S. J., et al., 1990. *J. Immunol.* 145: 4290–4297.
Greenlund, A. C., et al., 1992. *J. Interferon Res.* (Abstr.) 12: S103.
Gu, D., et al., 1995. *J. Exp. Med.* 181: 547–557.
Haak-Frendscho, M., S. A. Marsters, J. Mordenti, S. Brady, N. A. Gillett, et al., 1994. *J. Immunol.* 152: 1347–1353.
Harada, N., et al., 1990. *Proc. Natl. Acad. Sci. USA* 87: 857–XXX.
Heinzel, F. P. et al., 1991. *Proc. Natl. Acad. Sci. USA* 88: 7011–7015.
Heinzel, F. P., et al., 1989. *J. Exp. Med.* 169: 59–72.
Hershey, G. K. K., et al., 1990. *J. Biol. Chem.* 265: 17868–17875.
Higuchi, C. M., et al., 1989. *Cancer Research* 49: 6487–6492.
Hinshaw, L. B., T. E. J. Emerson, F. B. J. Taylor, A. C. Chang, M. Duerr, et al., 1992. *J. Trauma* 33: 568–573.
Hohmann, H. P., R. Remy, M. Brockhaus and A. P. G. M. Van-Loon, 1989 *J. Biol. Chem.* 264(14927–14934):
Hoon, D. S. B., et al., 1991. *Cancer Research* 51: 5687–5693.
Horuk, R., C. E. Chitnis, W. C. Darbonne, T. J. Colby, A. Rybicki, et al., 1993. *Science* 261: 1182–1184.
Howard, J. G. et al., 1980. *Nature* 288, 161–162.
Howard, M., et al., 1982. *J. Exp. Med.* 155: 914–923.
Hsieh, C. -S., et al., 1993. *Science* 260, 547–549.
Hu-Li, J., et al., 1987. *J. Exp. Med.* 165: 157–XXX.
Idzerda, R. L., et al., 1990. *J. Exp. Med.* 171: 861–73.
Isakson, P. C., et al., 1982. *J. Exp. Med.* 155: 734–748.
Jansen, J. H., et al., 1989. *J. Exp. Med.* 170: 577–XXX.
Jones, E. Y., D. I. Stuart and N. P. C. Walker, 1989. *nature* 338: 225–228.
Jung, V., et al., 1987. *Proc. Natl. Acad. Sci. USA* 84: 4151–4155.
Katona, I. M., et al., 1991. *J. Immunol.* 146: 4215–4221.
Keffer, J., L. Probert, H. Cazlaris, S. Georgopoulos, E. Kaslaris, et al., 1991. *EMBO J.* 10: 4025–4031.
Khorram, O., R. N. Taylor, I. P. Ryan, T. J. Schall and D. V. Landers, 1993. *Am. J. Obstet. Gynecol.* 169: 1545–1549.
Kishimoto, T., et al., 1994. *Cell* 76: 253–262.
Kuhn, R. et al., 1993 *Cell* 75, 263–274.
Kuhn, R., et al., 1991. *Science* 254: 707–710.
Kuna, P., S. R. Reddigari, T. J. Schall, D. Rucinski, M. Sadick, et al., 1993. *J. Immunol.* 150: 1932–1943.
Kuna, P., S. R. Reddigari, T. J. Schall, D. Rucinski, M. Y. Viksman, et al., 1992. *J. Immunol.* 149: 636–642.
Landolfo, S., et al., 1985. *Science* 229: 176–179.
Le Beau, M. M., et al., 1989. *Blood* 73: 647–50.
Leal, L., M., C., C., et al., 1993. *Eur. J. Immunol.* 23: 566–569.
Lebman, D. A., Coffman, R. L. 1988. *J. Ex. Med.* 168: 853–XXX.
Lee, F., et al., 1986. *Proc. Natl. Acad. Sci. USA* 83: 2061–2065.
Lenardo, M. J. and D. Baltimore, 1989. *Cell* 58: 227–229.
Lewis, D. B., et al., 1993. *Proc. Natl. Acad. Sci. USA* 90: 11618–11622.
Liew, F. Y. et al., 1989. *Eur. J. Immunol.* 19, 1227–1232.
Loetscher, H., M. Steinmetz and W. Lesslauer 1991. *Cancer Cells* 3: 221–226.
Loetscher, H., Y.-C. E. Pan, H.-W. Lahm, R. Gentz, M. Brockhaus, et al., 1990. *Cell* 61: 351–359.
Lowenthal, J. W., D. W. Ballard, E. Boehnlein and W. C. Green, 1989. *Proc. Natl. Acad. Sci. USA* 86: 2331–2335.

Lowenthal, J. W., et al., 1988. *J. Immunol.* 140: 456–464.

Mantovani, A., Dejana, E., 1989. *Immunol. Today* 10: 370–375.

McGee, D. P. C., et al., 1995. *Nucleosides & Nucleotides* 14: 1329–1339.

McInnes, A., Rennick, D. M., 1988. *J. Exp. Med.* 167: 598–XXX.

Mogi, M., M. Harada, P. Riederer, H. narabayashi, K. Fujita, et al. 1994. *Neurosc. Lett.* 165: 208–210.

Mohler, K. M., D. S. Torrance, C. A. Smith, R. G. Goodwin, K. E. Stremler, et al., 1993. *J. Immunol.* 151: 1548–1561.

Moore, K. W. et al., 1990. *Science* 248, 1230–1234.

Moore, K. W. et al., 1993. *Ann. Rew. Immunol.* 11, 165–190.

Mosely, B., et al., 1989. *Cell* 59: 335–348.

Mosmann, T. R., et al., 1986. *Proc. Natl. Acad. Sci. USA* 83: 5654–XXXX.

Mosmann, T. R., et al., 1989. *Annu. Rev. Immunol.* 7: 145–173.

Mulkerrin, M. G., Wetzel, R. 1989. *Biochemistry* 28: 6556–6561.

Munro, J. M., et al., 1989. *Am. J. Path.* 135: 121–131.

Nelson, P. J., H. T. Kim, W. C. Manning, T. J. Goralski and A. M. Krensky, 1993. *J. Immunol.* 151: 2601–2612.

Neote, K., W. Darbonne, J. Ogez, R. Horuk and T. J. Schall, 1993. *J. Biol. Chem.* 268: 12247–12249.

Noma, Y., et al., 1986. *Nature* 319: 640–46.

Oliff, A., D. Defeo-Jones, M. Boyer, D. Martinez, D. Kiefer, et al., 1987. *Cell* 50: 555–563.

Oliver, K., et al., 1985. *Proc. Natl. Acad. Aci. USA* 82: 2465–XXXX.

Osborn, L., S. kunkel and G. J. Nabel, 1989. *Proc. Natl. Acad. Sci. USA* 86: 2336–2340.

Park, L. S., et al., 1987. *Proc. Natl. Acad. Sci. USA* 84: 1669–673.

Parrillo, J. E. 1991. *Annals Int. Med.* 115: 491–492.

Paul, W. E., 1991. *Blood* 77: 1859–870.

Paul, W. E., Seder, R. A., 1994. *Cell* 76: 241–251.

Pennica, D., V. T. Lam, N. K. Mize, R. F. Weber, M. Lewis, et al., 1992. *J. Biol. Chem.* 267: 21172-.

Pieken et al., 1991. *Science* 253: 314–317.

Piguet, P. F. 1992. TNF and Alloreactions. Involvement of TNF in the Effector Phase of Graft-Versus-Host and host-Versus-Graft Reactions. *TUMOR NECROSIS FACTORS: The Molecules and Their Emerainc Role in Medicine.* New York, Raven Press, Ltd.

Plaut, M., et al., 1989. *Nature* 339: 64–67.

Pober, J. S., et al., 1986. *J. Immunol.* 137: 1893–1896.

Rabin, E., et al., 1985. *Proc. Natl. Acad. Sci. USA* 82: 2935–XXXX.

Rapoport, M. J., et al., 1993. *J. Exp. Med.* 178: 87–99.

Rathanaswami, P., M. Hachicha, M. Sadick, T. J. Schall and S. R. McColll, 1993, *J. Biol. Chem.* 268: 5834–5839.

Ravetch, J. V., 1994. *Cell* 78: 553–560.

Rinderknecht, E., et al., 1984. *J. Biol. Chem.* 259: 6790–6797.

Rot, A., M. Krieger, T. Brunner, S. C. Bischoff, T. J. Schall, et al., 1992. *J. Exp. Med.* 176(1489–1495):

Salgame, P. et al., 1991. *Science* 254, 279–282.

Sato, T. A., et al., 1993. *J. Immunol.* 150: 2717–2723.

Scahill, S. J., et al., 1983. *Proc. Natl. Acad. Sci. USA* 80: 4654–4658.

Schall, T. J., 1991. *CYTOKINE* 3: 165–183.

Schall, T. J., K. Bacon, K. J. Toy and D. V. Goeddel, 1990. *Nature* 347: 669–671.

Schall, T. J., M. Lewis, J. Koller, A. Lee, G. C. Rice, et al., 1990. *Cell* 52: 415–423.

Schall, T. J., N. J. Simpson and J. Y. Mak, 1992. *Eur. J. Immunol.* 22: 1477–1481.

Schreiber, R. D., Celada, A., 1985. *Lymphokines.* 11: 87–118.

Schreiber, R. D., et al., 1992. *Int. J. Immunopharmac.* 14: 413–419.

Shanafelt, A. B. et al., 1991. *EMBO J.* 10, 4105–4112.

Sher, A. & Coffman, R. L. 1992. *Ann. Rev. Immunol.* 10, 385–409.

Sher, A. et al., 1992 *Immunol. Rev.* 127, 183–204.

Singh, H., J. H. LeBowitz, A. S. J. Baldwin and P. A. Sharp, 1988. *J. Biol. Chem.* 262: 6951–6954.

Snapper, C. M., Paul, W. E., 1987. *Science* 236: 944–947.

Smith, R. A. and C. Baglioni, 1987. *J. Biol. Chem.* 262: 6951–6954.

Spits, H., et al., 1987. *J. Immunol.* 139: 1142–1147.

Steinman, L., 1993. *Scientific American* 269 (3): 107–114.

Strunk, R. C., et al., 1985. *J. Biol. Chem.* 260: 15280–15285.

Suzuki, Y., et al., 1988. *Science* 240: 516–518.

Sylvestre, D. L., Ravetch, J. V. 1994. *Science* 265: 1095–1098.

Te Velde, A. A., et al., 1988. *J. Immunol.* 140: 1548–1554.

Tepper, R. I., et al., 1989. *Cell* 57: 503–512.

Tepper, R. I., et al., 1990. *Cell* 62: 457–467.

Thornhill, M. H., et al., 1991. *J. Immunol.* 146: 592–598.

Traugott, U., Lebon, P., 1988. *J. Neurol. Sci.* 84: 257–264.

Trenn, G., et al., 1988. *J. Immunol.* 140: 1101–XXXX.

Trinchieri, G., Perussia, B., 1985. *Immunol. Today* 6: 131–135.

Tuerk, C., Gold, L., 1990. *Science* 249: 505–510.

Umland, S. P., et al., 1992. *Clin. Immunol. Immunophathol.* 63: 66–73.

Ushiyama, C., et al., 1995. *J. Immunol.* 154: 2687–2696.

van Leeuwen, B. H., et al., 1989. *Blood* 73: 1142–1148.

van Rappard-van Der Veen, F. M., et al., 1982. *J. Exp. Med.* 155: 1555–XXXX.

Van-Riper, G., S. Sicilianl, P. A. fischer, R. Meurer, M. S. Springer, et al., 1993. *J. Exp. Med.* 177: 851–856.

Vassalli, P. 1992. *Annu. Rev. Immunol.* 10: 411–452.

Via, C. S., et al., 1988. *Immunol. Today* 9: 207–212.

Vieira, J. and J. Messing 1982. *Gene* 19: 259–268.

Vieiva, P. et al., 1991. *Proc. Natl. Acad. Sci. USA* 88, 1172–1176.

Visvanathan, K. V. and S. Goodbourn 1989. *EMBO J.* 8: 1129–1138.

Vitetta, E. S., et al., 1985. *J. Exp. Med.* 162: 1726–XXXX.

Walter, M. R., et al., 1992. *J. Biol. Chem.* 267: 20371–20376.

Wang, J. M., D. W. McVicar, J. J. Oppenheim and D. J. Kelvin, 1993. *J. Exp. Med.* 177: 699–705.

Wheelock, E. F., 1965. *Science* 149: 310–311.

Widmer, M. B., Grabstein, K. H. 1987. *Nature* 326: 795–XXX.

Wiedermann, C. J., E. kowald, N. Reinisch, C. M. Kaehler, I. von-Luettichau, et al., 1993. *Current Biology* 3: 735–739.

Williams, R. O., M. Feldmann and R. N. Maini, 1992. *Proc. Natl. Acad. Sci. USA* 89: 9784–9788.

Yokota, T., et al., 1986. *Proc. Natl. Acad. Sci. USA* 83: 5894–5898.

We claim:

1. A purified and isolated non-naturally occurring nucleic acid ligand to a cytokine selected from the group consisting of interleukin-4 (IL4), interleukin-10 (IL-10), tumor necrosis factor-alpha (TNF-alpha) and Regulated on Activation, Normal T-cell Expressed and Secreted (RANTES) protein.

2. The purified and isolated non-naturally occurring nucleic acid ligand of claim 1 wherein said nucleic acid ligand is single-stranded.

3. The purified and isolated non-naturally occurring nucleic acid ligand of claim 2 wherein said nucleic acid ligand is RNA.

4. The purified and isolated non-naturally occurring nucleic acid ligand of claim 2 wherein said nucleic acid ligand is DNA.

5. A nucleic acid ligand to a cytokine selected from the group consisting of IL-4, IL-10, TNF-α and RANTES, identified according to the method comprising:
   a) preparing a candidate mixture of nucleic acids;
   b) contacting the candidate mixture of nucleic acids with said cytokine, wherein nucleic acids having an increased affinity to said cytokine relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acid sequences with relatively higher affinity and specificity for binding to said cytokine, whereby a nucleic acid ligand of said cytokine may be identified.

6. The purified and isolated non-naturally occuring RNA ligand to IFN-gamma of claim 5 wherein said ligand is selected from the group consisting of the sequences set forth in Tables 3 and 4 (SEQ ID NOS: 7–73).

7. The purified and isolated non-naturally occurring RNA ligand of claim 3 wherein said ligand is to IL-4.

8. The purified and isolated non-naturally occurring RNA ligand to IL-4 of claim 7 wherein said ligand is selected from the group consisting of the sequences set forth in Tables 7 and 8 (SEQ ID NOS: 79–185).

9. The purified and isolated non-naturally occurring RNA ligand to IL-4 of claim 7 wherein said ligand is substantially homologous to and has substantially the same ability to bind IL-4 as a ligand selected from the group consisting of the sequences set forth in Tables 7 and 8 (SEQ ID NOS: 79–185).

10. The purified and isolated non-naturally occurring RNA ligand to IL-4 of claim 7 wherein said ligand has substantially the same structure and substantially the same ability to bind IL-4 as a ligand selected from the group consisting of the sequences set forth in Tables 7 and 8 (SEQ ID NOS:79–185).

11. The purified and isolated non-naturally occurring RNA ligand of claim 3 wherein said ligand is to IL-10.

12. The purified and isolated non-naturally occurring RNA ligand to IL-10 of claim 11 wherein said ligand is selected from the group consisting of the sequences set forth in Table 10 (SEQ ID NOS: 189–205).

13. The purified and isolated non-naturally occurring RNA ligand to IL-10 of claim 11 wherein said ligand is substantially homologous to and has substantially the same ability to bind IL-10 as a ligand selected from the group consisting of the sequences set forth in Table 10 (SEQ ID NOS: 189–205).

14. The purified and isolated non-naturally occurring RNA ligand to IL-10 of claim 11 wherein said ligand has substantially the same structure and substantially the same ability to bind IL-10 as a ligand selected from the group consisting of the sequences set forth in Table 10 (SEQ ID NOS: 189–205).

15. The purified and isolated non-naturally occuring RNA ligand of claim 3 wherein said ligand id to TNF-alpha.

16. The purified and isolated non-naturally occurring RNA ligand to TNF-alpha of claim 15 wherein said ligand is selected from the group consisting of the sequences set forth in Table 12 (SEQ ID NOS: 209–255).

17. The purified and isolated non-naturally occurring RNA ligand to TNF-alpha of claim 15 wherein said ligand is substantially homologous to and has substantially the same ability to bind TNF-alpha as a ligand selected from the group consisting of the sequences set forth in Table 12 (SEQ ID NOS:209–255).

18. The purified and isolated non-naturally occurring RNA ligand to TNF-alpha of claim 15 wherein said ligand has substantially the same structure and substantially the same ability to bind TNF-alpha as a ligand selected from the group consisting of the sequences set forth in Table 12 (SEQ ID NOS: 189–205).

19. The purified and isolated non-naturally occurring nucleic acid ligand of claim 1 wherein said ligand is to RANTES.

* * * * *

SEQUENCE LISTING (1) GENERAL INFORMATION:

(iii) NUMBER OF SEQUENCES: 258

(2) INFORMATION FOR SEQ ID NO: 1:

(i) SEQUENCE CHARACTERISTICS:
       (A) LENGTH: 71 base pairs
       (B) TYPE: nucleic acid
       (C) STRANDEDNESS: single
       (D) TOPOLOGY: linear (ii) MOLECULE TYPE: RNA (xi) SEQUENCE DESCRIPTION: SEQ ID NO: 1:

GGGAGGACGA UGCGGNNNNN NNNNNNNNNN NNNNNNNNNN NNNNNNNNNN          50

NNNNNCAGAC GACUCGCCCG A                                         71

(2) INFORMATION FOR SEQ ID NO: 2:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 2:

TAATACGACT CACTATAGGG AGGACGATGC GG                             32

(2) INFORMATION FOR SEQ ID NO: 3:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 3:

TCGGGCGAGT CGTCTG                                               16

(2) INFORMATION FOR SEQ ID NO: 4:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 4:

CCGAAGCTTA ATACGACTCA CTATAGGGAG GACGATGCGG                     40

(2) INFORMATION FOR SEQ ID NO: 5:

(i) SEQUENCE CHARACTERISTICS:
       (A) LENGTH: 25 base pairs
       (B) TYPE: nucleic acid
       (C) STRANDEDNESS: single
       (D) TOPOLOGY: linear

```
     (ii) MOLECULE TYPE: DNA (xi) SEQUENCE DESCRIPTION: SEQ ID NO: 5:

GCCGGATCCT CGGGCGAGTC GTCTG                                                  25

(2) INFORMATION FOR SEQ ID NO: 6:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 6:

AGTCACGACG TTGTAAAACG ACGGCCAGTG                                             30

(2) INFORMATION FOR SEQ ID NO: 7:

(i) SEQUENCE CHARACTERISTICS:
          (A) LENGTH: 71 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-F
               modified (xi) SEQUENCE DESCRIPTION: SEQ ID NO: 7:

GGGAGGACGA UGCGGACACC GUUAAUCUGA GGCCCUGUCC UAUUCCUUCA                       50

CGCCUCAGAC GACUCGCCCG A                                                     71

(2) INFORMATION FOR SEQ ID NO: 8:

(i) SEQUENCE CHARACTERISTICS:
          (A) LENGTH: 71 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-F
               modified (xi) SEQUENCE DESCRIPTION: SEQ ID NO: 8:

GGGAGGACGA UGCGGACACC GUUAGUCUGA GGCCUUGUCC UAUUCCUUCA                       50

CGCCUCAGAC GACUCGCCCG A                                                     71

(2) INFORMATION FOR SEQ ID NO: 9:

(i) SEQUENCE CHARACTERISTICS:
          (A) LENGTH: 71 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-F
               modified
```

```
        (xi) SEQUENCE DESCRIPTION:  SEQ ID NO: 9:

GGGAGGACGA UGCGGACACC UUUAAUCUGA GGCCCUGUCC UAUUCCUUCA           50

CGCCUCAGAC GACUCGCCCG A                                         71

(2) INFORMATION FOR SEQ ID NO: 10:

(i) SEQUENCE CHARACTERISTICS:
            (A) LENGTH:  71 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F
                modified (xi) SEQUENCE DESCRIPTION:  SEQ ID NO: 10:

GGGAGGACGA UGCGGACACC UUGAAUCUGA GGCCCUGUCC UAUUCCUUCA            50

CGCCUCAGAC GACUCGCCCG A                                          71

(2) INFORMATION FOR SEQ ID NO: 11:

(i) SEQUENCE CHARACTERISTICS:
            (A) LENGTH: 71 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F
                modified (xi) SEQUENCE DESCRIPTION:  SEQ ID NO: 11:

GGGAGGACGA UGCGGACACC GUUAAUCUGA GGCCCUGUCC UAUUCCUCCA            50

CGCCUCAGAC GACUCGCCCG A                                          71

(2) INFORMATION FOR SEQ ID NO: 12:

(i) SEQUENCE CHARACTERISTICS:
            (A) LENGTH:  71 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F
                modified (xi) SEQUENCE DESCRIPTION:  SEQ ID NO: 12:

GGGAGGACGA UGCGGACACC GUAGAUCUGA GGCCCUGUCC UAUUCCUCCA            50

CGCCUCAGAC GACUCGCCCG A                                          71

(2) INFORMATION FOR SEQ ID NO: 13:

(i) SEQUENCE CHARACTERISTICS:
            (A) LENGTH:  70 base pairs
            (B) TYPE:  nucleic acid
            (C) STRANDEDNESS:  single
            (D) TOPOLOGY:  linear
```

(ii) MOLECULE TYPE: RNA (ix) FEATURE:
              (D) OTHER INFORMATION: All pyrimidines are 2'-F
                  modified (xi) SEQUENCE DESCRIPTION: SEQ ID NO: 13:

GGGAGGACGA UGCGGACACC GUUAAUCUGA GGCCCUGUCC AUUCCUUCAC             50

GCCUCAGACG ACUCGCCCGA                                             70

(2) INFORMATION FOR SEQ ID NO: 14:

(i) SEQUENCE CHARACTERISTICS:
              (A) LENGTH: 71 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F
                  modified (xi) SEQUENCE DESCRIPTION: SEQ ID NO: 14:

GGGAGGACGA UGCGGACACC GUUAAACUGA GGCCCUGUCC UAUUCCUUCA             50

CGCCUCAGAC GACUCGCCCG A                                           71

(2) INFORMATION FOR SEQ ID NO: 15:

(i) SEQUENCE CHARACTERISTICS:
              (A) LENGTH: 72 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F
                  modified (xi) SEQUENCE DESCRIPTION: SEQ ID NO: 15:

GGGAGGACGA UGCGGAACAC CCCCGGUCUG ACGCUUGUUC CGAAUUCCUC             50

CACCGUCAGA CGACUCGCCC GA                                          72

(2) INFORMATION FOR SEQ ID NO: 16:

(i) SEQUENCE CHARACTERISTICS:
              (A) LENGTH: 73 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F
                  modified (xi) SEQUENCE DESCRIPTION: SEQ ID NO: 16:

GGGAGGACGA UGCGGGAACA CCCCCGGUCU GACGCUUGUU CCGAAUUCCU             50

CCACCGUCAG ACGACUCGCC CGA                                         73

(2) INFORMATION FOR SEQ ID NO: 17:

(i) SEQUENCE CHARACTERISTICS:

(A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 17:

GGGAGGACGA UGCGGAACAC CCCGGUCUGA CGCUUGUUCC GAAUUCCUCC          50

ACCGUCAGAC GACUCGCCCG A                                        71

(2) INFORMATION FOR SEQ ID NO: 18:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 18:

GGGAGGACGA UGCGGAACAC CCCCGGUUUG ACGCUUGUUC CGAAAUCCUC          50

CACCGUCAGA CGACUCGCCC GA                                       72

(2) INFORMATION FOR SEQ ID NO: 19:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 19:

GGGAGGACGA UGCGGAACAC CCCCGGUCUG ACGCUUGUUC CGAAUCCUCC          50

ACCGUCAGAC GACUCGCCCG A                                        71

(2) INFORMATION FOR SEQ ID NO: 20:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified

```
        (xi) SEQUENCE DESCRIPTION: SEQ ID NO: 20:

GGGAGGACGA UGCGGGGUUC CUGUUCUACU UUCUAAUUAU CCGCACCUCC          50

UCCUCAGACG ACUCGCCCGA                                          70

(2) INFORMATION FOR SEQ ID NO: 21:

(i) SEQUENCE CHARACTERISTICS:
          (A) LENGTH: 71 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-F
              modified (xi) SEQUENCE DESCRIPTION: SEQ ID NO: 21:

GGGAGGACGA UGCGGUGGAG UUUUAAUCUU ACUUCCUACU CUUGCUCCAC          50

UGGGUCAGAC GACUCGCCCG A                                        71

(2) INFORMATION FOR SEQ ID NO: 22:

(i) SEQUENCE CHARACTERISTICS:
          (A) LENGTH: 71 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-F
              modified (xi) SEQUENCE DESCRIPTION: SEQ ID NO: 22:

GGGAGGACGA UGCGGGAUUC AUUUUGAUCU UUCUUUCUCU UAUCCCGCUG          50

UGCCUCAGAC GACUCGCCCG A                                        71

(2) INFORMATION FOR SEQ ID NO: 23:

(i) SEQUENCE CHARACTERISTICS:
          (A) LENGTH: 72 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-F
              modified (xi) SEQUENCE DESCRIPTION: SEQ ID NO: 23:

GGGAGGACGA UGCGGAUUCC UUUUUCCUUU CUCUUUUCUG ACCGACUGAU          50

CCGCCUCAGA CGACUCGCCC GA                                       72

(2) INFORMATION FOR SEQ ID NO: 24:

(i) SEQUENCE CHARACTERISTICS:
          (A) LENGTH: 75 base pairs
          (B) TYPE: nucleic acid
          (C) STRANDEDNESS: single
          (D) TOPOLOGY: linear
```

(ii) MOLECULE TYPE: RNA (ix) FEATURE:
    (D) OTHER INFORMATION: All pyrimidines are 2'-F
        modified (xi) SEQUENCE DESCRIPTION: SEQ ID NO: 24:

GGGAGGACGA UGCGGUAAUC UACACUUAUA UUUUUUUUCU UUUUCUUUCC          50

ACCCAUCGUC AGACGACUCG CCCGA                                    75

(2) INFORMATION FOR SEQ ID NO:25:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 25:

GGGAGGACGA UGCGGAGGGU UGGGAGGGGU CCUUCUUUUC GUCUGCGUGG          50

ACCGUCAGAC GACUCGCCCG A                                        71

(2) INFORMATION FOR SEQ ID NO: 26:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 26:

GGGAGGACGA UGCGGCAUCC CUAGAGCAGC CAGCCGGAAA GAAGUCACGC          50

CUGCUCAGAC GACUCGCCCG A                                        71

(2) INFORMATION FOR SEQ ID NO: 27:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 27:

GGGAGGACGA UGCGGUAGUG ACCGUCAGGU AGGUGGGUUA GGCCAUUACG          50

UACGUCAGAC GACUCGCCCG A                                        71

(2) INFORMATION FOR SEQ ID NO: 28:

(i) SEQUENCE CHARACTERISTICS:

(A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 28:

GGGAGGACGA UGCGGGUGCC AACAAUGGAG GUCGGGUUAG GUAAGCCAAC          50

GGGUCAGACG ACUCGCCCGA                                           70

(2) INFORMATION FOR SEQ ID NO: 29:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2
            modified (xi) SEQUENCE DESCRIPTION:  SEQ ID NO: 29:

GGGAGGACGA UGCGGUAGUA GCGCGAUAUA GCGCUGGUAG GGUUGCCGGU          50

GGAUCAGACG ACUCGCCCGA                                           70

(2) INFORMATION FOR SEQ ID NO: 30:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2
            modified (xi) SEQUENCE DESCRIPTION:  SEQ ID NO: 30:

GGGAGGACGA UGCGGUAGUA GCGCGAUAUA GCGCUGGUAG GGUAGCCGGU          50

GAUCAGACGA CUCGCCCGA                                            69

(2) INFORMATION FOR SEQ ID NO: 31:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2
            modified (xi) SEQUENCE DESCRIPTION: SEQ ID NO: 31:

GGGAGGACGA UGCGGUUGUA GCGCGAUAUA GCGCUGGUAG GGUUGCCGGU          50

GGAUCAGACG ACUCGCCCGA          70

(2) INFORMATION FOR SEQ ID NO: 32:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 32:

GGGAGGACGA UGCGGUGGUA GCGCGAUAUA GCGCUGGUAG GGUAGCCGGU          50

GAUCAGACGA CUCGCCCGA          69

(2) INFORMATION FOR SEQ ID NO: 33:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 33:

GGGAGGACGA UGCGGUGGUA GCGCGAUAUA GCGCUGGUAG GGUUGCCGGU          50

GAUCAGACGA CUCGCCCGA          69

(2) INFORMATION FOR SEQ ID NO: 34:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 34:

GGGAGGACGA UGCGGUUGUA GCGCGAUAUA GCGCUGGUAG GGUUGCCGGU          50

GAUCAGACGA CUCGCCCGA          69

(2) INFORMATION FOR SEQ ID NO: 35:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
             (D) OTHER INFORMATION: All pyrimidines are 2'-NH2
                 modified (xi) SEQUENCE DESCRIPTION: SEQ ID NO: 35:

GGGAGGACGA UGCGGUGGUA GCGCGAUAUA GCGCUGGUAG GGUUGCCGGU            50

GGGUCAGACG ACUCGCCCGA                                             70

(2) INFORMATION FOR SEQ ID NO: 36:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All pyrimidines are 2'-NH2
                 modified (xi) SEQUENCE DESCRIPTION: SEQ ID NO: 36:

GGGAGGACGA UGCGGUUGUA GCGCGAUAUA GCGCUGGCAG GGUUGCCGGU            50

GGGUCAGACG ACUCGCCCGA                                             70

(2) INFORMATION FOR SEQ ID NO: 37:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All pyrimidines are 2'-NH2
                 modified (xi) SEQUENCE DESCRIPTION: SEQ ID NO: 37:

GGGAGGACGA UGCGGUGGCA GCGCGAGAUA GCGCUGGUAG GGUUGCCGGU            50

GGAUCAGACG ACUCGCCCGA                                             70

(2) INFORMATION FOR SEQ ID NO: 38:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All pyrimidines are 2'-NH2
                 modified (xi) SEQUENCE DESCRIPTION: SEQ ID NO: 38:

GGGAGGACGA UGCGGUGGUA GCGCGACAUA GCGCUGGUAG GGUUGCCGGU            50

GAUCAGACGA CUCGCCCGA                                              69

(2) INFORMATION FOR SEQ ID NO: 39:

(i) SEQUENCE CHARACTERISTICS:

(A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 39:

GGGAGGACGA UGCGGAAGUG GUGAUCCCAU CUAGGGGUCG GUUGGGUCGA        50

CGGUGCAGAC GACUCGCCCG A        71

(2) INFORMATION FOR SEQ ID NO: 40:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 40:

GGGAGGACGA UGCGGUGUGU GGGGUGCCAU AUAACCCCGG UUGGGUUGAC        50

GGUGUCAGAC GACUCGCCCG A        71

(2) INFORMATION FOR SEQ ID NO: 41:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 41:

GGGAGGACGA UGCGGUAGUG CUCACAGAGC GGUUGGGUAG CCGGUGGAUG        50

CGGUCAGACG ACUCGCCCGA        70

(2) INFORMATION FOR SEQ ID NO: 42:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 42:

GGGAGGACGA UGCGGUGUGG UGCAAUCUAA GCACCGGUUG GGUAGUUCGG            50

UGGCUCAGAC GACUCGCCCG A                                          71

(2) INFORMATION FOR SEQ ID NO:43:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 43:

GGGAGGACGA UGCGGAGGCU CAAAAGGCCG GUUGGGUUAG GUAACUGUGU            50

GCGGUCAGAC GACUCGCCCG A                                          71

(2) INFORMATION FOR SEQ ID NO: 44:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 44:

GGGAGGACGA UGCGGUAUGG UGGGUUUACG CGAGAGUAAG GGUCGCGUGG            50

UCAGACGACU CGCCCGA                                               67

(2) INFORMATION FOR SEQ ID NO: 45:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 45:

GGGAGGACGA UGCGGACGUA UGGUGGGUUC GUAGUAUUGG GCUCGUAGCG            50

UGGGUCAGAC GACUCGCCCG A                                          71

(2) INFORMATION FOR SEQ ID NO: 46:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO: 46:

GGGAGGACGA UGCGGCAGGU AAUUACAUGA AGGUGGGUUA GGUACUUUCA          50

GGGUCAGACG ACUCGCCCGA                                          70

(2) INFORMATION FOR SEQ ID NO: 47:

(i) SEQUENCE CHARACTERISTICS:
            (A) LENGTH:  70 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO: 47:

GGGAGGACGA UGCGGUAGGU AAUUACAUGA AGGUGGGUUA GGUACUUUCA          50

GGGUCAGACG ACUCGCCCGA                                          70

(2) INFORMATION FOR SEQ ID NO: 48:

(i) SEQUENCE CHARACTERISTICS:
            (A) LENGTH:  71 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO: 48:

GGGAGGACGA UGCGGCAGUA AAUUCGUAG GUGGGUUAGG UAGGAUCGUG           50

AGGGUCAGAC GACUCGCCCG A                                        71

(2) INFORMATION FOR SEQ ID NO: 49:

(i) SEQUENCE CHARACTERISTICS:
            (A) LENGTH:  71 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO:49:

GGGAGGACGA UGCGGUAUGG UGGGUUGCAC GUAUUAAGGG ACGUACAUCU          50

GUGCUCAGAC GACUCGCCCG A                                        71

(2) INFORMATION FOR SEQ ID NO: 50:

(i) SEQUENCE CHARACTERISTICS:

(A) LENGTH:  77 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2
            modified (xi) SEQUENCE DESCRIPTION:  SEQ ID NO: 50:

GGGAGGACGA UGCGGUAUAG GUAACUAUCA GGUGGGUAGU CGGUGGAAAC          50

GGGCUGUUGG UCAGACGACU CGCCCGA                                  77

(2) INFORMATION FOR SEQ ID NO: 51:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2
            modified (xi) SEQUENCE DESCRIPTION:  SEQ ID NO: 51:

GGGAGGACGA UGCGGUACAG GUGGGUCGUG GAUAAUUGGG CACGCUCUAU          50

CUCCUCAGAC GACUCGCCCG A                                        71

(2) INFORMATION FOR SEQ ID NO: 52:

(i) SEQUENCE CHARACTERISTICS:
        (A) LENGTH: 71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2
            modified (xi) SEQUENCE DESCRIPTION:  SEQ ID NO: 52:

GGGAGGACGA UGCGGCACUA GGUGGGUCGU GGUUGUUGGG CACGUAACUU          50

CGCGUCAGAC GACUCGCCCG A                                        71

(2) INFORMATION FOR SEQ ID NO: 53:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2
            modified (xi) SEQUENCE DESCRIPTION: SEQ ID NO: 53:

GGGAGGACGA UGCGGUACUA GGUGGGUCGU GGUUGUUGGG CACGUAACUU            50

CGCGUCAGAC GACUCGCCCG A                                          71

(2) INFORMATION FOR SEQ ID NO: 54:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2
                modified (xi) SEQUENCE DESCRIPTION: SEQ ID NO: 54:

GGGAGGACGA UGCGGACGUG GCCUUAGAUA GGCAGGUGGG UUAGGCAUAU            50

UCAGUCAGAC GACUCGCCCG A                                          71

(2) INFORMATION FOR SEQ ID NO: 55:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2
                modified (xi) SEQUENCE DESCRIPTION: SEQ ID NO: 55:

GGGAGGACGA UGCGGUUCGC GGCCUAAUUA AAGGCAGGAG GGUUAGGCAU            50

UGCUCAGACG ACUCGCCCGA                                            70

(2) INFORMATION FOR SEQ ID NO: 56:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2
                modified (xi) SEQUENCE DESCRIPTION: SEQ ID NO: 56:

GGGAGGACGA UGCGGUGACU ACGCCUGUAG UAGGUCGGGU UAGGCAUUGG            50

GCGUCAGACG ACUCGCCCGA                                            70

(2) INFORMATION FOR SEQ ID NO: 57:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: RNA (ix) FEATURE:
    (D) OTHER INFORMATION: All pyrimidines are 2'-NH2
        modified (xi) SEQUENCE DESCRIPTION: SEQ ID NO: 57:

GGGAGGACGA UGCGGUGCGC AAUUGCGCAG GUCGGGUUAG GUAUCUGGGU          50

AGCUCAGACG ACUCGCCCGA                                          70

(2) INFORMATION FOR SEQ ID NO: 58:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 58:

GGGAGGACGA UGCGGUUCAG AGGGUAGGUA AGUGGGAGGA AAAAUGCCGU          50

AUCGCCUCAG ACGACUCGCC CGA                                      73

(2) INFORMATION FOR SEQ ID NO: 59:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 59:

GGGAGGACGA UGCGGAGGUA AGAGGGAGGG ACCUUCCAGU GAAUGUGCGC          50

GUGGUCAGAC GACUCGCCCG A                                        71

(2) INFORMATION FOR SEQ ID NO: 60:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 60:

GGGAGGACGA UGCGGAGGCC UGUGGUGAGG AUUGUGGGUG GUUGGCCACG          50

CGCGUCAGAC GACUCGCCCG A                                         71

(2) INFORMATION FOR SEQ ID NO: 61:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 61:

GGGAGGACGA UGCGGUCCAA AGAGGGUGGU UGUGGGUGGC ACUAAGGUAC          50

CGCGUCAGAC GACUCGCCCG A                                         71

(2) INFORMATION FOR SEQ ID NO: 62:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 62:

GGGAGGACGA UGCGGUAUUC GUAAGGCCAG AGCUGCGGGU GGGACCUCCG          50

GCCUCAGACG ACUCGCCCGA                                           70

(2) INFORMATION FOR SEQ ID NO: 63:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 63:

GGGAGGACGA UGCGGCCAUA GUGGGUGGGU UUGGAGUGGA AUAGUGCCGA          50

GCGUCAGACG ACUCGCCCGA                                           70

(2) INFORMATION FOR SEQ ID NO: 64:

(i) SEQUENCE CHARACTERISTICS:

```
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 64:

GGGAGGACGA UGCGGUGCAC AUGAGGGUGG UGUGGGAGGA AACGUGACGC          50

AUGGUCAGAC GACUCGCCCG A                                        71

(2) INFORMATION FOR SEQ ID NO: 65:

(i) SEQUENCE CHARACTERISTICS:
        (A) LENGTH: 71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 65:

GGGAGGACGA UGCGGUUCCG UCCGUGGGAU AGGUUUGUGG GAUGUACCGG          50

CUGGUCAGAC GACUCGCCCG A                                        71

(2) INFORMATION FOR SEQ ID NO: 66:

(i) SEQUENCE CHARACTERISTICS:
        (A) LENGTH:  59 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 66:

GGGAGGACGA UGCGGACACC GUUAAUCUGA GGCCCUGUCC UAUUCCUUCA          50

CGCCUCAGA                                                      59

(2) INFORMATION FOR SEQ ID NO: 67:

(i) SEQUENCE CHARACTERISTICS:
        (A) LENGTH:  46 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified
```

(xi) SEQUENCE DESCRIPTION: SEQ ID NO: 67:

GUUUUAAUCU UACUUCCUAC UCUUGCUCCA CUGGGUCAGA CGACUC                          46

(2) INFORMATION FOR SEQ ID NO: 68:

(i) SEQUENCE CHARACTERISTICS:
             (A) LENGTH: 57 base pairs
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-F
                 modified (xi) SEQUENCE DESCRIPTION: SEQ ID NO: 68:

GGGAGGACGA UGCGGCAUCC CUAGAGCAGC CAGCCGGAAA GAAGUCACGC                      50

CUGCUCA                                                                    57

(2) INFORMATION FOR SEQ ID NO: 69:

(i) SEQUENCE CHARACTERISTICS:
             (A) LENGTH: 64 base pairs
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-F
                 modified (xi) SEQUENCE DESCRIPTION: SEQ ID NO: 69:

GGGAGGACGA UGCGGAACAC CCCCGGUCUG ACGCUUGUUC CGAAUUCCUC                      50

CACCGUCAGA CGAC                                                            64

(2) INFORMATION FOR SEQ ID NO: 70:

(i) SEQUENCE CHARACTERISTICS:
             (A) LENGTH: 37 base pairs
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-F
                 modified (xi) SEQUENCE DESCRIPTION: SEQ ID NO: 70:

GGGAGGACGA UGCGGAGGGU UGGGAGGGGU CCUUCUU                                    37

(2) INFORMATION FOR SEQ ID NO: 71:

(i) SEQUENCE CHARACTERISTICS:
             (A) LENGTH: 51 base pairs
             (B) TYPE: nucleic acid
             (C) STRANDEDNESS: single
             (D) TOPOLOGY: linear (ii) MOLECULE TYPE: RNA

```
    (ix) FEATURE:
          (D) OTHER INFORMATION: All pyrimidines are 2'-NH2
              modified (xi) SEQUENCE DESCRIPTION: SEQ ID NO: 71:

GGGAGGACGA UGCGGUGGUA GCGCGAUAUA GCGCUGGUAG GGUUGCCGGU        50

G                                                              51

(2) INFORMATION FOR SEQ ID NO: 72:

(i) SEQUENCE CHARACTERISTICS:
          (A) LENGTH: 44 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-NH2
              modified (xi) SEQUENCE DESCRIPTION: SEQ ID NO: 72:

GGGAGGACGA UGCGGCAGGU AAUUACAUGA AGGUGGGUUA GGUA              44

(2) INFORMATION FOR SEQ ID NO: 73:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All U's are 2'-NH2 modified (ix) FEATURE:
          (D) OTHER INFORMATION: All C's are 2'-F modified (xi) SEQUENCE DESCRIPTION: SEQ ID NO: 73:

GGACGAUGCG GUUCAGAGGG UAGGUAAGUG GGAGGAAAAA UGCCGUAUCG        50

(2) INFORMATION FOR SEQ ID NO: 74:

(i) SEQUENCE CHARACTERISTICS:
          (A) LENGTH: 87 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 74:

GGGAGACAAG AATAAACGCT CAANNNNNNN NNNNNNNNNN NNNNNNNNNN        50

NNNNNNNNNN NNNTTCGACA GGAGGCTCAC AACAGGC                      87

(2) INFORMATION FOR SEQ ID NO: 75:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: DNA
```

(xi) SEQUENCE DESCRIPTION: SEQ ID NO: 75:

TAATACGACT CACTATAGGG AGACAAGAAT AAACGCTCAA                       40

(2) INFORMATION FOR SEQ ID NO: 76:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 76:

GCCTGTTGTG AGCCTCCTGT CGAA                                       24

(2) INFORMATION FOR SEQ ID NO: 77:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 77:

CCGAAGCTTT AATACGACTC ACTATAGGGA GACAAGAATA AACGCTCAA            49

(2) INFORMATION FOR SEQ ID NO: 78:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 78:

GCCGGATCCG CCTGTTGTGA GCCTCCTGTC GAA                             33

(2) INFORMATION FOR SEQ ID NO: 79:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 79:

GGGAGACAAG AAUAAACGCU CAACUAUGGG GAGCCACAUU AACGGCAAUA           50

AAUCAUUACG ACUUCGACAG GAGGCUCACA ACAGGC                          86

(2) INFORMATION FOR SEQ ID NO: 80:

(i) SEQUENCE CHARACTERISTICS:
        (A) LENGTH: 89 base pairs
        (B) TYPE: nucleic acid
        (C) STRANDEDNESS: single
        (D) TOPOLOGY: linear

```
        (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 80:

GGGAGACAAG  AAUAAACGCU  CAACUAUGGG  GAGCCACAUU  UAACGGCUAU             50

AAAAAACAUU  ACGACUUCGA  CAGGAGGCUC  ACAACAGGC                          89

(2) INFORMATION FOR SEQ ID NO: 81:

(i) SEQUENCE CHARACTERISTICS:
            (A) LENGTH:  86 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 81:

GGGAGACAAG  AAUAAACGCU  CAACUCGGGA  GCCAGAGUAA  CAACGGCAUU             50

AUAUAAUUUA  CUUUCGACAG  GAGGCUCACA  ACAGGC                             86

(2) INFORMATION FOR SEQ ID NO: 82:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 82:

GGGAGACAAG  AAUAAACGCU  CAAUCCCACC  GGGGUGCCAC  GGUUUAAACG             50

GCUUAAUAUG  AAUUUCGACA  GGAGGCUCAC  AACAGGC                            87

(2) INFORMATION FOR SEQ ID NO: 83:

(i) SEQUENCE CHARACTERISTICS:
            (A) LENGTH:  85 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 83:

GGGAGACAAG  AAUAAACGCU  CAAGUCUGAC  UAUUGGGGCG  CCACAAUAUC             50

AACGGCUGUA  CUUCGACAGG  AGGCUCACAA  CAGGC                              85

(2) INFORMATION FOR SEQ ID NO: 84:

(i) SEQUENCE CHARACTERISTICS:
```

(A) LENGTH:  88 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F
                modified (xi) SEQUENCE DESCRIPTION:  SEQ ID NO: 84:

GGGAGACAAG AAUAAACGCU CAAUCCCACC GGGGUGCCAC GGUUUAAACG            50

GCUUAAUAUU UACUUUCGAC AGGAGGCUCA CAACAGGC                         88

(2) INFORMATION FOR SEQ ID NO: 85:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F
                modified (xi) SEQUENCE DESCRIPTION:  SEQ ID NO: 85:

GGGAGACAAG AAUAAACGCU CAAGUCUUCC AUGGGGAGCC ACAUUAACGG            50

CGCAAUACUG AACUUCGACA GGAGGCUCAC AACAGGC                          87

(2) INFORMATION FOR SEQ ID NO: 86:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F
                modified (xi) SEQUENCE DESCRIPTION:  SEQ ID NO: 86:

GGGAGACAAG AAUAAACGCU CAACUCGGGA GCCAGAGUAA CAACGGCACU            50

AUAUAAUUUU ACUUUCGACA GGAGGCUCAC AACAGGC                          87

(2) INFORMATION FOR SEQ ID NO: 87:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F
                modified (xi) SEQUENCE DESCRIPTION: SEQ ID NO: 87:

GGGAGACAAG AAUAAACGCU CAACUAUGGG GAGCCACAUU UAACGGCAAU          50

AAAUCAUUAC GACUUCGACA GGAGGCUCAC AACAGGC                        87

(2) INFORMATION FOR SEQ ID NO: 88:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 88:

GGGAGACAAG AAUAAACGCU CAAAGUGGGG AGCCACACUA AAACGGCAUA          50

UUGACAUCGU CCCUUCGACA GGAGGCUCAC AACAGGC                        87

(2) INFORMATION FOR SEQ ID NO: 89:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 89:

GGGAGACAAG AAUAAACGCU CAAUCUCCUC AUGGGGCGCC ACAUGGUUUU          50

AACGGCAUAU CACUUUCGAC AGGAGGCUCA CAACAGGC                       88

(2) INFORMATION FOR SEQ ID NO: 90:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 90:

GGGAGACAAG AAUAAACGCU CAACUAUGGG GAGCCACAUU UAACGGCUAU          50

AAAUCAUUAC GACUUCGACA GGAGGCUCAC AACAGGC                        87

(2) INFORMATION FOR SEQ ID NO: 91:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 91:

GGGAGACAAG AAUAAACGCU CAAACUGGGG AGCCACAGAU UUAACGGCGC         50

AUAUGAGUUG AGCUUCGACA GGAGGCUCAC AACAGGC                      87

(2) INFORMATION FOR SEQ ID NO: 92:

(i) SEQUENCE CHARACTERISTICS:
             (A) LENGTH:  86 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 92:

GGGAGACAAG AAUAAACGCU CAACUCUCAC UGGGGAGCCA CAGUUUUAAA         50

CGGCAAGGGA GAUUCGACAG GAGGCUCACA ACAGGC                       86

(2) INFORMATION FOR SEQ ID NO: 93:

(i) SEQUENCE CHARACTERISTICS:
             (A) LENGTH:  84 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 93:

GGGAGACAAG AAUAAACGCU CAACAUCAGA UGGGGUGCCA CAUCAUCAAA         50

CGGCUAUAUA UUCGACAGGA GGCUCACAAC AGGC                         84

(2) INFORMATION FOR SEQ ID NO: 94:

(i) SEQUENCE CHARACTERISTICS:
             (A) LENGTH:  86 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 94:

GGGAGACAAG AAUAAACGCU CAAACUGGGG AGCCACAGAU UUAACGGCAC         50

AUAUGAUUGA GCUUCGACAG GAGGCUCACA ACAGGC                       86

(2) INFORMATION FOR SEQ ID NO: 95:

(i) SEQUENCE CHARACTERISTICS:

(A) LENGTH: 89 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 95:

GGGAGACAAG AAUAAACGCU CAAAACGGCU GUAACAAACA AGGUGGGGGG               50

CCACACCAGA GCGGCUUCGA CAGGAGGCUC ACAACAGGC                          89

(2) INFORMATION FOR SEQ ID NO: 96:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 96:

GGGAGACAAG AAUAAACGCU CAAACGGCUG UAACAAACAA GGUGGGGGGC               50

CACACAGAGC GGGUUCGACU UCGACAGGAG GCUCACAACA GGC                     93

(2) INFORMATION FOR SEQ ID NO: 97:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 97:

GGGAGACAAG AAUAAACGCU CAAACGGCUG UGACAAACAA GGUGGGGGGC               50

CACACAGAGC GGGUUCGACA GGAGGCUCAC AACAGGC                            87

(2) INFORMATION FOR SEQ ID NO: 98:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 98:

GGGAGACAAG AAUAAACGCU CAAAUAGCAG AGCCCAUGGC GGGAGGGAGG          50

AUUGUGGUGG AAUUCGACAG GAGGCUCACA ACAGGC                        86

(2) INFORMATION FOR SEQ ID NO: 99:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 99:

GGGAGACAAG AAUAAACGCU CAACAUCGAC GGACCAGAGG UAGUGGGGGG          50

GAUGGGAUGC CGUUCGACA GGAGGCUCAC AACAGGC                        87

(2) INFORMATION FOR SEQ ID NO: 100:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 100:

GGGAGACAAG AAUAAACGCU CAAACCUAAC AUCUUACCAU AUUCAAUUUA          50

CAUUACACAC UAUUUCGACA GGAGGCUCAC AACAGGC                       87

(2) INFORMATION FOR SEQ ID NO: 101:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 101:

GGGAGACAAG AAUAAACGCU CAAGCUGCCC AAGGAAUUUA ACUUGGACCG          50

CGAUCUGGAG UCUUCGACAG GAGGCUCACA ACAGGC                        86

(2) INFORMATION FOR SEQ ID NO: 102:

(i) SEQUENCE CHARACTERISTICS:
        (A) LENGTH: 87 base pairs
        (B) TYPE: nucleic acid
        (C) STRANDEDNESS: single
        (D) TOPOLOGY: linear

```
        (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 102:

GGGAGACAAG AAUAAACGCU CAAAGGAGCG CCAUGAAGCA AAGGGAGGAU              50

UGUGGUGGAA GGCUUCGACA GGAGGCUCAC AACAGGC                           87

(2) INFORMATION FOR SEQ ID NO: 103:

(i) SEQUENCE CHARACTERISTICS:
             (A) LENGTH:  80 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 103:

GGGAGACAAG AAUAAACGCU CAACCGUAUU AACACUUAUU UUACAAUUUU              50

UUCAUAUUCG ACAGGAGGCU CACAACAGGC                                   80

(2) INFORMATION FOR SEQ ID NO: 104:

(i) SEQUENCE CHARACTERISTICS:
             (A) LENGTH:  87 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 104:

GGGAGACAAG AAUAAACGCU CAAGGUACGA CCAAGGAAUG UGGGUGGAAG              50

AGGGUGCCGU ACCUUCGACA GGAGGCUCAC AACAGGC                           87

(2) INFORMATION FOR SEQ ID NO: 105:

(i) SEQUENCE CHARACTERISTICS:
             (A) LENGTH:  87 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 105:

GGGAGACAAG AAUAAACGCU CAAGACGAAC GACCACGGGA UGGGUGGGCA              50

AAUAGGGAUG CCGUUCGACA GGAGGCUCAC AACAGGC                           87

(2) INFORMATION FOR SEQ ID NO: 106:

(i) SEQUENCE CHARACTERISTICS:
```

(A) LENGTH:  86 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 106:

GGGAGACAAG AAUAAACGCU CAAGCUAACC CGUACAAAUU UUCUUUUUCA         50

UUUUCAUCAC UAUUCGACAG GAGGCUCACA ACAGGC                        86

(2) INFORMATION FOR SEQ ID NO: 107:

(i) SEQUENCE CHARACTERISTICS:
        (A) LENGTH: 87 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 107:

GGGAGACAAG AAUAAACGCU CAACUCGGGA GCCAGAGUAA CAACGGCACU         50

AUAUAAUUUU ACCUUCGACA GGAGGCUCAC AACAGGC                       87

(2) INFORMATION FOR SEQ ID NO: 108:

(i) SEQUENCE CHARACTERISTICS:
        (A) LENGTH:  85 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION:  SEQ ID NO: 108:

GGGAGACAAG AAUAAACGCU CAACGACCCG ACCAAGGGUA GGCAUGUGGG         50

GGGGUGCCGG GUUCGACAGG AGGCUCACAA CAGGC                         85

(2) INFORMATION FOR SEQ ID NO: 109:

(i) SEQUENCE CHARACTERISTICS:
        (A) LENGTH:  87 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified (xi) SEQUENCE DESCRIPTION: SEQ ID NO: 109:

GGGAGACAAG AAUAAACGCU CAAUCCGAAC AUGGGGUGCC ACAAAAACGG          50

CUAUUAUCAC UAUUUCGACA GGAGGCUCAC AACAGGC                       87

(2) INFORMATION FOR SEQ ID NO: 110:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 110:

GGGAGACAAG AAUAAACGCU CAAGGACUGG UGAGCCACGU AUACGGUCUU          50

AGGGGCUUGG GCGUUCGACA GGAGGCUCAC AACAGGC                       87

(2) INFORMATION FOR SEQ ID NO: 111:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 111:

GGGAGACAAG AAUAAACGCU CAACCUUGUG GGGAGCCACG UAUACGGCCA          50

UAGCAUACCG CAAUUCGACA GGAGGCUCAC AACAGGC                       87

(2) INFORMATION FOR SEQ ID NO: 112:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 112:

GGGAGACAAG AAUAAACGCU CAAGAGCUGG UGAGCCACGU AUACGGCCUU          50

AGGGGCUUGG GCGUUCGACA GGAGGCUCAC AACAGGC                       87

(2) INFORMATION FOR SEQ ID NO: 113:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
 (D) OTHER INFORMATION: All pyrimidines are 2'-NH2
  modified (xi) SEQUENCE DESCRIPTION: SEQ ID NO: 113:

GGGAGACAAG AAUAAACGCU CAAGAGCUGG UGAGCCACGU AUACGGUCUU 50

AGGGGCUUGG GCGUUCGACA GGAGGCUCAC AACAGGC 87

(2) INFORMATION FOR SEQ ID NO: 114:

(i) SEQUENCE CHARACTERISTICS:
  (A) LENGTH: 87 base pairs
  (B) TYPE: nucleic acid
  (C) STRANDEDNESS: single
  (D) TOPOLOGY: linear (ii) MOLECULE TYPE: RNA (ix) FEATURE:
 (D) OTHER INFORMATION: All pyrimidines are 2'-NH2
  modified (xi) SEQUENCE DESCRIPTION: SEQ ID NO: 114:

GGGAGACAAG AAUAAACGCU CAAGUAUUGG GGAGCCACAU UACAACGGCA 50

CAGGCAACCA GGGUUCGACA GGAGGCUCAC AACAGGC 87

(2) INFORMATION FOR SEQ ID NO: 115:

(i) SEQUENCE CHARACTERISTICS:
  (A) LENGTH: 87 base pairs
  (B) TYPE: nucleic acid
  (C) STRANDEDNESS: single
  (D) TOPOLOGY: linear (ii) MOLECULE TYPE: RNA (ix) FEATURE:
 (D) OTHER INFORMATION: All pyrimidines are 2'-NH2
  modified (xi) SEQUENCE DESCRIPTION: SEQ ID NO: 115:

GGGAGACAAG AAUAAACGCU CAAGUGCUGG UGAGCCACGC AUACGGUCUU 50

AGGGGCUUGA GCGUUCGACA GGAGGCUCAC AACAGGC 87

(2) INFORMATION FOR SEQ ID NO: 116:

(i) SEQUENCE CHARACTERISTICS:
  (A) LENGTH: 86 base pairs
  (B) TYPE: nucleic acid
  (C) STRANDEDNESS: single
  (D) TOPOLOGY: linear (ii) MOLECULE TYPE: RNA (ix) FEATURE:
 (D) OTHER INFORMATION: All pyrimidines are 2'-NH2
  modified (xi) SEQUENCE DESCRIPTION: SEQ ID NO: 116:

GGGAGACAAG AAUAAACGCU CAAUAAAUGG AGAGCCACAC UAACGGCGUA 50

UGAAAACACU CAUUCGACAG GAGGCUCACA ACAGGC 86

(2) INFORMATION FOR SEQ ID NO: 117:

(i) SEQUENCE CHARACTERISTICS:

(A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 117:

GGGAGACAAG AAUAAACGCU CAAUCACAAG CACCCUUGGG GAGCCACAUU        50

AACGGCCUAG GCUUCGACAG GAGGCUCACA ACAGGC                      86

(2) INFORMATION FOR SEQ ID NO: 118:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 118:

GGGAGACAAG AAUAAACGCU CAAAUGGAGA GCCACAUUAA CGGCAGCAUA        50

UCACAGUAGG AAUUCGACAG GAGGCUCACA ACAGGC                      86

(2) INFORMATION FOR SEQ ID NO: 119:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 119:

GGGAGACAAG AAUAAACGCU CAAUGUGGGG AGCCACAGUU AACGGCUUCA        50

ACUGAUUAGA AUUCGACAGG AGGCUCACAA CAGGC                       85

(2) INFORMATION FOR SEQ ID NO: 120:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 120:

GGGAGACAAG AAUAAACGCU CAAAGAUUUA AAGUAUUUGG GGAGCCACAU         50

CAACGGCAUU GUGUUCGACA GGAGGCUCAC AACAGGC                       87

(2) INFORMATION FOR SEQ ID NO: 121:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 121:

GGGAGACAAG AAUAAACGCU CAAUGACUGA ACGAUGGUAU UGGAGAGCCA         50

CAUCAACGGC AAUUUCGACA GGAGGCUCAC AACAGGC                       87

(2) INFORMATION FOR SEQ ID NO: 122:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 122:

GGGAGACAAG AAUAAACGCU CAACAGAUGG UAUCUAGUGG AGAGCCACAU         50

CAACGGCGCA GAUUCGACAG GAGGCUCACA ACAGGC                        86

(2) INFORMATION FOR SEQ ID NO: 123:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 123:

GGGAGACAAG AAUAAACGCU CAACGAUAGU AUACACAUGA UGAUGGGGAG         50

CCACGUGUAC GGCUUCGACA GGAGGCUCAC AACAGGC                       87

(2) INFORMATION FOR SEQ ID NO: 124:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION: All pyrimidines are 2'-NH2
                modified (xi) SEQUENCE DESCRIPTION: SEQ ID NO: 124:

GGGAGACAAG AAUAAACGCU CAACGAUGGA GCGCCACAUC GCUAUAACGG        50

CAUUUAACAA AAUUUCGACA GGAGGCUCAC AACAGGC                     87

(2) INFORMATION FOR SEQ ID NO: 125:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2
                modified (xi) SEQUENCE DESCRIPTION: SEQ ID NO: 125:

GGGAGACAAG AAUAAACGCU CAAGCGGUCU GAUUGAGCCA CCGUGGAGGG        50

UACGUGGAGG GAUUCGACAG GAGGCUCACA ACAGGC                      86

(2) INFORMATION FOR SEQ ID NO: 126:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2
                modified (xi) SEQUENCE DESCRIPTION: SEQ ID NO: 126:

GGGAGACAAG AAUAAACGCU CAAACAAUUU CACACAGAAA CAGCUAUGAC        50

CAUGAUUACG CCAUUCGACA GGAGGCUCAC AACAGGC                     87

(2) INFORMATION FOR SEQ ID NO: 127:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2
                modified (xi) SEQUENCE DESCRIPTION: SEQ ID NO: 127:

GGGAGACAAG AAUAAACGCU CAAAGCUUUG GGGAGCCACA UAUAACGGCA        50

UGAUCAAAUA UAGUUCGACA GGAGGCUCAC AACAGGC                     87

(2) INFORMATION FOR SEQ ID NO: 128:

(i) SEQUENCE CHARACTERISTICS:

(A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 128:

GGGAGACAAG AAUAAACGCU CAAAUACAAU GUGGUUGAAG CUACCUCCCA         50

CUCGUAGUGG GCCUUCGACA GGAGGCUCAC AACAGGC                      87

(2) INFORMATION FOR SEQ ID NO: 129:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 129:

GGGAGACAAG AAUAAACGCU CAACCGUAGC CUCCAGCGGA ACGCGGAGGG         50

UACGUGGAGG GGUUCGACAG GAGGCUCACA ACAGGC                       86

(2) INFORMATION FOR SEQ ID NO: 130:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 130:

GGGAGACAAG AAUAAACGCU CAACCGUAGC CUCCAGCGGA AUGCGGAGGG         50

CACGUGGAGG GGUUCGACAG GAGGCUCACA ACAGGC                       86

(2) INFORMATION FOR SEQ ID NO: 131:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 131:

GGGAGACAAG AAUAAACGCU CAAGAGCCUC CGUGAAUGAC GUGGAGGCAC        50

GCGGAGGGGA AUUCGACAGG AGGCUCACAA CAGGC                        85

(2) INFORMATION FOR SEQ ID NO: 132:

(i) SEQUENCE CHARACTERISTICS:
       (A) LENGTH: 86 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-NH2
           modified (xi) SEQUENCE DESCRIPTION: SEQ ID NO: 132:

GGGAGACAAG AAUAAACGCU CAAUCGAUAC UACUCCUGGA GAAAGGGAG         50

GACCGUGGAG GAUUCGACAG GAGGCUCACA ACAGGC                       86

(2) INFORMATION FOR SEQ ID NO: 133:

(i) SEQUENCE CHARACTERISTICS:
       (A) LENGTH: 86 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-NH2
           modified (xi) SEQUENCE DESCRIPTION: SEQ ID NO: 133:

GGGAGACAAG AAUAAACGCU CAAUCGAUAC UACUCCUGGA GAAAGGGAG         50

GAUCGUGGAG GAUUCGACAG GAGGCUCACA ACAGGC                       86

(2) INFORMATION FOR SEQ ID NO: 134:

(i) SEQUENCE CHARACTERISTICS:
       (A) LENGTH: 86 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-NH2
           modified (xi) SEQUENCE DESCRIPTION: SEQ ID NO: 134:

GGGAGACAAG AAUAAACGCU CAAGCGGUCU GAUUGAGCCU CCGUGGAGGG        50

UACGUGGAGG GAUUCGACAG GAGGCUCACA ACAGGC                       86

(2) INFORMATION FOR SEQ ID NO: 135:

(i) SEQUENCE CHARACTERISTICS:
       (A) LENGTH: 86 base pairs
       (B) TYPE: nucleic acid
       (C) STRANDEDNESS: single
       (D) TOPOLOGY: linear

```
        (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO: 135:

GGGAGACAAG AAUAAACGCU CAAAGGGUGG AUUGUGGAGG AAUGAGUUGU          50

CUAUGGACUC CAUUCGACAG GAGGCUCACA ACAGGC                        86

(2) INFORMATION FOR SEQ ID NO: 136:

(i) SEQUENCE CHARACTERISTICS:
            (A) LENGTH: 87 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO: 136:

GGGAGACAAG AAUAAACGCU CAAUCGAUAC UACUCCUGGA GAAAAGGGAG          50

GAUCGUGGAG GAAUUCGACA GGAGGCUCAC AACAGGC                       87

(2) INFORMATION FOR SEQ ID NO: 137:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO: 137:

GGGAGACAAG AAUAAACGCU CAACCGAUAC UACUCCUGGA GAAAAGGGAG          50

GAUCGUGGAG GAAUUCGACA GGAGGCUCAC AACAGGC                       87

(2) INFORMATION FOR SEQ ID NO: 138:

(i) SEQUENCE CHARACTERISTICS:
            (A) LENGTH:  86 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-NH2
                 modified (xi) SEQUENCE DESCRIPTION:  SEQ ID NO: 138:

GGGAGACAAG AAUAAACGCU CAAGGGAGGA UAGUGGAGGA AGAGCGUGUA          50

AUAAUGUUAC GAUUCGACAG GAGGCUCACA ACAGGC                        86

(2) INFORMATION FOR SEQ ID NO: 139:

(i) SEQUENCE CHARACTERISTICS:
```

(A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 139:

GGGAGACAAG AAUAAACGCU CAAUCGUAGC CUCCAGCGGA AUGCGGAGGG            50

CACGUGGAGG GGUUCGACAG GAGGCUCACA ACAGGC                          86

(2) INFORMATION FOR SEQ ID NO: 140:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 140:

GGGAGACAAG AAUAAACGCU CAAUCGAUAC UACUCCUGGA GAAAAGGGAG            50

GAUCGUGGAG GAAUUCGACA GGAGGCUCAC AACAGGC                         87

(2) INFORMATION FOR SEQ ID NO: 141:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 141:

GGGAGACAAG AAUAAACGCU CAACCGCAGC CUCCAGCAAU GCGGAGGGCA            50

CGUGGAGGGG UUCGACAGGA GGCUCACAAC AGGC                            84

(2) INFORMATION FOR SEQ ID NO: 142:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
            modified (xi) SEQUENCE DESCRIPTION: SEQ ID NO: 142:

GGGAGACAAG AAUAAACGCU CAAGAGCCUC CGAGAAUGAC GUGGAGGGUA          50

CGUGGAGGGG UAUUCGACAG GAGGCUCACA ACAGGC                         86

(2) INFORMATION FOR SEQ ID NO: 143:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
             modified (xi) SEQUENCE DESCRIPTION: SEQ ID NO: 143:

GGGAGACAAG AAUAAACGCU CAACCGUAGC CUCCAGCGGA ACGCGGAGGG          50

CACGUGGAGG GGUUCGACAG GAGGCUCACA ACAGGC                         86

(2) INFORMATION FOR SEQ ID NO: 144:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
             modified (xi) SEQUENCE DESCRIPTION: SEQ ID NO: 144:

GGGAGACAAG AAUAAACGCU CAAUGCCGAG AGGAGGGCUG AGGAGGACGC          50

GGCAUUAAGU GAUUCGACAG GAGGCUCACA ACAGGC                         86

(2) INFORMATION FOR SEQ ID NO: 145:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2
             modified (xi) SEQUENCE DESCRIPTION: SEQ ID NO: 145:

GGGAGACAAG AAUAAACGCU CAAUCGAUAC UACUCCUGGA GAAAAGGGAG          50

GAUCGUGGAG GAUUUCGACA GGAGGCUCAC AACAGGC                        87

(2) INFORMATION FOR SEQ ID NO: 146:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE:  RNA (ix) FEATURE:
         (D) OTHER INFORMATION:  All pyrimidines are 2'-NH2
             modified (xi) SEQUENCE DESCRIPTION:  SEQ ID NO: 146:

GGGAGACAAG AAUAAACGCU CAAGAGCCUC CGAGAAUGAC GUGGAGGGCA         50

CGUGGAGGGG AAUUCGACAG GAGGCUCACA ACAGGC                       86

(2) INFORMATION FOR SEQ ID NO: 147:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  RNA (ix) FEATURE:
         (D) OTHER INFORMATION:  All pyrimidines are 2'-NH2
             modified (xi) SEQUENCE DESCRIPTION:  SEQ ID NO: 147:

GGGAGACAAG AAUAAACGCU CAAUGCUGAG AGGAGGGCUG AGGAGGACAC         50

GGCAGUAUGA GAUUCGACAG GAGGCUCACA ACAGGC                       86

(2) INFORMATION FOR SEQ ID NO: 148:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  RNA (ix) FEATURE:
         (D) OTHER INFORMATION:  All pyrimidines are 2'-NH2
             modified (xi) SEQUENCE DESCRIPTION:  SEQ ID NO: 148:

GGGAGACAAG AAUAAACGCU CAAACGUAGC CUCCAGCGGA AUGCGGAGGG         50

CACGUGGAGG GGUUCGACAG GAGGCUCACA ACAGGC                       86

(2) INFORMATION FOR SEQ ID NO: 149:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  RNA (ix) FEATURE:
         (D) OTHER INFORMATION:  All pyrimidines are 2'-NH2
             modified (xi) SEQUENCE DESCRIPTION:  SEQ ID NO: 149:

GGGAGACAAG AAUAAACGCU CAAGCGGUCU GAUCGAGCCU CCGUGGAGGG         50

UACGUGGAGG GAUUCGACAG GAGGCUCACA ACAGGC                       86

(2) INFORMATION FOR SEQ ID NO: 150:

(i) SEQUENCE CHARACTERISTICS:

(A) LENGTH:  86 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-NH2
             modified (xi) SEQUENCE DESCRIPTION:  SEQ ID NO: 150:

GGGAGACAAG AAUAAACGCU CCAGCGGUCU GAUUGAGCCU CCGUGGAGGG          50

CACGUGGAGG GAUUCGACAG GAGGCUCACA ACAGGC                        86

(2) INFORMATION FOR SEQ ID NO: 151:

(i) SEQUENCE CHARACTERISTICS:
         (A) LENGTH:  86 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-NH2
             modified (xi) SEQUENCE DESCRIPTION:  SEQ ID NO: 151:

GGGAGACAAG AAUAAACGCU CAAUGCCGAG AGGAGGGCUG AGGAGGACAC          50

GGCAGUAUGU AAUUCGACAG GAGGCUCACA ACAGGC                        86

(2) INFORMATION FOR SEQ ID NO: 152:

(i) SEQUENCE CHARACTERISTICS:
         (A) LENGTH:  86 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-NH2
             modified (xi) SEQUENCE DESCRIPTION:  SEQ ID NO: 152:

GGGAGACAAG AAUAAACGCU CAACCGUAGC CUCCAGCGGA AUGUGGAGGG          50

CACGUGGAGG GGUUCGACAG GAGGCUCACA ACAGGC                        86

(2) INFORMATION FOR SEQ ID NO: 153:

(i) SEQUENCE CHARACTERISTICS:
         (A) LENGTH:  85 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-NH2
             modified (xi) SEQUENCE DESCRIPTION: SEQ ID NO: 153:

GGGAGACAAG AAUAAACGCU CAAAAGGUGG GUCGUGGAGG AAUGAGCUCG          50

CUCCCAGCUA AUUCGACAGG AGGCUCACAA CAGGC          85

(2) INFORMATION FOR SEQ ID NO: 154:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 154:

GGGAGACAAG AAUAAACGCU CAAAGAGUGC AGGUCUGGGG CGCCACAAUU          50

ACAACGGCAA UAAUUCGACA GGAGGCUCAC AACAGGC          87

(2) INFORMATION FOR SEQ ID NO: 155:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 155:

GGGAGACAAG AAUAAACGCU CAAGUCUUCC AUGGGGAGCC ACAUUAACGG          50

CGCAAUACUG AACUUCGACA GGAGGCUCAC AACAGGC          87

(2) INFORMATION FOR SEQ ID NO: 156:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 156:

GGGAGACAAG AAUAAACGCU CAACUCGGGA GCCAGAGUAA CAACGGCACU          50

AUAUAAUUUU ACUUCGACAG GAGGCUCACA ACAGGC          86

(2) INFORMATION FOR SEQ ID NO: 157:

(i) SEQUENCE CHARACTERISTICS:

```
        (A) LENGTH:  86 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 157:

GGGAGACAAG AAUAAACGCU CAAAGAGCCG UUUUGGGGAC CCACAGUAAC           50

GGGUUUAUGG UAUUCGACAG GAGGCUCACA ACAGGC                          86

(2) INFORMATION FOR SEQ ID NO: 158:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 158:

GGGAGACAAG AAUAAACGCU CAAGUCGGAG CGAUGGAGAG CCACGAUAUA           50

CGGUCUGUGC GCUUCGACAG GAGGCUCACA ACAGGC                          86

(2) INFORMATION FOR SEQ ID NO: 159:

(i) SEQUENCE CHARACTERISTICS:
        (A) LENGTH:  82 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 159:

GGGAGACAAG AAUAAACGCU CAAAGUAACG UGGGGAGCCA CACGUAAUAC           50

GGCACUAAUU CGACAGGAGG CUCACAACAG GC                              82

(2) INFORMATION FOR SEQ ID NO: 160:

(i) SEQUENCE CHARACTERISTICS:
        (A) LENGTH:  87 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified
```

```
        (ix) FEATURE:
              (D) OTHER INFORMATION: All C's are 2'-F modified (xi) SEQUENCE DESCRIPTION: SEQ ID NO: 160:

GGGAGACAAG AAUAAACGCU CAAGGUACGA CCAAGGAAUG UGGGUGGAAG          50

AGGGCGCCGU ACCUUCGACA GGAGGCUCAC AACAGGC                       87

(2) INFORMATION FOR SEQ ID NO: 161:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All U's are 2'-NH2 modified (ix) FEATURE:
              (D) OTHER INFORMATION: All C's are 2'-F modified (xi) SEQUENCE DESCRIPTION: SEQ ID NO: 161:

GGGAGACAAG AAUAAACGCU CAAGAUCCUG CGACGCCAGG GGUGGAUAGG          50

GGGAAGGGAG CGGUUCGACA GGAGGCUCAC AACAGGC                       87

(2) INFORMATION FOR SEQ ID NO: 162:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All U's are 2'-NH2 modified (ix) FEATURE:
              (D) OTHER INFORMATION: All C's are 2'-F modified (xi) SEQUENCE DESCRIPTION: SEQ ID NO: 162:

GGGAGACAAG AAUAAACGCU CAAGACGAAC GACCAAGGGA CGGGUGGGCA          50

AAUAGGGAUG CCGUUCGACA GGAGGCUCAC AACAGGC                       87

(2) INFORMATION FOR SEQ ID NO: 163:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All U's are 2'-NH2 modified (ix) FEATURE:
              (D) OTHER INFORMATION: All C's are 2'-F modified (xi) SEQUENCE DESCRIPTION: SEQ ID NO: 163:

GGGAGACAAG AAUAAACGCU CAAGGUACGA CCAAGGAAUG UGGGUGGAAG          50

AGGGUGCCGU ACCUUCGACA GGAGGCUCAC AACAGGC                       87
```

(2) INFORMATION FOR SEQ ID NO: 164:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 164:

```
GGGAGACAAG AAUAAACGCU CAACAACGCU GACCAUGGGA GGAAUGUGGG          50

AAGGGCGCCA GCGUUCGACA GGAGGCUCAC AACAGGC                        87
```

(2) INFORMATION FOR SEQ ID NO: 165:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 165:

```
GGGAGACAAG AAUAAACGCU CAACAGCCAA GGGUUGGAUA GGGGGUAGGG          50

AGCCGUAGCA GCGUUCGACA GGAGGCUCAC AACAGGC                        87
```

(2) INFORMATION FOR SEQ ID NO: 166:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 166:

```
GGGAGACAAG AAUAAACGCU CAACCGCCUG CGAUAGUUAG ACCGUUGAGC          50

UGAGAGCAAC ACUUCGACA GGAGGCUCAC AACAGGC                         87
```

(2) INFORMATION FOR SEQ ID NO: 167:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION:  All U's are 2'-NH2 modified (ix) FEATURE:
            (D) OTHER INFORMATION:  All C's are 2'-F modified (xi) SEQUENCE DESCRIPTION:  SEQ ID NO: 167:

GGGAGACAAG AAUAAACGCU CAAAAGGUGG GUUGAGGAGG AAAGUAGCGU         50

GAGUCAGUAC CAUUCGACAG GAGGCUCACA ACAGGC                        86

(2) INFORMATION FOR SEQ ID NO: 168:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All U's are 2'-NH2 modified (ix) FEATURE:
            (D) OTHER INFORMATION:  All C's are 2'-F modified (xi) SEQUENCE DESCRIPTION:  SEQ ID NO: 168:

GGGAGACAAG AAUAAACGCU CAAAGGGAGG AUUGUGGAGG AAGGGAGUGG         50

AAGUGUCCCA GCCUUCGACA GGAGGCUCAC AACAGGC                       87

(2) INFORMATION FOR SEQ ID NO: 169:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All U's are 2'-NH2 modified (ix) FEATURE:
            (D) OTHER INFORMATION:  All C's are 2'-F modified (xi) SEQUENCE DESCRIPTION:  SEQ ID NO: 169:

GGGAGACAAG AAUAAACGCU CAAGGAUGAC CAAGCGUCGA ACGAGGGAGG         50

AUUGUGGUGG AGGUUCGACA GGAGGCUCAC AACAGGC                       87

(2) INFORMATION FOR SEQ ID NO: 170:

(i) SEQUENCE CHARACTERISTICS:
            (A) LENGTH:  87 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All U's are 2'-NH2 modified (ix) FEATURE:
            (D) OTHER INFORMATION:  All C's are 2'-F modified (xi) SEQUENCE DESCRIPTION: SEQ ID NO: 170:

GGGAGACAAG AAUAAACGCU CAAGGGUGGA UUGUGGAGGA AGUAGCGCAG          50

GGUUCCGUAA GCCUUCGACA GGAGGCUCAC AACAGGC                       87

(2) INFORMATION FOR SEQ ID NO: 171:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 171:

GGGAGACAAG AAUAAACGCU CAAAGGAGCG CCAUGAAGCA AAGGGAGGAU          50

UGUGGUGGAA GGCUUCGACA GGAGGCUCAC AACAGGC                       87

(2) INFORMATION FOR SEQ ID NO: 172:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 172:

GGGAGACAAG AAUAAACGCU CAAACUGGAG CCAUACAGAC GAGAGGAUGG          50

GUGUGUGGAG GAUUCGACAG GAGGCUCACA ACAGGC                        86

(2) INFORMATION FOR SEQ ID NO: 173:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-NH2 modified (ix) FEATURE:
        (D) OTHER INFORMATION: All C's are 2'-F modified (xi) SEQUENCE DESCRIPTION: SEQ ID NO: 173:

GGGAGACAAG AAUAAACGCU CAAAGGGAGG AUUGUGGAGG AAGGGAGUGG          50

AAGUGUCUCA GCCUUCGACA GGAGGCUCAC AACAGGC                       87

(2) INFORMATION FOR SEQ ID NO: 174:

(i) SEQUENCE CHARACTERISTICS:

(A) LENGTH:  87 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 174:

GGGAGACAAG AAUAAACGCU CAAUCGGGUG AGGACUGGUA GAAAAGGAG         50

GGUUGUGGAG GAGUUCGACA GGAGGCUCAC AACAGGC                     87

(2) INFORMATION FOR SEQ ID NO: 175:

(i) SEQUENCE CHARACTERISTICS:
        (A) LENGTH:  87 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 175:

GGGAGACAAG AAUAAACGCU CAAACCUGAU AACCGCGGAG GGAGGAUAGA       50

GGAGGAAGUG CGGUUCGACA GGAGGCUCAC AACAGGC                     87

(2) INFORMATION FOR SEQ ID NO: 176:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 176:

GGGAGACAAG AAUAAACGCU CAAAGGCAGC CCCUCGACGA GAAAGGUGGG       50

UAGUGGAGGA ACUUCGACAG GAGGCUCACA ACAGGC                      86

(2) INFORMATION FOR SEQ ID NO: 177:

(i) SEQUENCE CHARACTERISTICS:
        (A) LENGTH:  87 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
         (D) OTHER INFORMATION: All C's are 2'-F modified (xi) SEQUENCE DESCRIPTION: SEQ ID NO: 177:

GGGAGACAAG AAUAAACGCU CAACUUACGA CACCAAAGGG AGGAUUGUGG          50

UGGAAUGGGG UCGUUCGACA GGAGGCUCAC AACAGGC                       87

(2) INFORMATION FOR SEQ ID NO: 178:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are 2'-F
             modified (xi) SEQUENCE DESCRIPTION: SEQ ID NO: 178:

GGGAAACGGC UGUAACAAAC AAGGUGGGGG GCCACACA                      38

(2) INFORMATION FOR SEQ ID NO: 179:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are 2'-F
             modified (xi) SEQUENCE DESCRIPTION: SEQ ID NO: 179:

GGGAGACAAG AAUAAACGCU CAAGUCUGAC UAUUGGGGCG CCACAAUAUC          50

AACGGC                                                         56

(2) INFORMATION FOR SEQ ID NO: 180:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are 2'-F
             modified (xi) SEQUENCE DESCRIPTION: SEQ ID NO: 180:

AAGAAUAAAC GCUCAAGCUG CCCAAGGAAU UUAACUUGGA CCGCGAUCU           49

(2) INFORMATION FOR SEQ ID NO: 181:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: RNA (ix) FEATURE:
              (D) OTHER INFORMATION: All pyrimidines are 2'-F
                    modified (xi) SEQUENCE DESCRIPTION: SEQ ID NO: 181:

AAGCAAAGGG AGGAUUGUGG UGGAAGGCUU C                                              31

(2) INFORMATION FOR SEQ ID NO: 182:

(i) SEQUENCE CHARACTERISTICS:
              (A) LENGTH: 51 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-NH2
                    modified (xi) SEQUENCE DESCRIPTION: SEQ ID NO: 182:

GGGACGCUCA AGAGCUGGUG AGCCACGUAU ACGGCCUUAG GGGCUUGGGC                           50

G                                                                               51

(2) INFORMATION FOR SEQ ID NO: 183:

(i) SEQUENCE CHARACTERISTICS:
              (A) LENGTH: 59 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All U's are 2'-NH2 modified (ix) FEATURE:
              (D) OTHER INFORMATION: All C's are 2'-F modified (xi) SEQUENCE DESCRIPTION: SEQ ID NO: 183:

GGGAGACAAG AAUAAACGCU CAAAGAGUGC AGGUCUGGGG CGCCACAAUU                           50

AGAACGGCA                                                                       59

(2) INFORMATION FOR SEQ ID NO: 184:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All U's are 2'-NH2 modified (ix) FEATURE:
              (D) OTHER INFORMATION: All C's are 2'-F modified (xi) SEQUENCE DESCRIPTION: SEQ ID NO: 184:

GCUCAACCGC CUGCGAUAGU UAGACCG                                                   27

(2) INFORMATION FOR SEQ ID NO: 185:

(i) SEQUENCE CHARACTERISTICS:
              (A) LENGTH: 47 base pairs
              (B) TYPE: nucleic acid

```
        (C) STRANDEDNESS:  single
        (D) TOPOLOGY:  linear (ii) MOLECULE TYPE:  RNA (ix) FEATURE:
        (D) OTHER INFORMATION:  All U's are 2'-NH2 modified (ix) FEATURE:
        (D) OTHER INFORMATION:  All C's are 2'-F modified (xi) SEQUENCE DESCRIPTION:  SEQ ID NO: 185:

CCUGCGACGC CAGGGGUGGA UAGGGGGAAG GGAGCGGUUC GACAGGA                47

(2) INFORMATION FOR SEQ ID NO: 186:

(i) SEQUENCE CHARACTERISTICS:
        (A) LENGTH:  87 base pairs
        (B) TYPE:  nucleic acid
        (C) STRANDEDNESS:  single
        (D) TOPOLOGY:  linear (ii) MOLECULE TYPE:  RNA (xi) SEQUENCE DESCRIPTION:  SEQ ID NO: 186:

GGGAGACAAG AAUAAACGCU CAANNNNNNN NNNNNNNNNN NNNNNNNNNN             50

NNNNNNNNNN NNNUUCGACA GGAGGCUCAC AACAGGC                           87

(2) INFORMATION FOR SEQ ID NO: 187:

(i) SEQUENCE CHARACTERISTICS:
        (A) LENGTH:  40 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 187:

TAATACGACT CACTATAGGG AGACAAGAAT AAACGCTCAA                        40

(2) INFORMATION FOR SEQ ID NO: 188:

(i) SEQUENCE CHARACTERISTICS:
        (A) LENGTH:  24 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 188:

GCCTGTTGTG AGCCTCCTGT CGAA                                         24

(2) INFORMATION FOR SEQ ID NO: 189:

(i) SEQUENCE CHARACTERISTICS:
        (A) LENGTH:  84 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F
            modified
```

(xi) SEQUENCE DESCRIPTION: SEQ ID NO: 189:

GGGAGACAAG AAUAAACGCU CAAACAUCGU AUAACUCUAA GGGCCUGGAU          50

AUACGAUGAA UUCGACAGGA GGCUCACAAC AGGC                           84

(2) INFORMATION FOR SEQ ID NO: 190:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 190:

GGGAGACAAG AAUAAACGCU CAAACAUCGU AUAACUCUAA GCGCCUGGAU          50

AUACGAUGAA UUCGACAGGA GGCUCACAAC AGGC                           84

(2) INFORMATION FOR SEQ ID NO: 191:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 191:

GGGAGACAAG AAUAAACGCU CAAACAUCGU AUAACUCUAA GAGCCUGGAU          50

AUACGAUGAA UUCGACAGGA GGCUCACAAC AGGC                           84

(2) INFORMATION FOR SEQ ID NO: 192:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 192:

GGGAGACAAG AAUAAACGCU CAAACAUCGU AUAACUCUAA GUGCCUGGAU          50

AUACGAUGAA UUCGACAGGA GGCUCACAAC AGGC                           84

(2) INFORMATION FOR SEQ ID NO: 193:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: RNA (ix) FEATURE:
             (D) OTHER INFORMATION: All pyrimidines are 2'-F
                 modified (xi) SEQUENCE DESCRIPTION: SEQ ID NO: 193:

GGGAGACAAG AAUAAACGCU CAAACAUCGU AUAAUCUCUA AGAGCCUGGA            50

UAUACGAUGA AUUCGACAGG AGGCUCACAA CAGGC                           85

(2) INFORMATION FOR SEQ ID NO: 194:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All pyrimidines are 2'-F
                 modified (xi) SEQUENCE DESCRIPTION: SEQ ID NO: 194:

GGGAGACAAG AAUAAACGCU CAAACAUCGU AUAAUCUCUC UAAGAGCCUG            50

GAAUACGAUG AAUUCGACAG GAGGCUCACA ACAGGC                          86

(2) INFORMATION FOR SEQ ID NO: 195:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All pyrimidines are 2'-F
                 modified (xi) SEQUENCE DESCRIPTION: SEQ ID NO: 195:

GGGAGACAAG AAUAAACGCU CAAAUCCCAA UCUCUAAGAG CCUGGAUAAG            50

AAUGCGCAUU GGGCUUCGAC AGGAGGCUCA CAACAGGC                        88

(2) INFORMATION FOR SEQ ID NO: 196:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All pyrimidines are 2'-F
                 modified (xi) SEQUENCE DESCRIPTION: SEQ ID NO: 196:

GGGAGACAAG AAUAAACGCU CAAAUCCCAA UCUCUAAGAG CCUGGAUGAC            50

AAUCGCAUUG GCUUCGACA GGAGGCUCAC AACAGGC                          87

(2) INFORMATION FOR SEQ ID NO: 197:

(i) SEQUENCE CHARACTERISTICS:

(A) LENGTH: 88 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 197:

GGGAGACAAG AAUAAACGCU CAAAUCCCAA UCUCUAAGAG CCUGGAUGAG          50

AAUGCGCAUU GGGCUUCGAC AGGAGGCUCA CAACAGGC                      88

(2) INFORMATION FOR SEQ ID NO: 198:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 198:

GGGAGACAAG AAUAAACGCU CAACUGAGAU CUCUAAGAGC CUGGACUCAG          50

CUCCGACUGA CCUUCGACAG GAGGCUCACA ACAGGC                        86

(2) INFORMATION FOR SEQ ID NO: 199:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 199:

GGGAGACAAG AAUAAACGCU CAACUGAGAU CUCUAAGAGC CUGGACUCAG          50

CUCCGAUUGA UCCUUCGACA GGAGGCUCAC AACAGGC                       87

(2) INFORMATION FOR SEQ ID NO: 200:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 200:

GGGAGACAAG AAUAAACGCU CAACUGAGAU CUCUAAGAGC CUGGACUCAG                50

CUCCGAUUGA ACCUUCGACA GGAGGCUCAC AACAGGC                              87

(2) INFORMATION FOR SEQ ID NO: 201:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 201:

GGGAGACAAG AAUAAACGCU CAAUCUCUAU GAGCCUGGAU CGACGAACUC                50

UCUACGGGCU GUGUUCGACA GGAGGCUCAC AACAGGC                              87

(2) INFORMATION FOR SEQ ID NO: 202:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 202:

GGGAGACAAG AAUAAACGCU CAAUCUCUAA GAGCCUGGAU GUCGAGGGGC                50

CAUUUCGCAC GCUUCGACAG GAGGCUCACA ACAGGC                               86

(2) INFORMATION FOR SEQ ID NO: 203:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F
            modified (xi) SEQUENCE DESCRIPTION: SEQ ID NO: 203:

GGGAGACAAG AAUAAACGCU CAAAUCUCUA CUGAGCCUGG AUUCGCCAGA                50

AGUUUUAUCA CAGUUUCGAC AGGAGGCUCA CAACAGGC                             88

(2) INFORMATION FOR SEQ ID NO: 204:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 204:

GGGAGACAAG AAUAAACGCU CAACGUAAAA GUUAUCGAAU CUCUGUGAGC       50

CUGGAUCGAU UACUUCGACA GGAGGCUCAC AACAGGC                    87

(2) INFORMATION FOR SEQ ID NO: 205:

(i) SEQUENCE CHARACTERISTICS:
            (A) LENGTH:  97 base pairs
            (B) TYPE:  nucleic acid
            (C) STRANDEDNESS:  single
            (D) TOPOLOGY:  linear (ii) MOLECULE TYPE:  RNA (ix) FEATURE:
             (D) OTHER INFORMATION:  All pyrimidines are 2'-F
                 modified (xi) SEQUENCE DESCRIPTION:  SEQ ID NO: 205:

GGGAGACAAG AAUAAACGCU CAACUGAGAU CUCUAAGAGC CUGGACUCAG       50

CUACGAUUGA GCGUUUAUUC UUGUUCGACA GGAGGCUCAC AACAGGC         97

(2) INFORMATION FOR SEQ ID NO: 206:

(i) SEQUENCE CHARACTERISTICS:
            (A) LENGTH:  77 base pairs
            (B) TYPE:  nucleic acid
            (C) STRANDEDNESS:  single
            (D) TOPOLOGY:  linear (ii) MOLECULE TYPE:  RNA (xi) SEQUENCE DESCRIPTION:  SEQ ID NO: 206:

GGGAGCUCAG AAUAAACGCU CAANNNNNNN NNNNNNNNNN NNNNNNNNNN       50

NNNUUCGACA UGAGGCCCGG AUCCGGC                               77

(2) INFORMATION FOR SEQ ID NO: 207:

(i) SEQUENCE CHARACTERISTICS:
            (A) LENGTH:  24 base pairs
            (B) TYPE:  nucleic acid
            (C) STRANDEDNESS:  single
            (D) TOPOLOGY:  linear (ii) MOLECULE TYPE:  DNA (xi) SEQUENCE DESCRIPTION:  SEQ ID NO: 207:

GCCGGATCCG GGCCTCATGT CGAA                                  24

(2) INFORMATION FOR SEQ ID NO: 208:

(i) SEQUENCE CHARACTERISTICS:
            (A) LENGTH:  48 base pairs
            (B) TYPE:  nucleic acid
            (C) STRANDEDNESS:  single
            (D) TOPOLOGY:  linear (ii) MOLECULE TYPE:  DNA (xi) SEQUENCE DESCRIPTION: SEQ ID NO: 208:

CCGAAGCTTA ATACGACTCA CTATAGGGAG CTCAGAATAA ACGCTCAA        48

(2) INFORMATION FOR SEQ ID NO: 209:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION: SEQ ID NO: 209:

GGGAGCTCAG AATAAACGCT CAAACGGCTG ACAACGGCTG GACTTGCGTA        50

TTGTTCGACA TGAGGCCCGG ATCCGGC                                77

(2) INFORMATION FOR SEQ ID NO: 210:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION: SEQ ID NO: 210:

GGGAGCTCAG AATAAACGCT CAAGCGCTTG ACCATTTCGT AGGGTCGCCC        50

TTGTTCGACA TGAGGCCCGG ATCCGGC                                77

(2) INFORMATION FOR SEQ ID NO: 211:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION: SEQ ID NO: 211:

GGGAGCTCAG AATAAACGCT CAAGATCGAC GCATCGAGTC GCCTCATCGC        50

TCCTTCGACA TGAGGCCCGG ATCCGGC                                77

(2) INFORMATION FOR SEQ ID NO: 212:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION: SEQ ID NO: 212:

GGGAGCTCAG AATAAACGCT CAACGCACTC GGACGGAATC TCCGTAGGAC        50

ACGTTCGACA TGAGGCCCGG ATCCGGC                                77

(2) INFORMATION FOR SEQ ID NO: 213:

(i) SEQUENCE CHARACTERISTICS:
        (A) LENGTH:  77 base pairs
        (B) TYPE:  nucleic acid (C) STRANDEDNESS: single
        (D) TOPOLOGY: linear (ii) MOLECULE TYPE: DNA (xi) SEQUENCE DESCRIPTION: SEQ ID NO: 213:

GGGAGCTCAG AATAAACGCT CAATGTCATG CATGTGTGTC GCCTCATCAC           50

GCATTCGACA TGAGGCCCGG ATCCGGC                                   77

(2) INFORMATION FOR SEQ ID NO: 214:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 214:

GGGAGCTCAG AATAAACGCT CAACCACTGG CTAGGAACTC GAGTACTGGG           50

TGGTTCGACA TGAGGCCCGG ATCCGGC                                   77

(2) INFORMATION FOR SEQ ID NO: 215:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 215:

GGGAGCTCAG AATAAACGCT CAATTCGAAG CCACGTTTCA TGTCCGTCGC           50

TGCTTCGACA TGAGGCCCGG ATCCGGC                                   77

(2) INFORMATION FOR SEQ ID NO: 216:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 216:

GGGAGCTCAG AATAAACGCT CAACAGTGGA GGCTGTCCAA ACCCACCCAC           50

CCCTTCGACA TGAGGCCCGG ATCCGGC                                   77

(2) INFORMATION FOR SEQ ID NO: 217:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 217:

GGGAGCTCAG AATAAACGCT CAAGTGGAGG GTACGTGGAG GGGAGAGCGA         50

TATTCGACAT GAGGCCCGGA TCCGGC                                   76

(2) INFORMATION FOR SEQ ID NO: 218:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 218:

GGGAGCTCAG AATAAACGCT CAATCTCATG CTCGCGTGCG TCGCCTCAAC         50

CATTCGACAT GAGGCCCGGA TCCGGC                                   76

(2) INFORMATION FOR SEQ ID NO: 219:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 219:

GGGAGCTCAG AATAAACGCT CAATCCCTCA GTGTCAAGTG CGTCGCCTCA         50

GCATTCGACA TGAGGCCCGG ATCCGGC                                  77

(2) INFORMATION FOR SEQ ID NO: 220:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 220:

GGGAGCTCAG AATAAACGCT CAACTTCTTG GCCCCGTCTC AATGTCCGTA         50

CTTCTTCGAC ATGAGGCCCG GATCCGGC                                 78

(2) INFORMATION FOR SEQ ID NO: 221:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 221:

GGGAGCTCAG AATAAACGCT CAACGTGATT TGGCCACGGG AAAGAGCCAT         50

ACCTTCGACA TGAGGCCCGG ATCCGGC                                  77

(2) INFORMATION FOR SEQ ID NO: 222:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 222:

```
GGGAGCTCAG AATAAACGCT CAACGTTGAA CGCTTGGTTT CATGTCCCTC          50

GCCTTCGACA TGAGGCCCGG ATCCGGC                                   77
```

(2) INFORMATION FOR SEQ ID NO: 223:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 223:

```
GGGAGCTCAG AATAAACGCT CAACGTCGAT CGCGTGCTGT AGCCTCAGGC          50

ACCTTCGACA TGAGGCCCGG ATCCGGC                                   77
```

(2) INFORMATION FOR SEQ ID NO: 224:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 224:

```
GGGAGCTCAG AATAAACGCT CAAGGTGGAA GGCCTTTGAA GCCCGTACAT          50

CTCCTTCGAC ATGAGGCCCG GATCCGGC                                  78
```

(2) INFORMATION FOR SEQ ID NO: 225:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 225:

```
GGGAGCTCAG AATAAACGCT CAAGGTCGAA CTAGCGCTGG AGCGTGCGTT          50

GGTTTCGACA TGAGGCCCGG ATCCGGC                                   77
```

(2) INFORMATION FOR SEQ ID NO: 226:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 226:

GGGAGCTCAG AATAAACGCT CAAGTCGCTC GATCGTTTCA TGCCCGTCCG        50

ACCTTCGACA TGAGGCCCGG ATCCGGC                                77

(2) INFORMATION FOR SEQ ID NO: 227:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 227:

GGGAGCTCAG AATAAACGCT CAAGTCGATG CGCAGTCCGC CTCAGCTGCA        50

CTGTTCGACA TGAGGCCCGG ATCCGGC                                77

(2) INFORMATION FOR SEQ ID NO: 228:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 228:

GGGAGCTCAG AATAAACGCT CAAGGTGTGC CCAAGGCCCT TGAGAGAGGC        50

GTGTTCGACA TGAGGCCCGG ATCCGGC                                77

(2) INFORMATION FOR SEQ ID NO: 229:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 229:

GGGAGCTCAG AATAAACGCT CAACGTCTAG GAACTGCGTC GCCTCAACAG        50

CGCTTCGACA TGAGGCCCGG ATCCGGC                                77

(2) INFORMATION FOR SEQ ID NO: 230:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 230:

GGGAGCTCAG AATAAACGCT CAAGTCGGAT GGTTTTGCGC GTTTCCCGTT        50

CGACATGAGG CCCGGATCCG GC                                     72

(2) INFORMATION FOR SEQ ID NO: 231:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 231:

```
GGGAGCTCAG AATAAACGCT CAACCTCATC CTCGCACGCC ATCGCCTGAA        50
CCGTTCGACA TGAGGCCCGG ATCCGGC                                 77
```

(2) INFORMATION FOR SEQ ID NO: 232:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 232:

```
GGGAGCTCAG AATAAACGCT CAAGGTGTGC CAAAGGCCCT TGAGAGAGGC        50
GTATTCGACA TGAGGCCCGG ATCCGGC                                 77
```

(2) INFORMATION FOR SEQ ID NO: 233:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 233:

```
GGGAGCTCAG AATAAACGCT CAAGGCCGCA TGCCCCTCCT AACAGCATGC        50
AACTTCGACA TGAGGCCCGG ATCCGGC                                 77
```

(2) INFORMATION FOR SEQ ID NO: 234:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 234:

```
GGGAGCTCAG AATAAACGCT CAACCCTCGT GCGTGCGCTT GGAGCGTGGC        50
GCATTCGACA TGAGGCCCGG ATCCGGC                                 77
```

(2) INFORMATION FOR SEQ ID NO: 235:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 235:

GGGAGCTCAG AATAAACGCT CAAGTCGCTC GATCGTTTCA TGTCCGTTCG        50

ACCTTCGACA TGAGGCCCGG ATCCGGC        77

(2) INFORMATION FOR SEQ ID NO: 236:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 236:

GGGAGCTCAG AATAAACGCT CAAGTCCACA CTTTGCCGAG CGTCCTAGTG        50

TTCGACATGA GGCCCGGATC CGGC        74

(2) INFORMATION FOR SEQ ID NO: 237:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 237:

GGGAGCTCAG AATAAACGCT CAACGGGTGA ATCACGGCTG GTGCGTTGCC        50

CCTTCGACAT GAGGCCCGGA TCCGGC        76

(2) INFORMATION FOR SEQ ID NO: 238:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 238:

GGGAGCTCAG AATAAACGCT CAACGTCGAC GCACTGTGCC GCCTCACACA        50

CGCTTCGACA TGAGGCCCGG ATCCGGC        77

(2) INFORMATION FOR SEQ ID NO: 239:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 239:

GGGAGCTCAG AATAAACGCT CAAGCGAACG TCATGCCGCC TCATCATGCC        50

ACGTTCGACA TGAGGCCCGG ATCCGGC        77

```
(2) INFORMATION FOR SEQ ID NO: 240:

(i) SEQUENCE CHARACTERISTICS:
        (A) LENGTH:  76 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 240:

GGGAGCTCAG AATAAACGCT CAACTAGGCC CACCGTCCCT TCTAACAACG            50

TCTTCGACAT GAGGCCCGGA TCCGGC                                      76

(2) INFORMATION FOR SEQ ID NO: 241:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 241:

GGGAGCTCAG AATAAACGCT CAACAGTCAC GAACGTGCGC CGGAAGAACG            50

CTCTTCGACA TGAGGCCCGG ATCCGGC                                     77

(2) INFORMATION FOR SEQ ID NO: 242:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 242:

GGGAGCTCAG AATAAACGCT CAATGTCGCA CGTGTCCCGG CCCGCCCTAC            50

CCCTTCGACA TGAGGCCCGG ATCCGGC                                     77

(2) INFORMATION FOR SEQ ID NO: 243:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 243:

GGGAGCTCAG AATAAACGCT CAACAGGTGG CACCGCCCTT CCAACACGGT            50

GCGTTCGACA TGAGGCCCGG ATCCGGC                                     77

(2) INFORMATION FOR SEQ ID NO: 244:

(i) SEQUENCE CHARACTERISTICS:
        (A) LENGTH:  74 base pairs
        (B) TYPE:  nucleic acid
        (C) STRANDEDNESS:  single
        (D) TOPOLOGY:  linear (ii) MOLECULE TYPE:  DNA
```

```
    (xi) SEQUENCE DESCRIPTION: SEQ ID NO: 244:

GGGAGCTCAG AATAAACGCT CAAGTCCACA CTTTGCCGAG CGTCCTAGTG         50

TTCGACATGA GGCCCGGATC CGGC                                    74

(2) INFORMATION FOR SEQ ID NO: 245:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 245:

GGGAGCTCAG AATAAACGCT CAAATGGTGG AGGCCATCTC AAACCCACGA         50

CACTTCGACA TGAGGCCCGG ATCCGGC                                 77

(2) INFORMATION FOR SEQ ID NO: 246:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 246:

GGGAGCTCAG AATAAACGCT CAACGCCGAG ACCCACCTCA TAACACCGCT         50

ACCTTCGACA TGAGGCCCGG ATCCGGC                                 77

(2) INFORMATION FOR SEQ ID NO: 247:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 247:

GGGAGCTCAG AATAAACGCT CAATGAGGCG CGCCACAGGA TGGCCCTCAA         50

CCCTTCGACA TGAGGCCCGG ATCCGGC                                 77

(2) INFORMATION FOR SEQ ID NO: 248:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 248:

GGGAGCTCAG AATAAACGCT CAAGTCCGCA TGATGCTTCG AACAGCATAC         50

AACTTCGACA TGAGGCCCGG ATCCGGC                                 77
```

```
(2) INFORMATION FOR SEQ ID NO: 249:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 249:

GGGAGCTCAG AATAAACGCT CAAGGTGTGC CCCTACGTGC GGCCCTTCGT           50

TTATTCGACA TGAGGCCCGG ATCCGGC                                   77

(2) INFORMATION FOR SEQ ID NO: 250:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 250:

GGGAGCTCAG AATAAACGCT CAACGGCTTG CAGGTCGCCG AAATGACCGC           50

ACATTCGACA TGAGGCCCGG ATCCGGC                                   77

(2) INFORMATION FOR SEQ ID NO: 251:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 251:

GGGAGCTCAG AATAAACGCT CAACTAGTTC AACCGTCCCT TCTAACAACC           50

GTCTTCGACA TGAGGCCCGG ATCCGGC                                   77

(2) INFORMATION FOR SEQ ID NO: 252:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 252:

GGGAGCTCAG AATAAACGCT CAACCTGGTG GTCGTGCGGC TGTCGCCTCA           50

AGGTTCGACA TGAGGCCCGG ATCCGGC                                   77

(2) INFORMATION FOR SEQ ID NO: 253:

(i) SEQUENCE CHARACTERISTICS:
        (A) LENGTH:  77 base pairs
        (B) TYPE:  nucleic acid
        (C) STRANDEDNESS:  single
        (D) TOPOLOGY:  linear (ii) MOLECULE TYPE:  DNA
```

-continued

```
    (xi) SEQUENCE DESCRIPTION: SEQ ID NO: 253:

GGGAGCTCAG AATAAACGCT CAAGATCGAA GTTGTCGTCC GCCTCAGCGA          50

CTCTTCGACA TGAGGCCCGG ATCCGGC                                  77

(2) INFORMATION FOR SEQ ID NO: 254:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 254:

GGGAGCTCAG AATAAACGCT CAATGTCGAG TGCGATGGAG GAGTAGGGAT          50

GCATTCGACA TGAGGCCCGG ATCCGGC                                  77

(2) INFORMATION FOR SEQ ID NO: 255:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 255:

GGGAGCTCAG AATAAACGCT CAATGTCGAT CGTGTCAAGG TCCGTCCTAC          50

TTCTTCGACA TGAGGCCCGG ATCCGGC                                  77

(2) INFORMATION FOR SEQ ID NO: 256:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 256:

GGGAGGACGA TGCGGNNNNN NNNNNNNNNN NNNNNNNNNN NNNNNNNNNN          50

NNNNNCAGAC GACTCGCCCG A                                        71

(2) INFORMATION FOR SEQ ID NO: 257:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 257:

GGGAGGACGA TGCGG                                               15

(2) INFORMATION FOR SEQ ID NO: 258:

(i) SEQUENCE CHARACTERISTICS:
        (A) LENGTH: 20 base pairs
        (B) TYPE: nucleic acid
```

```
        (C) STRANDEDNESS:  single
        (D) TOPOLOGY:  linear (ii) MOLECULE TYPE:  DNA (ix) FEATURE:
        (D) OTHER INFORMATION:  N at positions 1-4 is biotin (xi) SEQUENCE DESCRIPTION:  SEQ ID NO: 258:

NNNNTCGGGC GAGTCGTCTG                                           20
```